United States Patent
Ahrens et al.

(10) Patent No.: US 9,198,425 B2
(45) Date of Patent: Dec. 1, 2015

(54) HERBICIDALLY-EFFECTIVE SULFINYL AMINOBENZAMIDES

(71) Applicant: BAYER INTELLECTUAL PROPERTY GMBH, Monheim (DE)

(72) Inventors: Hartmut Ahrens, Egelsbach (DE); Ralf Braun, Ramberg (DE); Arnim Koehn, Klein-Winternheim (DE); Stefan Lehr, Lyons (FR); Hansjoerg Dietrich, Liederbach (DE); Dirk Schmutzler, Hattersheim (DE); Elmar Gatzweiler, Bad Nauheim (DE); Christopher Hugh Rosinger, Hofheim (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 14/379,528

(22) PCT Filed: Feb. 18, 2013

(86) PCT No.: PCT/EP2013/053176
§ 371 (c)(1),
(2) Date: Aug. 19, 2014

(87) PCT Pub. No.: WO2013/124238
PCT Pub. Date: Aug. 29, 2013

(65) Prior Publication Data
US 2015/0018210 A1    Jan. 15, 2015

(30) Foreign Application Priority Data
Feb. 21, 2012 (EP) .................... 12156307

(51) Int. Cl.
| | | |
|---|---|---|
| A01N 43/713 | (2006.01) | |
| C07D 409/12 | (2006.01) | |
| C07D 411/12 | (2006.01) | |
| C07D 413/12 | (2006.01) | |
| C07D 249/14 | (2006.01) | |
| C07D 257/06 | (2006.01) | |
| C07D 271/08 | (2006.01) | |
| C07D 271/113 | (2006.01) | |
| A01N 25/32 | (2006.01) | |
| A01N 43/653 | (2006.01) | |
| A01N 43/82 | (2006.01) | |
| C07D 271/04 | (2006.01) | |

(52) U.S. Cl.
CPC .............. A01N 43/713 (2013.01); A01N 25/32 (2013.01); A01N 43/653 (2013.01); A01N 43/82 (2013.01); C07D 249/14 (2013.01); C07D 257/06 (2013.01); C07D 271/04 (2013.01); C07D 271/08 (2013.01); C07D 271/113 (2013.01); C07D 409/12 (2013.01); C07D 411/12 (2013.01); C07D 413/12 (2013.01)

(58) Field of Classification Search
CPC .. C07D 271/12; C07D 285/14; C07D 513/04; C07D 498/04; C07D 513/18
USPC ................................ 548/126, 265.4; 504/105
See application file for complete search history.

(56) References Cited

U.S. PATENT DOCUMENTS

| | | | |
|---|---|---|---|
| 2011/0144345 A1* | 6/2011 | Tamai et al. ................... | 546/211 |
| 2011/0152084 A1* | 6/2011 | Kohn et al. .................... | 504/103 |

FOREIGN PATENT DOCUMENTS

| | | |
|---|---|---|
| WO | 2004052849 A1 | 6/2004 |
| WO | 2011035874 A1 | 3/2011 |

OTHER PUBLICATIONS

Reitz, A., U. Ramirez, L. Stith, Y. Du, G. Smith, and E. Jaffe "Pseudomonas aeruginosa porphobilinogen synthase assembly state regulators: hit discovery and initial SAR studies" Arkivoc 2010, 8: pp. 175-188.*
International Search Report from corresponding PCT/EP2013/053176, mailed Apr. 8, 2013.

* cited by examiner

*Primary Examiner* — Nyeemah A Grazier
*Assistant Examiner* — Sagar Patel
(74) *Attorney, Agent, or Firm* — Miles and Stockbridge

(57) ABSTRACT

Sulfinylaminobenzamides of the general formula (I) as herbicides are described.

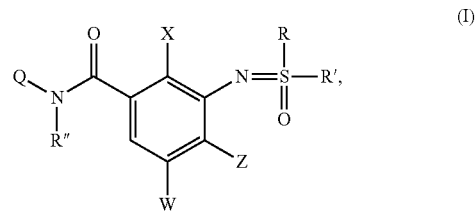

In this formula (I), R, R', R", X, W and Z are radicals such as hydrogen, organic radicals such as alkyl, and other radicals such as halogen. Q is a tetrazolyl, triazolyl or oxadiazolyl radical.

17 Claims, No Drawings

HERBICIDALLY-EFFECTIVE SULFINYL AMINOBENZAMIDES

CROSS REFERENCE TO RELATED APPLICATIONS

This application is a §371 National Stage Application of PCT/EP2013/053176, filed Feb. 18, 2013, which claims priority to EP 12156307.6, filed Feb. 21, 2012.

BACKGROUND

1. Field of the Invention

The invention relates to the technical field of herbicides, especially that of herbicides for selective control of broad-leaved weeds and weed grasses in crops of useful plants.

2. Description of Related Art

WO 2011035874 A1 discloses herbicidally active N-(1,2, 5-oxadiazol-3-yl)benzamides. WO 2004052849 A1 discloses herbicidally active benzoyl derivatives bearing a sulfinylamino group in the 3 position of the phenyl ring. However, the herbicidal activity and/or the crop plant compatibility of the compounds specified in these publications is not always adequate.

SUMMARY

It is an object of the present invention to provide herbicidally active compounds having properties improved over those of the compounds disclosed in the prior art.

It has now been found that particular sulfinylaminobenzamides are of particularly good suitability as herbicides.

The present invention thus provides sulfinylaminobenzamides of the formula (I) or salts thereof

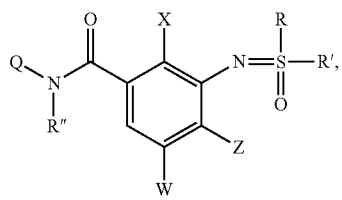
(I)

in which the symbols and indices are each defined as follows:

Q is a Q1, Q2, Q3 or Q4 radical,

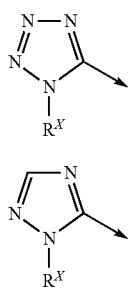
(Q1)

(Q2)

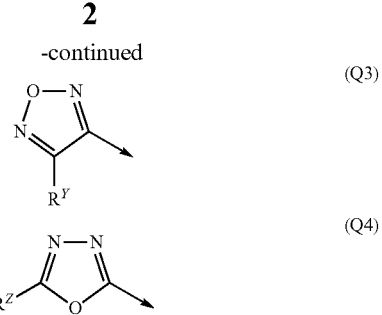
(Q3)

(Q4)

X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1O(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C-(C_1-C_6)$-alkyl, $R^1O(O)C-(C_1-C_6)$-alkyl, $(R^1)_2N(O)C-(C_1-C_6)$-alkyl, $(R^1O)(R^1)N(O)C-(C_1-C_6)$-alkyl, $(R^1)_2N(R^1)N(O)C-(C_1-C_6)$-alkyl, $R^1(O)C(R^1)N(O)C-(C_1-C_6)$-alkyl, $R^2O(O)C(R^1)N(O)C-(C_1-C_6)$-alkyl, $(R^1)_2N(O)C(R^1)N(O)C-(C_1-C_6)$-alkyl, $R^2(O)_2S(R^1)N(O)C-(C_1-C_6)$-alkyl, $R^1O(O)_2S(R^1)N(O)C-(C_1-C_6)$-alkyl, $(R^1)_2N(O)_2S(R^1)N(O)C-(C_1-C_6)$-alkyl, NC-$(C_1-C_6)$-alkyl, $R^1O-(C_1-C_6)$-alkyl, $R^1(O)CO-(C_1-C_6)$-alkyl, $R^2(O)_2SO-(C_1-C_6)$-alkyl, $R^2O(O)CO-(C_1-C_6)$-alkyl, $(R^1)_2N(O)CO-(C_1-C_6)$-alkyl, $(R^1)_2N-(C_1-C_6)$-alkyl, $R^1(O)C(R^1)N-(C_1-C_6)$-alkyl, $R^2(O)_2S(R^1)N-(C_1-C_6)$-alkyl, $R^2O(O)C(R^1)N-(C_1-C_6)$-alkyl, $(R^1)_2N(O)C(R^1)N-(C_1-C_6)$-alkyl, $R^1O(O)_2S(R^1)N-(C_1-C_6)$-alkyl, $(R^1)_2N(O)_2S(R^1)N-(C_1-C_6)$-alkyl, $R^2(O)_nS-(C_1-C_6)$-alkyl, $R^1O(O)_2S-(C_1-C_6)$-alkyl, $(R^1)_2N(O)_2S-(C_1-C_6)$-alkyl, $R^1O(C(R^1)N(O)_2S-(C_1-C_6)$-alkyl, $R^2O(O)C(R^1)N(O)_2S-(C_1-C_6)$-alkyl, $(R^1)_2N(O)C(R^1)N(O)_2S-(C_1-C_6)$-alkyl, $(R^5O)_2(O)P-(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O-(C_1-C_6)$-alkyl, and where heterocyclyl bears n oxo groups, Z is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1O(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C-(C_1-C_6)$-alkyl, $R^1O(O)C-(C_1-C_6)$-alkyl, $(R^1)_2N(O)C-(C_1-C_6)$- alkyl, $(R^1O)(R^1)N(O)C$—$(C_1$-$C_6)$-alkyl, $(R^1)_2N(R^1)N(O)C$—$(C_1$-$C_6)$-alkyl, $R^1O)C(R^1)N(O)C$—$(C_1$-$C_6)$-alkyl, $R^2O(O)C(R^1)N(O)C$—$(C_1$-$C_6)$-alkyl, $(R^1)_2N(O)C(R^1)N(O)C$—$(C_1$-$C_6)$-alkyl, $R^2(O)_2S(R^1)N(O)C$—$(C_1$-$C_6)$-alkyl,
$R^1O(O)_2S(R^1)N(O)C$—$(C_1$-$C_6)$-alkyl, $(R^1)_2N(O)_2S(R^1)N(O)C$—$(C_1$-$C_6)$-alkyl, NC—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^2O(O)CO$—$(C_1$-$C_6)$-alkyl, $(R^1)_2N(O)CO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^1O(O)_2S(R^1)N$—$(C_1$-$C_6)$-alkyl, $(R^1)_2N(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1O)C(R^1)N(O)_2S$—$(C_1$-$C_6)$-alkyl, $R^2O(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, heterocyclyl-$(C_1$-$C_6)$-alkyl, where the six latter radicals are each substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl bears n oxo groups, W is hydrogen, halogen, nitro, cyano, thiocyanato, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_7)$-cycloalkyl, halo-$(C_3$-$C_7)$-cycloalkyl, $(C_1$-$C_6)$-alkoxy, halo-$(C_1$-$C_6)$-alkoxy, $(C_1$-$C_6)$-alkyl-$(O)_nS$—, $(C_1$-$C_6)$-haloalkyl-$(O)_nS$—, $(C_1$-$C_6)$-alkoxy-$(C_1$-$C_4)$-alkyl, $(C_1$-$C_6)$-alkoxy-$(C_1$-$C_4)$-haloalkyl, $R^1(O)C$, $R^1(R^1ON=)C$, $R^1O(O)C$, $(R^1)_2N$, $R^1(O)C(R^1)N$ or $R^2(O)_2S(R^1)N$, R and R' are each independently $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $(C_1$-$C_6)$-alkoxy-$(C_1$-$C_6)$-alkyl, halo-$(C_1$-$C_6)$-alkoxy-$(C_1$-$C_6)$-alkyl, phenyl, heteroaryl or heterocyclyl, where the three latter radicals are each substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl bears n oxo groups, or R and R' together with the sulfur atom to which they are bonded form a 3- to 8-membered unsaturated, semisaturated or saturated ring which contains, apart from the carbon atoms and apart from the sulfur atom of the sulfoximino group, in each case m ring members from the group consisting of $N(R^1)$, O and $S(O)_n$, and where this ring in each case is substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where this ring bears n oxo groups, R" is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, NC—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1O(O)C$, $R^1O(O)C$, $R^1(O)C(R^1)N(O)C$, $R^1O$, $(R^1)_2N$, $R^2O(O)C(R^1)N$, $(R^1)_2N(O)C(R^1)N$, $R^2(O)_2S$, or benzyl substituted in each case by s radicals from the group consisting of methyl, ethyl, methoxy, nitro, trifluoromethyl and halogen, $R^X$ is $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, where the six aforementioned radicals are each substituted by s radicals from the group consisting of nitro, cyano, $(R^6)_3Si$, $(R^5O)_2(O)P$, $R^2(O)_nS$, $(R^1)_2N$, $R^1O$, $R^1(O)C$, $R^1O(O)C$, $R^1(O)CO$, $R^2O(O)CO$, $R^1(O)C(R^1)N$, $R^2(O)_2S(R^1)N$, $(C_3$-$C_6)$-cycloalkyl, heteroaryl, heterocyclyl and phenyl, and where the four latter radicals are substituted by s radicals from the group consisting of $(C_1$-$C_6)$-alkyl, halo-$(C_1$-$C_6)$-alkyl, $(C_1$-$C_6)$-alkoxy, halo-$(C_1$-$C_6)$-alkoxy and halogen, and where heterocyclyl bears n oxo groups, or $R^X$ is $(C_3$-$C_7)$-cycloalkyl, heteroaryl, heterocyclyl or phenyl, where the four aforementioned radicals are each substituted by s radicals from the group consisting of halogen, nitro, cyano, $(C_1$-$C_6)$-alkyl, halo-$(C_1$-$C_6)$-alkyl, $(C_3$-$C_6)$-cycloalkyl, $(C_1$-$C_6)$-alkyl-$S(O)_n$, $(C_1$-$C_6)$-alkoxy, halo-$(C_1$-$C_6)$-alkoxy and $(C_1$-$C_6)$-alkoxy-$(C_1$-$C_4)$-alkyl, $R^Y$ is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_7)$-cycloalkyl, $(C_1$-$C_6)$-alkoxy, halo-$(C_1$-$C_6)$-alkoxy, $(C_2$-$C_6)$-alkenyloxy, $(C_2$-$C_6)$-alkynyloxy, cyano, nitro, methylsulfanyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl each substituted by s radicals from the group consisting of $(C_1$-$C_6)$-alkyl, halo-$(C_1$-$C_6)$-alkyl, $(C_1$-$C_6)$-alkoxy, halo-$(C_1$-$C_6)$-alkoxy and halogen, and where heterocyclyl bears n oxo groups, $R^Z$ is hydrogen, $(C_1$-$C_6)$-alkyl, $R^1O$—$(C_1$-$C_6)$-alkyl, $R^1CH_2$, $(C_3$-$C_7)$-cycloalkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $R^1O$, $R^1(H)N$, methoxycarbonyl, ethoxycarbonyl, methylcarbonyl, dimethylamino, trifluoromethylcarbonyl, acetylamino, methylsulfanyl, methylsulfinyl, methylsulfonyl, or heteroaryl, heterocyclyl, benzyl oder phenyl each substituted by s radicals from the group consisting of halogen, nitro, cyano, $(C_1$-$C_6)$-alkyl, halo-$(C_1$-$C_6)$-alkyl, $(C_3$-$C_6)$-cycloalkyl, $(C_1$-$C_6)$-alkyl-$S(O)_n$, $(C_1$-$C_6)$-alkoxy, halo-$(C_1$-$C_6)$-alkoxy and $(C_1$-$C_6)$-alkoxy-$(C_1$-$C_4)$-alkyl, where heterocyclyl bears n oxo groups, $R^1$ is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, $(C_3$-$C_6)$-cycloalkenyl, halo-$(C_3$-$C_6)$-cycloalkyl, $(C_3$-$C_6)$-cycloalkyl-$(C_1$-$C_6)$-alkyl, $(C_1$-$C_6)$-alkyl-O—$(C_1$-$C_6)$-alkyl, cycloalkyl-$(C_1$-$C_6)$-alkyl-O—$(C_1$-$C_6)$-alkyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl, heterocyclyl-O—$(C_1$-$C_6)$-alkyl, phenyl-$N(R^3)$—$(C_1$-$C_6)$-alkyl, heteroaryl-$N(R^3)$—$(C_1$-$C_6)$-alkyl, heterocyclyl-$N(R^3)$—$(C_1$-$C_6)$-alkyl, phenyl-$S(O)_n$—$(C_1$-$C_6)$-alkyl, heteroaryl-$S(O)_n$—$(C_1$-$C_6)$-alkyl, heterocyclyl-$S(O)_n$—$(C_1$-$C_6)$-alkyl, where the fifteen latter radicals are each substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1$-$C_6)$-alkyl, and where heterocyclyl bears n oxo groups, $R^2$ is $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, $(C_3$-$C_6)$-cycloalkenyl, halo-$(C_3$-

$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, heterocyclyl-O—($C_1$-$C_6$)-alkyl, phenyl-N($R^3$)—($C_1$-$C_6$)-alkyl, heteroaryl-N($R^3$)—($C_1$-$C_6$)-alkyl, heterocyclyl-N($R^3$)—($C_1$-$C_6$)-alkyl, phenyl-S(O)$_n$—($C_1$-$C_6$)-alkyl, heteroaryl-S(O)$_n$—($C_1$-$C_6$)-alkyl, heterocyclyl-S(O)$_n$—($C_1$-$C_6$)-alkyl, where the fifteen latter radicals are each substituted by s radicals from the group consisting of nitro, halogen, cyano, thiocyanato, ($C_1$-$C_6$)-alkyl, halo-($C_1$-$C_6$)-alkyl, ($C_3$-$C_6$)-cycloalkyl, $R^3$O(O)C, ($R^3$)$_2$N(O)C, $R^3$O, ($R^3$)$_2$N, $R^4$(O)$_n$S, $R^3$O(O)$_2$S, ($R^3$)$_2$N(O)$_2$S and $R^3$O—($C_1$-$C_6$)-alkyl, and where heterocyclyl bears n oxo groups, $R^3$ is hydrogen, ($C_1$-$C_6$)-alkyl, halo-($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl or phenyl, $R^4$ is ($C_1$-$C_6$)-alkyl, halo-($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl or phenyl, $R^5$ is hydrogen or ($C_1$-$C_4$)-alkyl, $R^6$ is ($C_1$-$C_4$)-alkyl, $R^7$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, ($C_3$-$C_6$)-cycloalkyl, or heteroaryl or heterocyclyl each substituted by s radicals from the group consisting of methyl, ethyl, methoxy, trifluoromethyl and halogen;

n is 0, 1 or 2, m is 0, 1, 2, 3 or 4, s is 0, 1, 2 or 3.

DETAILED DESCRIPTION OF A PREFERED EMBODIMENT

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned. This applies analogously to the formation of ring systems by various atoms and elements. At the same time, the scope of the claims shall exclude those compounds known to the person skilled in the art to be chemically unstable under standard conditions.

Depending on the nature and the attachment of the substituents, the compounds of the general formula (I) may be present as stereoisomers. If, for example, one or more asymmetrically substituted carbon atoms are present, there may be enantiomers and diastereomers. There are likewise stereoisomers when n in the S(O)$_n$ moiety is 1. There are likewise stereoisomers when the R and R' radicals are defined differently. Stereoisomers can be obtained from the mixtures prepared by customary separation methods, for example by chromatographic separation processes. It is equally possible to selectively prepare stereoisomers by using stereoselective reactions using optically active starting materials and/or auxiliaries. The invention also relates to all stereoisomers and mixtures thereof which are encompassed by the general formula (I) but not defined specifically.

The compounds of the formula (I) are capable of forming salts. Salts can be formed by the action of a base on those compounds of the formula (I) which bear an acidic hydrogen atom, for example in the case of R. Suitable bases are, for example, organic amines such as trialkylamines, morpholine, piperidine or pyridine, and also ammonium, alkali metal or alkaline earth metal hydroxides, carbonates and hydrogencarbonates, especially sodium and potassium hydroxide, sodium and potassium carbonate and sodium and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR*RR*]$^+$ in which R, R*, R and R* are each independently an organic radical, especially alkyl, aryl, aralkyl or alkylaryl. Also useful are alkylsulfonium and alkylsulfoxonium salts, such as ($C_1$-$C_4$)-trialkylsulfonium and ($C_1$-$C_4$)-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid, or sulfonic acids, for example p-toluenesulfonic acid, onto a basic group, for example amino, alkylamino, dialkylamino, piperidino, morpholino or pyridino. These salts then contain the conjugate base of the acid as the anion.

Preference is given to compounds of the general formula (I) in which

Q is a Q1, Q2, Q3 or Q4 radical, (Q1)

(Q2)

(Q3)

(Q4)

X is nitro, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by s radicals from the group consisting of nitro, halogen, cyano, thiocyanato, $(C_1-C_6)$-alkyl, halo-$(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, Z is hydrogen, nitro, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by s radicals from the group consisting of nitro, halogen, cyano, thiocyanato, $(C_1-C_6)$-alkyl, halo-$(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, W is hydrogen, halogen, nitro, cyano, $(C_1-C_6)$-alkyl, halo-$(C_1-C_6)$-alkyl, $(C_3-C_7)$-cycloalkyl, $(C_1-C_6)$-alkoxy, $(C_1-C_6)$-alkyl-$(O)_nS$—, $R^1O(O)C$, $(R^1)_2N$, $R^1(O)C(R^1)N$ or $R^2(O)_2S(R^1)N$, R and R' are each independently $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $(C_1-C_6)$-alkoxy-$(C_1-C_6)$-alkyl, halo-$(C_1-C_6)$-alkoxy-$(C_1-C_6)$-alkyl, phenyl, heteroaryl oder heterocyclyl, where the three latter radicals are each substituted by s radicals from the group consisting of nitro, halogen, $(C_1-C_6)$-alkyl, halo-$(C_1-C_6)$-alkyl, $R^1O(O)C$, $(R^1)_2N(O)C$, $R^1O$, $(R^1)_2N$, $R^2(O)_nS$ and $R^1O$—$(C_1-C_6)$-alkyl, and where heterocyclyl bears n oxo groups, or R and R' together with the sulfur atom to which they are bonded form a 3- to 8-membered unsaturated, semisaturated or saturated ring which contains, apart from the carbon atoms and apart from the sulfur atom of the sulfoximino group, in each case m ring members from the group consisting of $N(R^1)$, O and $S(O)_n$, and where this ring in each case is substituted by s radicals from the group consisting of halogen, $(C_1-C_6)$-alkyl, halo-$(C_1-C_6)$-alkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where this ring bears n oxo groups, R" is hydrogen, $R^X$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, where the six aforementioned radicals are each substituted by s radicals from the group consisting of $R^2(O)_nS$, $(R^1)_2N$, $R^1O$, $R^1(O)C$, $R^1O(O)C$, $R^1(O)CO$, $R^2O(O)CO$, $R^1(O)C(R^1)N$, $R^2(O)_2S(R^1)N$, $(C_3-C_6)$-cycloalkyl, heteroaryl, heterocyclyl and phenyl, where the four latter radicals themselves are in turn substituted by s radicals from the group consisting of $(C_1-C_6)$-alkyl, halo-$(C_1-C_6)$-alkyl, $(C_1-C_6)$-alkoxy and halogen, and where heterocyclyl bears n oxo groups, or $R^X$ is $(C_3-C_7)$-cycloalkyl, where this radical in each case is substituted by s radicals from the group consisting of halogen, $(C_1-C_6)$-alkyl and halo-$(C_1-C_6)$-alkyl, $R^Y$ is hydrogen, $(C_1-C_6)$-alkyl, halo-$(C_1-C_6)$-alkyl, $(C_3-C_7)$-cycloalkyl, $(C_1-C_6)$-alkoxy, methoxycarbonyl, methoxycarbonylmethyl, halogen, amino, aminocarbonyl or methoxymethyl, $R^Z$ is hydrogen, $(C_1-C_6)$-alkyl, $R^1O$—$(C_1-C_6)$-alkyl, $R^1CH_2$, $(C_3-C_7)$-cycloalkyl, halo-$(C_1-C_6)$-alkyl, $R^1O$, $R^1(H)N$, methoxycarbonyl, acetylamino or methylsulfonyl, $R^1$ is hydrogen, $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, where the nine latter radicals are each substituted by s radicals from the group consisting of nitro, halogen, $(C_1-C_6)$-alkyl, halo-$(C_1-C_6)$-alkyl, $R^3O(O)C$, $(R^3)_2N(O)C$, $R^3O$, $(R^3)_2N$, $R^4(O)_nS$ and $R^3O$—$(C_1-C_6)$-alkyl, and where heterocyclyl bears n oxo groups, $R^2$ is $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, where the nine latter radicals are each substituted by s radicals from the group consisting of nitro, halogen, $(C_1-C_6)$-alkyl, halo-$(C_1-C_6)$-alkyl, $R^3O(O)C$, $(R^3)_2N(O)C$, $R^3O$, $(R^3)_2N$, $R^4(O)_nS$ and $R^3O$—$(C_1-C_6)$-alkyl, and where heterocyclyl bears n oxo groups, $R^3$ is hydrogen or $(C_1-C_6)$-alkyl, $R^4$ is $(C_1-C_6)$-alkyl, $R^5$ is hydrogen or $(C_1-C_4)$-alkyl, $R^7$ is acetoxy, acetamido, methoxycarbonyl or $(C_3-C_6)$-cycloalkyl, n is 0, 1 or 2, m is 0, 1 or 2, s is 0, 1, 2 or 3.

Particular preference is given to compounds of the general formula (I) in which Q is a Q1, Q2, Q3 or Q4 radical,

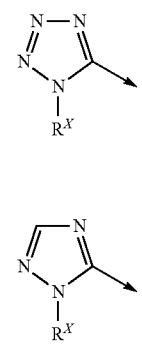

(Q1)

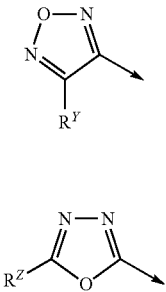

(Q2)

(Q3)

(Q4)

X is nitro, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, hydroxycarbonyl, methoxycarbonyl, ethoxycarbonyl, methoxy, ethoxy, methylsulfanyl, methylsulfinyl, methylsulfonyl, methoxymethyl, ethoxymethyl, methoxyethyl, methoxyethoxymethyl, methylthiomethyl, methylsulfinylmethyl or methylsulfonylmethyl, Z is hydrogen, nitro, cyano, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, hydroxycarbonyl, methoxycarbonyl, ethoxycarbonyl, methoxy, ethoxy, methylsulfanyl, methylsulfinyl or methylsulfonyl, W is hydrogen, chlorine or methyl, R and R' are each independently methyl, ethyl or n-propyl, or R and R' together with the sulfur atom to which they are bonded form a 5- or 6-membered saturated ring which, apart from the carbon atoms and apart from the sulfur atom of the sulfoximino group, contains m oxygen atoms, R" is hydrogen, $R^X$ is methyl, ethyl, n-propyl, prop-2-en-1-yl, methoxyethyl, ethoxyethyl or methoxyethoxyethyl, $R^Y$ is methyl, ethyl, n-propyl, chlorine or amino, $R^Z$ is methyl, ethyl, n-propyl or methoxymethyl, m is 0 or 1.

Inventive compounds in which Q is Q1 or Q2 can be prepared, for example, by the method shown in scheme 1, by base-catalyzed reaction of a benzoyl chloride (II) with a 5-amino-1H-1,2,4-triazole or 5-amino-1H-tetrazole (III):

Scheme 1

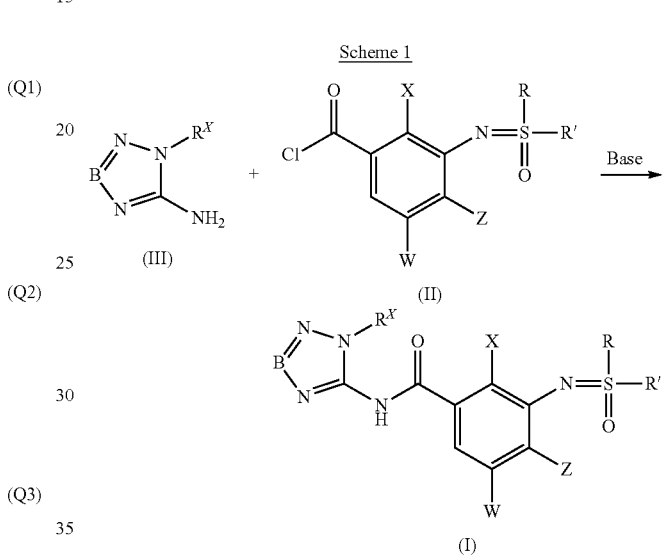

B therein is CH or N.

The benzoyl chlorides of the formula (II) or their parent benzoic acids are known in principle and can be prepared, for example, by the methods described in WO 2004052849 A1, WO 2008035737 A1, WO 2009116290 A1, WO 2010016230 A1 and US 20110144345 A1.

Inventive compounds in which Q is Q1 or Q2 can also be prepared by the method shown in scheme 2, by reaction of a benzoic acid of the formula (IV) with a 5-amino-1H-1,2,4-triazole or 5-amino-1H-tetrazole (III):

Scheme 2

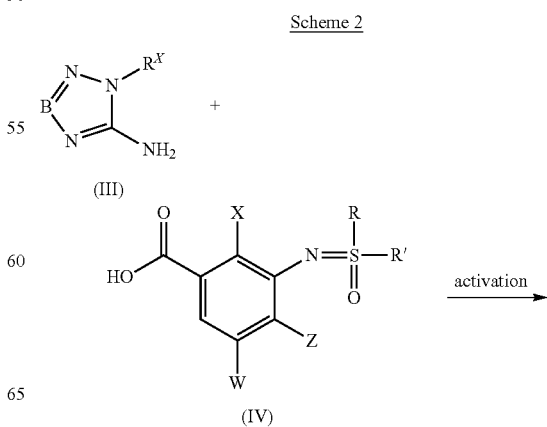

-continued

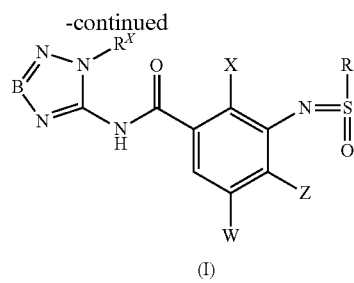
(I)

For the activation, it is possible to use dehydrating reagents which are typically used for amidation reactions, for example 1,1'-carbonyldiimidazole (CD), dicyclohexylcarbodiimide (DCC), 2,4,6-tripropyl-1,3,5,2,4,6-trioxatriphosphinane 2,4,6-trioxide (T3P).

Inventive compounds in which Q is Q1 or Q2 can also be prepared by the method shown in scheme 3, by conversion of an N-(1H-1,2,4-triazol-5-yl)benzamide or of an N-(1H-tetrazol-5-yl)benzamide:

Scheme 3

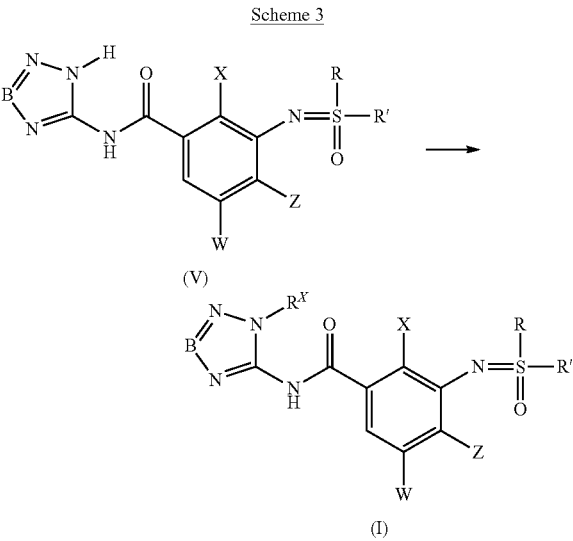

For this reaction shown in scheme 3, it is possible to use alkylating agents such as alkyl halides or sulfonates or dialkyl sulfates, in the presence of a base.

The 5-amino-1H-tetrazoles of the formula (III) are either commercially available or can be prepared analogously to methods known from the literature. For example, substituted 5-aminotetrazoles can be prepared from aminotetrazole by the method described in Journal of the American Chemical Society (1954), 76, 923-924:

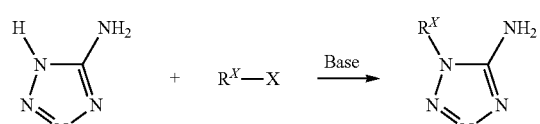

In the above reaction, X is a leaving group such as iodine. Substituted 5-aminotetrazoles can also be synthesized, for example, as described in Journal of the American Chemical Society (1954) 76, 88-89:

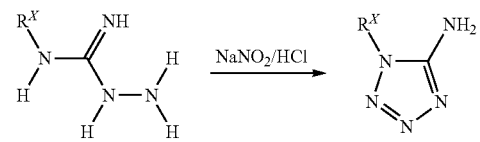

The 5-amino-1H-triazoles of the formula (III) are either commercially available or can be prepared analogously to methods known from the literature. For example, substituted 5-aminotriazoles can be prepared from aminotriazole by the method described in Zeitschrift für Chemie (1990), 30(12), 436-437:

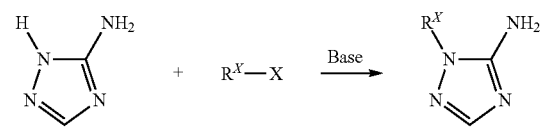

Substituted 5-aminotriazoles can also be synthesized, for example, as described in Chemische Berichte (1964), 97(2), 396-404:

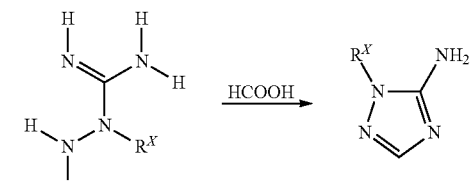

Substituted 5-aminotriazoles can also be synthesized, for example, as described in Angewandte Chemie (1963), 75, 918:

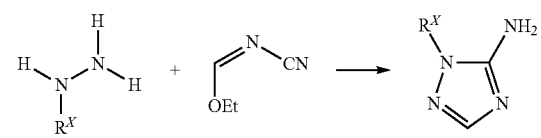

Inventive compounds in which Q is Q3 can be prepared, for example, by the method shown in scheme 4, by base-catalyzed reaction of a benzoyl chloride (II) with a 4-amino-1,2,5-oxadiazole (VI):

Scheme 4

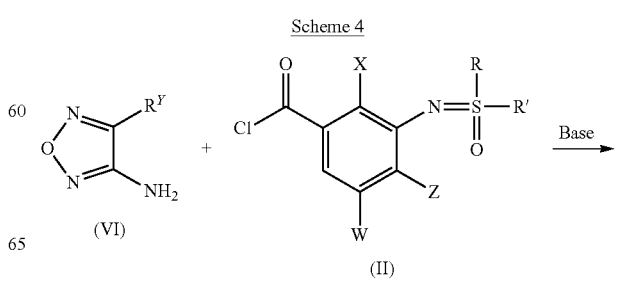

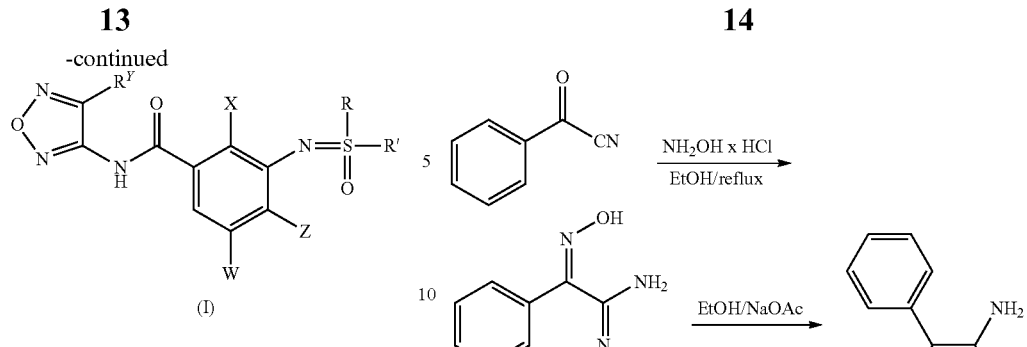

Inventive compounds can also be prepared by the method described in scheme 5, by reacting a benzoic acid of the formula (IV) with a 4-amino-1,2,5-oxadiazole (VI):

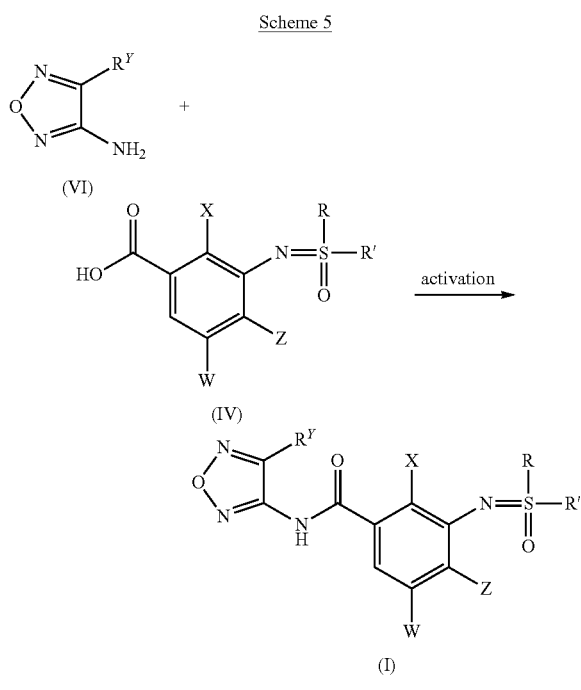

For the activation, it is possible to use dehydrating reagents which are typically used for amidation reactions, for example 1,1'-carbonyldiimidazole (CD), dicyclohexylcarbodiimide (DCC), 2,4,6-tripropyl-1,3,5,2,4,6-trioxatriphosphinane 2,4,6-trioxide (T3P) etc.

The 4-amino-1,2,5-oxadiazoles of the formula (VI) are either commercially available or known, or can be prepared analogously to methods known from the literature. For example, 3-alkyl-4-amino-1,2,5-oxadiazoles can be prepared from β-keto esters by the method described in Russian Chemical Bulletin, Int. Ed., vol. 54, 4, p. 1032-1037 (2005):

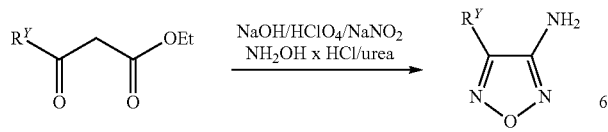

3-Aryl-4-amino-1,2,5-oxadiazoles can be synthesized, for example, as described in Russian Chemical Bulletin, 54(4), 1057-1059, (2005) or Indian Journal of Chemistry, Section B: Organic Chemistry Including Medicinal Chemistry, 26B(7), 690-2, (1987):

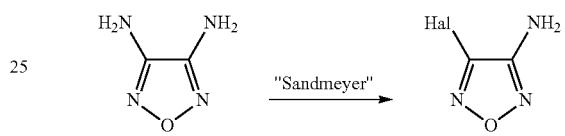

3-Amino-4-halo-1,2,5-oxadiazoles can be prepared, for example, by a Sandmeyer reaction from the commercially available 3,4-diamino-1,2,5-oxadiazole, according to the method described in Heteroatom Chemistry 15(3), 199-207 (2004):

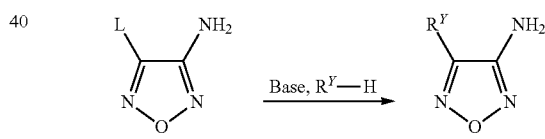

Nucleophilic $R^Y$ radicals can be introduced into 3-amino-1,2,5-oxadiazoles by substitution of the leaving group L as described in Journal of Chemical Research, Synopses, (6), 190, 1985 or in Izvestiya Akademii Nauk SSSR, Seriya Khimicheskaya, (9), 2086-8, 1986 or in Russian Chemical Bulletin (Translation of Izvestiya Akademii Nauk, Seriya Khimicheskaya), 53(3), 596-614, 2004. L is a leaving group, for example chlorine, bromine, iodine, mesyloxy, tosyloxy, trifluorosulfonyloxy, etc.

Inventive compounds in which Q is Q4 can be prepared, for example, by the method shown in scheme 6, by base-catalyzed reaction of a benzoyl chloride (II) with a 2-amino-1,3,4-oxadiazole (VII):

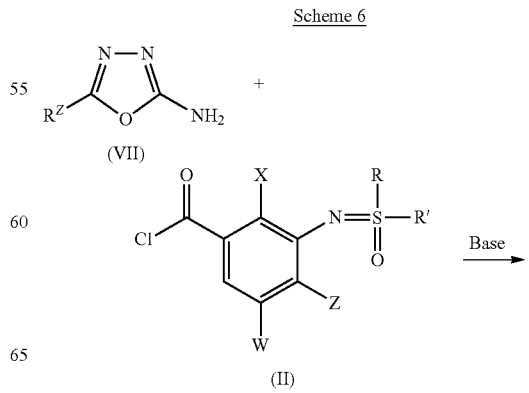

-continued

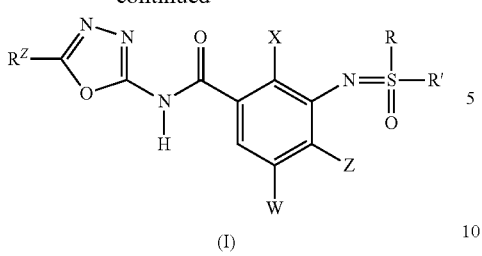

(I)

Inventive compounds can also be prepared by the method described in scheme 7, by reacting a benzoic acid of the formula (IV) with a 2-amino-1,3,4-oxadiazole (VII):

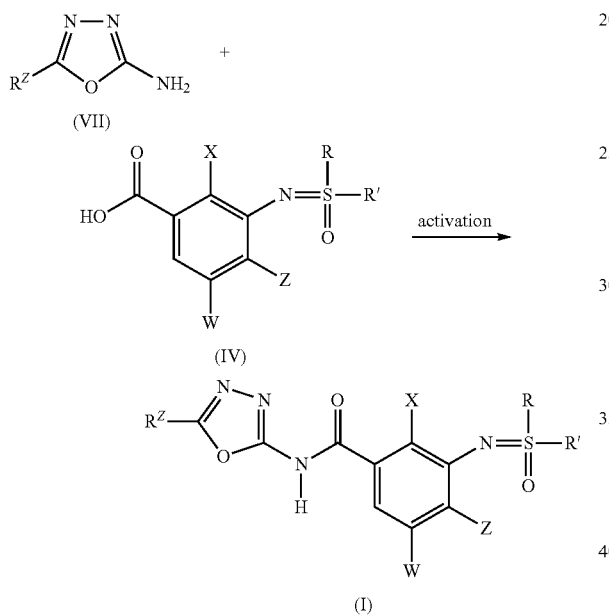

For the activation, it is possible to use dehydrating reagents which are typically used for amidation reactions, for example 1,1'-carbonyldiimidazole (CD), dicyclohexylcarbodiimide (DCC), 2,4,6-tripropyl-1,3,5,2,4,6-trioxatriphosphinane 2,4,6-trioxide (T3P) etc.

Inventive compounds can also be prepared by the method described in scheme 8, by cyclizing a compound of the formula VIII:

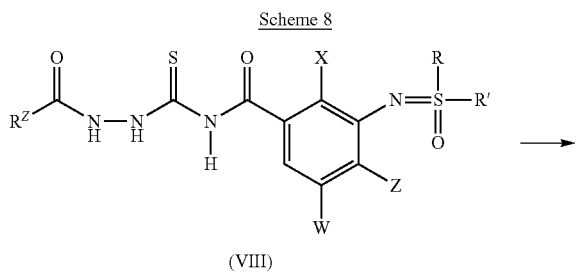

-continued

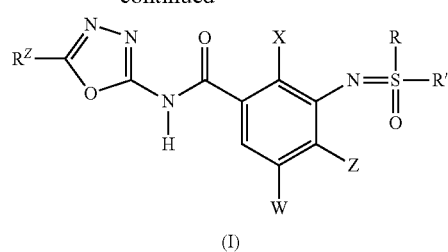

(I)

The cyclization can be performed by the methods described in Synth. Commun. 31 (12), 1907-1912 (2001) or in Indian J. Chem., Section B: Organic Chemistry Including Medicinal Chemistry; Vol. 43 (10), 2170-2174 (2004).

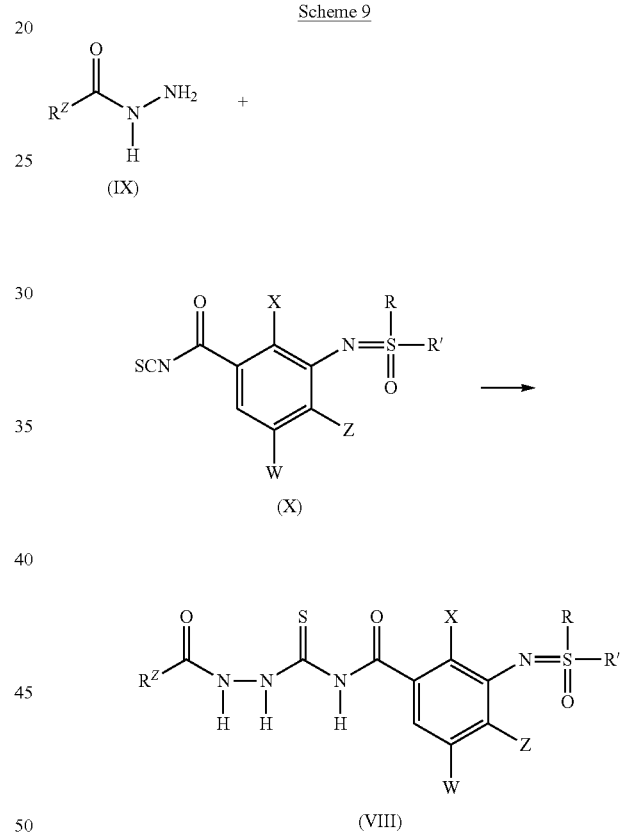

The compound of the formula (VIII) used in scheme 8 can be prepared by reaction of an acyl isothiocyanate of the formula (X) with a hydrazide of the formula (IX) by the method described in Synth. Commun. 25(12), 1885-1892 (1995).

Inventive compounds in which the substituent R" is not hydrogen can be prepared, for example, according to the method shown in scheme 10, by reacting an N-(1,2,5-oxadiazol-3-yl)-, N-(1,3,4-oxadiazol-2-yl)-, N-(tetrazol-5-yl)- or N-(triazol-5-yl)arylcarboxamide (I) with a compound of the general formula (XI) where L is a leaving group, for example chlorine, bromine, iodine, mesyloxy, tosyloxy, trifluorosulfonyloxy, etc.:

Scheme 10

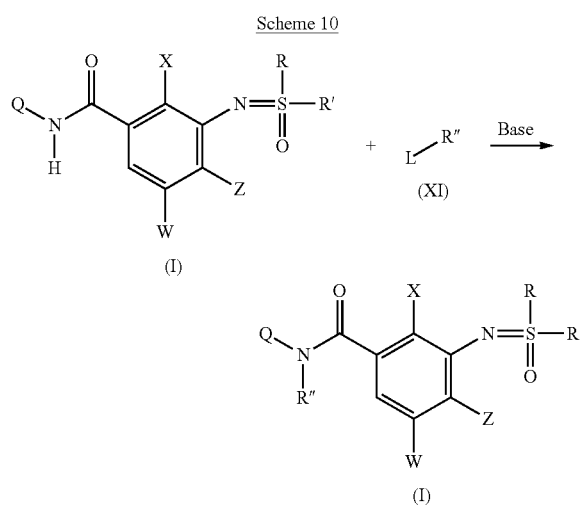

The compounds of the formula (XI) are either commercially available or can be prepared by known methods described in the literature.

Inventive compounds can also be prepared according to the method shown in scheme 11 by reaction of an amine of the formula (XII) with an acid chloride (II), as described, for example, in J. Het. Chem. (1972), 9 (1), 107-109:

Scheme 11

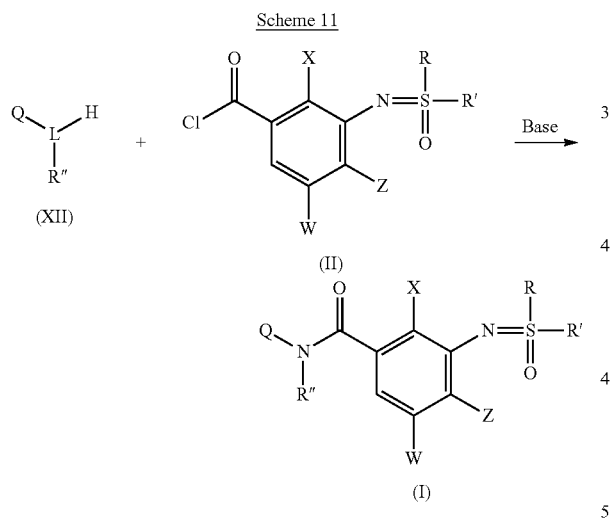

Inventive compounds can also be prepared according to the method shown in scheme 12, by reaction of an amine of the formula (XII) with an acid of the formula (IV):

Scheme 12

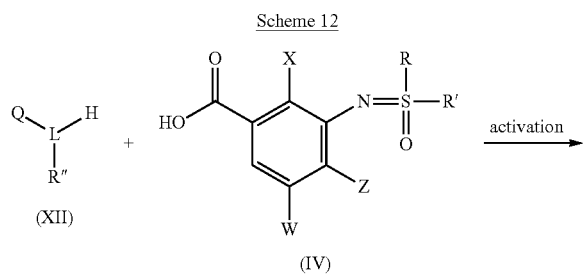

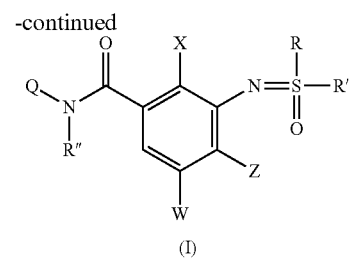

For the activation, it is possible to use dehydrating reagents which are typically used for amidation reactions, for example 1,1'-carbonyldiimidazole (CD), dicyclohexylcarbodiimide (DCC), 2,4,6-tripropyl-1,3,5,2,4,6-trioxatriphosphinane 2,4,6-trioxide (T3P) etc.

The amines of the formula (XII) are either commercially available or known in the literature or can be prepared, for example, by the methods described in scheme 13, by base-catalyzed alkylation or by reductive amination, or according to the method described in scheme 14, by nucleophilic substitution of a leaving group L by amines R"—$NH_2$, where L is a leaving group, for example chlorine, bromine, iodine, mesyloxy, tosyloxy, trifluorosulfonyloxy, etc.

Scheme 13

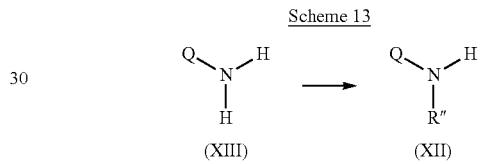

Scheme 14

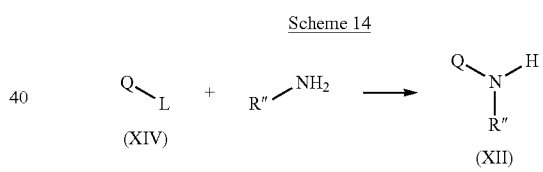

The amines of the formula (XII) can also be prepared by cyclization reactions as described, for example, in J. Org. Chem. 73(10), 3738-3744 (2008) where Q=Q1, or in Buletinul Institutului Politehnic din Iasi (1974), 20(1-2), 95-99 or in J. Org. Chem. 67(21), 7361-7364 (2002) where Q=Q4.

It may be appropriate to alter the sequence of reaction steps. For instance, benzoic acids bearing a sulfoxide cannot be converted directly to their acid chlorides. Here, it is advisable to prepare initially, at the thioether stage, the amide and then to oxidize the thioether to the sulfoxide. It is possibly advantageous not to generate the sulfoximine until the end of the synthesis sequence, at the benzamide stage.

The workup of the respective reaction mixtures is generally effected by known processes, for example by crystallization, aqueous-extractive workup, by chromatographic methods or by a combination of these methods.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Either on a solid phase or in the liquid phase, the performance of single or multiple synthesis steps can be supported by the use of microwave technology. The specialist literature describes a series of experimental protocols, for example in Microwaves in Organic and Medicinal Chemistry (editor C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), collectively referred to hereinafter as "inventive compounds", have excellent herbicidal efficacy against a broad spectrum of economically important monocotyledonous and dicotyledonous annual weed plants. The active ingredients also have good control over perennial weed plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the inventive compounds are applied to the soil surface before germination, either the weed seedlings are prevented completely from emerging or the weeds grow until they have reached the cotyledon stage, but then stop growing and, eventually, after three to four weeks have passed, die completely.

If the active ingredients are applied post-emergence to the green parts of the plants, there is likewise stoppage of growth after the treatment, and the weed plants remain at the growth stage of the time of application, or they die completely after a certain time, such that competition by the weeds, which is harmful to the crop plants, is thus eliminated very early and in a lasting manner.

Although the inventive compounds have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, especially *Zea* and *Triticum*, are damaged only to an insignificant extent, if at all, depending on the structure of the respective inventive compound and the application rate thereof. For these reasons, the present compounds are very suitable for the selective control of unwanted plant growth in plant crops such as agriculturally useful plants or ornamentals.

In addition, the inventive compounds (depending on their particular structure and the application rate deployed) have outstanding growth-regulating properties in crop plants. They intervene in the plant's own metabolism with a regulatory effect, and can thus be used to control plant constituents and to facilitate harvesting, for example by triggering desiccation and stunted growth. In addition, they are also suitable for the general control and inhibition of unwanted vegetative growth without killing the plants. Inhibiting vegetative growth plays a major role for many monocotyledonous and dicotyledonous crops, since, for example, this can reduce or completely prevent lodging.

By virtue of their herbicidal and plant-growth-regulating properties, the active ingredients can also be used for controlling harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

Preference is given to the use of the inventive compounds or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the inventive compounds can be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

recombinant modifications of crop plants for the purpose of modifying the starch synthesized in the plants (e.g. WO 9211376, WO 9214827, WO 9119806), transgenic crop plants which are resistant to particular herbicides of the glufosinate type (cf., for example, EP-A-0242236, EP-A-242246) or glyphosate type (WO 9200377) or of the sulfonylurea type (EP-A-0257993, US-A-5013659), transgenic crop plants, for example cotton, with the ability to produce *Bacillus thuringiensis* toxins (Bt toxins) which make the plants resistant to particular pests (EP-A-0142924, EP-A-0193259), transgenic crop plants with a modified fatty acid composition (WO 9113972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.), Gene Transfer to Plants, Springer Lab Manual (1995), Springer Verlag Berlin, Heidelberg or Christou, "Trends in Plant Science" 1 (1996) 423-431).

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product. To this end, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

For instance, it is possible to obtain transgenic plants whose properties are altered by overexpression, suppression or inhibition of homologous (=natural) genes or gene sequences, or expression of heterologous (=foreign) genes or gene sequences.

Preferably, the inventive compounds can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the inventive active ingredients in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds as herbicides for control of weed plants in transgenic crop plants.

The inventive compounds can be applied in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], volume 7, C. Hanser Verlag Munich, 4th edition 1986, Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may be, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granulated inert material or by applying active ingredient concentrates by means of adhesives, for example polyvinyl alcohol, sodium polyacrylate or mineral oils, to the surface of carrier substances, such as sand, kaolinites or granulated inert material. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active ingredient concentration is, for example, about 10 to 90% by weight, the remainder to 100% consisting of customary formulation constituents. In emulsifiable concentrates, the active ingredient concentration may be about 1 to 90% and preferably 5 to 80% by weight. Dust-type formulations contain 1 to 30% by weight of active ingredient, preferably usually 5 to 20% by weight of active ingredient; sprayable solutions contain about 0.05 to 80, preferably 2 to 50, % by weight of active ingredient. In the case of water-dispersible granules, the active ingredient content depends partly on whether the active compound is present in liquid or solid form and on which granulation assistants, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 14th edition, The British Crop Protection Council and the Royal Soc. of Chemistry, 2003 and literature cited therein.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It may vary within wide limits, for example between 0.001 and 1.0 kg/ha or more of active substance; however, preferably it is between 0.005 and 750 g/ha.

The examples which follow illustrate the invention.

A. CHEMICAL EXAMPLES

Synthesis of 2,4-dichloro-3-{[diethyl(oxido)-λ4-sulfanylidene]amino}-N-(1-methyltetrazol-5-yl)benzamide (table example no. 1-14)

Step 1: Synthesis of methyl 2,4-dichloro-3-(nonafluoro-n-butylsulfonyloxy)benzoate 9.5 g (43.0 mmol) of methyl 2,4-dichloro-3-hydroxybenzoate in 240 ml of acetonitrile were admixed with 8.6 g (62.2 mmol) of potassium carbonate and then with 9.5 ml (52.8 mmol) of nonafluoro-n-butanesulfonyl chloride. The reaction mixture was stirred at room temperature (RT) for 16 h. For workup, the contents were poured onto ice-water and the mixture was extracted with ethyl acetate. The organic phase was dried and the filtrate was freed of the solvent on a rotary evaporator. The residue was purified by chromatography, which gave 3.5 g of clean product.

Step 2: Synthesis of methyl 2,4-dichloro-3-{[diethyl(oxido)-λ4-sulfanylidene]amino}benzoate 9.5 g (18.9 mmol) of methyl 2,4-dichloro-3-(nonafluoro-n-butylsulfonyloxy)benzoate were dissolved in 100 ml of toluene. The solution was purged with nitrogen under a nitrogen atmosphere for 5-10 minutes. Subsequently, 2.83 g (23.3 mmol) of S,S-diethylsulfoximine, 0.19 g (0.846 mmol) of palladium(II) acetate, 0.84 g (1.35 mmol) of (+/−)-2,2'-bis(diphenylphosphino)-1,1'-binaphthyl and 9.8 g (30.1 mmol) of cesium carbonate were added successively. Subsequently, the mixture was purged with nitrogen once again for 15-20 minutes. The reaction mixture was heated under reflux for 4 h. For workup, the contents were cooled to RT and poured onto ice-water, and then the mixture was extracted with ethyl acetate. The organic phase was dried and distilled under reduced pressure. The crude product obtained was purified by chromatography, which gave 4.5 g of isolated clean product.

Step 3: Synthesis of 2,4-dichloro-3-{[diethyl(oxido)-λ4-sulfanylidene]amino}benzoic acid 4.5 g (13.9 mmol) of methyl 2,4-dichloro-3-{[diethyl(oxido)-λ4-sulfanylidene]amino}benzoate were dissolved in 160 ml of ethanol. Subsequently, 16.8 ml (42 mmol) of a 10% aqueous sodium hydroxide solution were added dropwise. The contents were then stirred at RT for 3 h. For workup, the ethanol was removed under reduced pressure on a rotary evaporator. The residue was admixed with water and the mixture was washed with diethyl ether. The aqueous phase was acidified with concentrated hydrochloric acid and extracted with ethyl acetate. The organic phase was dried and the filtrate was freed of the solvent on a rotary evaporator. 3.5 g of the product were isolated as the residue.

Step 4: Synthesis of 2,4-dichloro-3-{[diethyl(oxido)-λ4-sulfanylidene]amino}-N-(1-methyltetrazol-5-yl)benzamide 250 mg (0.81 mmol) of 2,4-dichloro-3-{[diethyl(oxido)-λ4-sulfanylidene]amino}benzoic acid and 112 mg (1.13 mmol) of 5-amino-1-methyl-1H-tetrazole in 7.5 ml of pyridine were admixed with 133 mg (1.05 mmol) of oxalyl chloride and then stirred at RT for three days. For workup, the mixture was concentrated and the residue was stirred with $CH_2Cl_2$ and a saturated aqueous sodium hydrogencarbonate solution. The organic phase was concentrated again and the residue was purified by chromatography, which gave 170 mg of clean product.

Syntheses of 2,4-dichloro-3-[(4-oxido-1,4-λ4-oxathian-4-ylidene)amino]-N-(4-methyl-1,2,5-oxadiazol-3-yl)benzamide (table example no. 6-102)

Step 1: Synthesis of methyl 2,4-dichloro-3-[(4-oxido-1,4-λ4-oxathian-4-ylidene)amino]benzoate 5 g (9.94 mmol) of methyl 2,4-dichloro-3-(nonafluoro-n-butylsulfonyloxy)benzoate were dissolved in 100 ml of toluene. The solution was purged with nitrogen under a nitrogen atmosphere for 5-10 minutes. Subsequently, 1.6 g (11.9 mmol) of 2H-4λ4-1,4-oxathiin-4-imine 4-oxide, 0.1 g (0.46 mmol) of palladium(II) acetate, 0.43 g (0.7 mmol) of (+/−)-2,2'-bis(diphenylphosphino)-1,1'-binaphthyl and 4.8 g (14 mmol) of cesium carbonate were added successively. Subsequently, the mixture was purged with nitrogen once again for 15-20 minutes. The reaction mixture was heated under reflux for 4 h. For workup, the contents were cooled to RT and poured onto ice-water, and then the mixture was extracted with CH$_2$Cl$_2$. The organic phase was dried and distilled under reduced pressure. The crude product obtained was purified by chromatography, which gave 1.8 g of clean product.

Step 2: Synthesis of 2,4-dichloro-3-[(4-oxido-1,4-λ4-oxathian-4-ylidene)amino]benzoic acid 1.8 g (5.32 mmol) of methyl 2,4-dichloro-3-[(4-oxido-1,4-λ4-oxathian-4-yliden)amino]benzoate were dissolved in 40 ml of methanol. Subsequently, 31 ml (77.5 mmol) of a 10% aqueous sodium hydroxide solution were added. The contents were then stirred at RT for 1 h. For workup, the methanol was removed under reduced pressure on a rotary evaporator. The residue was admixed with water and the mixture was washed with diethyl ether. The aqueous phase was acidified with 1M hydrochloric acid and extracted with ethyl acetate. The organic phase was dried and the filtrate was freed of the solvent on a rotary evaporator. 1.2 g of the product were isolated as the residue.

Step 3: Syntheses of 2,4-dichloro-3-[(4-oxido-1,4-λ4-oxathian-4-ylidene)amino]-N-(4-methyl-1,2,5-oxadiazol-3-yl)benzamide 200 mg (0.62 mmol) of 2,4-dichloro-3-[(4-oxido-1,4-λ4-oxathian-4-ylidene)amino]benzoic acid and 67.2 mg (0.68 mmol) of 4-methyl-1,2,5-oxadiazol-3-yl-amine in 15 ml of CH$_2$Cl$_2$ were admixed with 589 mg (0.93 mmol; 50% solution in THF) of 2,4,6-tripropyl-1,3,5,2,4,6-trioxatriphosphinane 2,4,6-trioxide. The mixture was stirred at RT for 1 h. Subsequently, 312 mg (3.09 mmol) of NEt$_3$ were added dropwise, then a catalytic amount of 4-(dimethylamino)pyridine. The contents were stirred at RT for three days. For workup, the mixture was washed with 1M hydrochloric acid. After the phase separation, the contents were concentrated and the residue was purified by chromatography, which gave 90 mg of clean product.

The examples listed in the tables below were prepared analogously to the abovementioned methods or are obtainable analogously to the abovementioned methods. The compounds listed in the tables below are very particularly preferred.

The abbreviations used mean:

| | | | |
|---|---|---|---|
| Et = ethyl | Me = methyl | n-Pr = n-propyl | i-Pr = isopropyl |
| c-Pr = cyclopropyl | Ph = phenyl | | |

TABLE 1

Inventive compounds of the general formula (I) in which Q is Q1 and R$^x$ is a methyl group and R" and W are each hydrogen

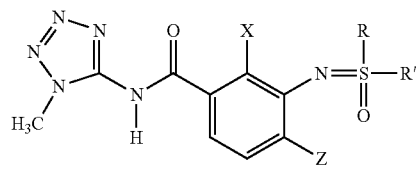

| No. | X | Z | R | R' | Physical data ($^1$H-NMR) |
|---|---|---|---|---|---|
| 1-1 | Me | Me | Et | Et | |
| 1-2 | Me | F | Et | Et | |
| 1-3 | Me | Cl | Et | Et | |
| 1-4 | Me | Br | Et | Et | |
| 1-5 | Me | I | Et | Et | |
| 1-6 | Me | CF$_3$ | Et | Et | |
| 1-7 | Me | CHF$_2$ | Et | Et | |
| 1-8 | Me | CF$_2$Cl | Et | Et | |
| 1-9 | Me | OMe | Et | Et | |
| 1-10 | Me | NO$_2$ | Et | Et | |
| 1-11 | Me | SO$_2$Me | Et | Et | |
| 1-12 | Cl | Me | Et | Et | |
| 1-13 | Cl | F | Et | Et | |
| 1-14 | Cl | Cl | Et | Et | (400 MHz, DMSO-d$_6$ δ, ppm) 7.54 (d, 1H), 7.30 (d, 1H), 3.99 (s, 3H), 3.42-3.26 (m, 4H), 1.33 (t, 6H) |
| 1-15 | Cl | Br | Et | Et | |
| 1-16 | Cl | I | Et | Et | |
| 1-17 | Cl | CF$_3$ | Et | Et | |
| 1-18 | Cl | CHF$_2$ | Et | Et | |
| 1-19 | Cl | CF$_2$Cl | Et | Et | |
| 1-20 | Cl | OMe | Et | Et | |
| 1-21 | Cl | NO$_2$ | Et | Et | |
| 1-22 | Cl | SO$_2$Me | Et | Et | |
| 1-23 | OMe | Me | Et | Et | |
| 1-24 | OMe | F | Et | Et | |
| 1-25 | OMe | Cl | Et | Et | |
| 1-26 | OMe | Br | Et | Et | |
| 1-27 | OMe | I | Et | Et | |

TABLE 1-continued

Inventive compounds of the general formula (I) in which Q is Q1 and $R^x$ is a methyl group and R" and W are each hydrogen

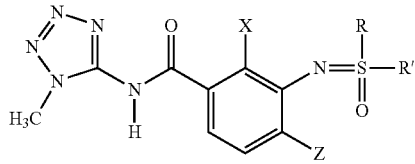

| No. | X | Z | R | R' | Physical data ($^1$H-NMR) |
|---|---|---|---|---|---|
| 1-28 | OMe | CF$_3$ | Et | Et | |
| 1-29 | OMe | CHF$_2$ | Et | Et | |
| 1-30 | OMe | CF$_2$Cl | Et | Et | |
| 1-31 | OMe | OMe | Et | Et | |
| 1-32 | OMe | NO$_2$ | Et | Et | |
| 1-33 | OMe | SO$_2$Me | Et | Et | |
| 1-34 | SO$_2$Me | Me | Et | Et | |
| 1-35 | SO$_2$Me | F | Et | Et | |
| 1-36 | SO$_2$Me | Cl | Et | Et | |
| 1-37 | SO$_2$Me | Br | Et | Et | |
| 1-38 | SO$_2$Me | I | Et | Et | |
| 1-39 | SO$_2$Me | CF$_3$ | Et | Et | |
| 1-40 | SO$_2$Me | CHF$_2$ | Et | Et | |
| 1-41 | SO$_2$Me | CF$_2$Cl | Et | Et | |
| 1-42 | SO$_2$Me | OMe | Et | Et | |
| 1-43 | SO$_2$Me | NO$_2$ | Et | Et | |
| 1-44 | SO$_2$Me | SO$_2$Me | Et | Et | |
| 1-45 | Me | Me | —(CH$_2$)$_5$— | | |
| 1-46 | Me | F | —(CH$_2$)$_5$— | | |
| 1-47 | Me | Cl | —(CH$_2$)$_5$— | | |
| 1-48 | Me | Br | —(CH$_2$)$_5$— | | |
| 1-49 | Me | I | —(CH$_2$)$_5$— | | |
| 1-50 | Me | CF$_3$ | —(CH$_2$)$_5$— | | |
| 1-51 | Me | CHF$_2$ | —(CH$_2$)$_5$— | | |
| 1-52 | Me | CF$_2$Cl | —(CH$_2$)$_5$— | | |
| 1-53 | Me | OMe | —(CH$_2$)$_5$— | | |
| 1-54 | Me | NO$_2$ | —(CH$_2$)$_5$— | | |
| 1-55 | Me | SO$_2$Me | —(CH$_2$)$_5$— | | |
| 1-56 | Cl | Me | —(CH$_2$)$_5$— | | |
| 1-57 | Cl | F | —(CH$_2$)$_5$— | | |
| 1-58 | Cl | Cl | —(CH$_2$)$_5$— | | (400 MHz, DMSO-d$_6$ δ, ppm) 7.55 (d, 1H), 7.31 (d, 1H), 3.99 (s, 3H), 3.42-3.25 (m, 4H), 2.13-2.05 (m, 2H), 1.98-1.88 (m, 2H), 1.70-1.55 (m, 2H) |
| 1-59 | Cl | Br | —(CH$_2$)$_5$— | | |
| 1-60 | Cl | I | —(CH$_2$)$_5$— | | |
| 1-61 | Cl | CF$_3$ | —(CH$_2$)$_5$— | | |
| 1-62 | Cl | CHF$_2$ | —(CH$_2$)$_5$— | | |
| 1-63 | Cl | CF$_2$Cl | —(CH$_2$)$_5$— | | |
| 1-64 | Cl | OMe | —(CH$_2$)$_5$— | | |
| 1-65 | Cl | NO$_2$ | —(CH$_2$)$_5$— | | |
| 1-66 | Cl | SO$_2$Me | —(CH$_2$)$_5$— | | |
| 1-67 | OMe | Me | —(CH$_2$)$_5$— | | |
| 1-68 | OMe | F | —(CH$_2$)$_5$— | | |
| 1-69 | OMe | Cl | —(CH$_2$)$_5$— | | |
| 1-70 | OMe | Br | —(CH$_2$)$_5$— | | |
| 1-71 | OMe | I | —(CH$_2$)$_5$— | | |
| 1-72 | OMe | CF$_3$ | —(CH$_2$)$_5$— | | |
| 1-73 | OMe | CHF$_2$ | —(CH$_2$)$_5$— | | |
| 1-74 | OMe | CF$_2$Cl | —(CH$_2$)$_5$— | | |
| 1-75 | OMe | OMe | —(CH$_2$)$_5$— | | |
| 1-76 | OMe | NO$_2$ | —(CH$_2$)$_5$— | | |
| 1-77 | OMe | SO$_2$Me | —(CH$_2$)$_5$— | | |
| 1-78 | SO$_2$Me | Me | —(CH$_2$)$_5$— | | |
| 1-79 | SO$_2$Me | F | —(CH$_2$)$_5$— | | |
| 1-80 | SO$_2$Me | Cl | —(CH$_2$)$_5$— | | |
| 1-81 | SO$_2$Me | Br | —(CH$_2$)$_5$— | | |
| 1-82 | SO$_2$Me | I | —(CH$_2$)$_5$— | | |
| 1-83 | SO$_2$Me | CF$_3$ | —(CH$_2$)$_5$— | | |
| 1-84 | SO$_2$Me | CHF$_2$ | —(CH$_2$)$_5$— | | |
| 1-85 | SO$_2$Me | CF$_2$Cl | —(CH$_2$)$_5$— | | |
| 1-86 | SO$_2$Me | OMe | —(CH$_2$)$_5$— | | |
| 1-87 | SO$_2$Me | NO$_2$ | —(CH$_2$)$_5$— | | |
| 1-88 | SO$_2$Me | SO$_2$Me | —(CH$_2$)$_5$— | | |
| 1-89 | Me | Me | —(CH$_2$)$_2$O(CH$_2$)$_2$— | | |
| 1-90 | Me | F | —(CH$_2$)$_2$O(CH$_2$)$_2$— | | |

TABLE 1-continued

Inventive compounds of the general formula (I) in which Q is Q1 and $R^x$ is a methyl group and R'' and W are each hydrogen

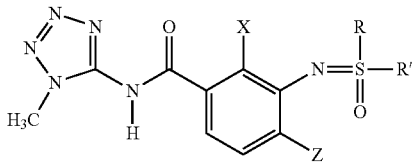

| No. | X | Z | R | R' | Physical data ($^1$H-NMR) |
|---|---|---|---|---|---|
| 1-91 | Me | Cl | —(CH$_2$)$_2$O(CH$_2$)$_2$— | | |
| 1-92 | Me | Br | —(CH$_2$)$_2$O(CH$_2$)$_2$— | | |
| 1-93 | Me | I | —(CH$_2$)$_2$O(CH$_2$)$_2$— | | |
| 1-94 | Me | CF$_3$ | —(CH$_2$)$_2$O(CH$_2$)$_2$— | | |
| 1-95 | Me | CHF$_2$ | —(CH$_2$)$_2$O(CH$_2$)$_2$— | | |
| 1-96 | Me | CF$_2$Cl | —(CH$_2$)$_2$O(CH$_2$)$_2$— | | |
| 1-97 | Me | OMe | —(CH$_2$)$_2$O(CH$_2$)$_2$— | | |
| 1-98 | Me | NO$_2$ | —(CH$_2$)$_2$O(CH$_2$)$_2$— | | |
| 1-99 | Me | SO$_2$Me | —(CH$_2$)$_2$O(CH$_2$)$_2$— | | |
| 1-100 | Cl | Me | —(CH$_2$)$_2$O(CH$_2$)$_2$— | | |
| 1-101 | Cl | F | —(CH$_2$)$_2$O(CH$_2$)$_2$— | | |
| 1-102 | Cl | Cl | —(CH$_2$)$_2$O(CH$_2$)$_2$— | | (400 MHz, DMSO-d$_6$ δ, ppm) 7.55 (d, 1H), 7.32 (d, 1H), 4.20 (m, 2H), 4.02 (m, 2H), 3.95 (s, 3H), 3.55-3.37 (m, 4H) |
| 1-103 | Cl | Br | —(CH$_2$)$_2$O(CH$_2$)$_2$— | | |
| 1-104 | Cl | I | —(CH$_2$)$_2$O(CH$_2$)$_2$— | | |
| 1-105 | Cl | CF$_3$ | —(CH$_2$)$_2$O(CH$_2$)$_2$— | | |
| 1-106 | Cl | CHF$_2$ | —(CH$_2$)$_2$O(CH$_2$)$_2$— | | |
| 1-107 | Cl | CF$_2$Cl | —(CH$_2$)$_2$O(CH$_2$)$_2$— | | |
| 1-108 | Cl | OMe | —(CH$_2$)$_2$O(CH$_2$)$_2$— | | |
| 1-109 | Cl | NO$_2$ | —(CH$_2$)$_2$O(CH$_2$)$_2$— | | |
| 1-110 | Cl | SO$_2$Me | —(CH$_2$)$_2$O(CH$_2$)$_2$— | | |
| 1-111 | OMe | Me | —(CH$_2$)$_2$O(CH$_2$)$_2$— | | |
| 1-112 | OMe | F | —(CH$_2$)$_2$O(CH$_2$)$_2$— | | |
| 1-113 | OMe | Cl | —(CH$_2$)$_2$O(CH$_2$)$_2$— | | |
| 1-114 | OMe | Br | —(CH$_2$)$_2$O(CH$_2$)$_2$— | | |
| 1-115 | OMe | I | —(CH$_2$)$_2$O(CH$_2$)$_2$— | | |
| 1-116 | OMe | CF$_3$ | —(CH$_2$)$_2$O(CH$_2$)$_2$— | | |
| 1-117 | OMe | CHF$_2$ | —(CH$_2$)$_2$O(CH$_2$)$_2$— | | |
| 1-118 | OMe | CF$_2$Cl | —(CH$_2$)$_2$O(CH$_2$)$_2$— | | |
| 1-119 | OMe | OMe | —(CH$_2$)$_2$O(CH$_2$)$_2$— | | |
| 1-120 | OMe | NO$_2$ | —(CH$_2$)$_2$O(CH$_2$)$_2$— | | |
| 1-121 | OMe | SO$_2$Me | —(CH$_2$)$_2$O(CH$_2$)$_2$— | | |
| 1-122 | SO$_2$Me | Me | —(CH$_2$)$_2$O(CH$_2$)$_2$— | | |
| 1-123 | SO$_2$Me | F | —(CH$_2$)$_2$O(CH$_2$)$_2$— | | |
| 1-124 | SO$_2$Me | Cl | —(CH$_2$)$_2$O(CH$_2$)$_2$— | | |
| 1-125 | SO$_2$Me | Br | —(CH$_2$)$_2$O(CH$_2$)$_2$— | | |
| 1-126 | SO$_2$Me | I | —(CH$_2$)$_2$O(CH$_2$)$_2$— | | |
| 1-127 | SO$_2$Me | CF$_3$ | —(CH$_2$)$_2$O(CH$_2$)$_2$— | | |
| 1-128 | SO$_2$Me | CHF$_2$ | —(CH$_2$)$_2$O(CH$_2$)$_2$— | | |
| 1-129 | SO$_2$Me | CF$_2$Cl | —(CH$_2$)$_2$O(CH$_2$)$_2$— | | |
| 1-130 | SO$_2$Me | OMe | —(CH$_2$)$_2$O(CH$_2$)$_2$— | | |
| 1-131 | SO$_2$Me | NO$_2$ | —(CH$_2$)$_2$O(CH$_2$)$_2$— | | |
| 1-132 | SO$_2$Me | SO$_2$Me | —(CH$_2$)$_2$O(CH$_2$)$_2$— | | |
| 1-133 | Cl | COOMe | Et | Et | |
| 1-134 | Cl | COOMe | —(CH$_2$)$_5$— | | |
| 1-135 | Cl | COOMe | —(CH$_2$)$_2$O(CH$_2$)$_2$— | | |

TABLE 2

Inventive compounds of the general formula (I) in which Q is Q1 and $R^x$ is an ethyl group and R" and W are each hydrogen

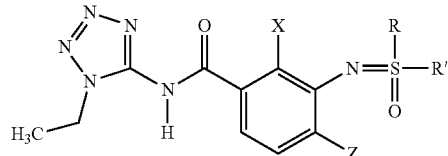

| No. | X | Z | R | R' | Physical data ($^1$H-NMR) |
|---|---|---|---|---|---|
| 2-1 | Me | Me | Et | Et | |
| 2-2 | Me | F | Et | Et | |
| 2-3 | Me | Cl | Et | Et | |
| 2-4 | Me | Br | Et | Et | |
| 2-5 | Me | I | Et | Et | |
| 2-6 | Me | CF$_3$ | Et | Et | |
| 2-7 | Me | CHF$_2$ | Et | Et | |
| 2-8 | Me | CF$_2$Cl | Et | Et | |
| 2-9 | Me | OMe | Et | Et | |
| 2-10 | Me | NO$_2$ | Et | Et | |
| 2-11 | Me | SO$_2$Me | Et | Et | |
| 2-12 | Cl | Me | Et | Et | |
| 2-13 | Cl | F | Et | Et | |
| 2-14 | Cl | Cl | Et | Et | (400 MHz, DMSO-d$_6$ δ, ppm) 7.53 (d, 1H), 7.28 (d, 1H), 4.34 (q, 2H), 1.46 (t, 3H), 1.33 (t, 6H) |
| 2-15 | Cl | Br | Et | Et | |
| 2-16 | Cl | I | Et | Et | |
| 2-17 | Cl | CF$_3$ | Et | Et | |
| 2-18 | Cl | CHF$_2$ | Et | Et | |
| 2-19 | Cl | CF$_2$Cl | Et | Et | |
| 2-20 | Cl | OMe | Et | Et | |
| 2-21 | Cl | NO$_2$ | Et | Et | |
| 2-22 | Cl | SO$_2$Me | Et | Et | |
| 2-23 | OMe | Me | Et | Et | |
| 2-24 | OMe | F | Et | Et | |
| 2-25 | OMe | Cl | Et | Et | |
| 2-26 | OMe | Br | Et | Et | |
| 2-27 | OMe | I | Et | Et | |
| 2-28 | OMe | CF$_3$ | Et | Et | |
| 2-29 | OMe | CHF$_2$ | Et | Et | |
| 2-30 | OMe | CF$_2$Cl | Et | Et | |
| 2-31 | OMe | OMe | Et | Et | |
| 2-32 | OMe | NO$_2$ | Et | Et | |
| 2-33 | OMe | SO$_2$Me | Et | Et | |
| 2-34 | SO$_2$Me | Me | Et | Et | |
| 2-35 | SO$_2$Me | F | Et | Et | |
| 2-36 | SO$_2$Me | Cl | Et | Et | |
| 2-37 | SO$_2$Me | Br | Et | Et | |
| 2-38 | SO$_2$Me | I | Et | Et | |
| 2-39 | SO$_2$Me | CF$_3$ | Et | Et | |
| 2-40 | SO$_2$Me | CHF$_2$ | Et | Et | |
| 2-41 | SO$_2$Me | CF$_2$Cl | Et | Et | |
| 2-42 | SO$_2$Me | OMe | Et | Et | |
| 2-43 | SO$_2$Me | NO$_2$ | Et | Et | |
| 2-44 | SO$_2$Me | SO$_2$Me | Et | Et | |
| 2-45 | Me | Me | —(CH$_2$)$_5$— | | |
| 2-46 | Me | F | —(CH$_2$)$_5$— | | |
| 2-47 | Me | Cl | —(CH$_2$)$_5$— | | |
| 2-48 | Me | Br | —(CH$_2$)$_5$— | | |
| 2-49 | Me | I | —(CH$_2$)$_5$— | | |
| 2-50 | Me | CF$_3$ | —(CH$_2$)$_5$— | | |
| 2-51 | Me | CHF$_2$ | —(CH$_2$)$_5$— | | |
| 2-52 | Me | CF$_2$Cl | —(CH$_2$)$_5$— | | |
| 2-53 | Me | OMe | —(CH$_2$)$_5$— | | |
| 2-54 | Me | NO$_2$ | —(CH$_2$)$_5$— | | |
| 2-55 | Me | SO$_2$Me | —(CH$_2$)$_5$— | | |
| 2-56 | Cl | Me | —(CH$_2$)$_5$— | | |
| 2-57 | Cl | F | —(CH$_2$)$_5$— | | |
| 2-58 | Cl | Cl | —(CH$_2$)$_5$— | | (400 MHz, DMSO-d$_6$ δ, ppm) 7.50 (d, 1H), 7.24 (d, 1H), 4.30 (q, 2H), 2.12-2.03 (m, 2H), 2.00-1.88 (m, 4H), 1.70-1.53 (m, 2H), 1.43 (t, 3H) |
| 2-59 | Cl | Br | —(CH$_2$)$_5$— | | |
| 2-60 | Cl | I | —(CH$_2$)$_5$— | | |
| 2-61 | Cl | CF$_3$ | —(CH$_2$)$_5$— | | |

TABLE 2-continued

Inventive compounds of the general formula (I) in which Q is Q1 and $R^x$ is an ethyl group and R" and W are each hydrogen

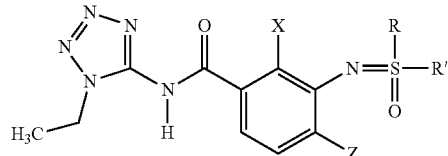

| No. | X | Z | R R' | Physical data ($^1$H-NMR) |
|---|---|---|---|---|
| 2-62 | Cl | CHF$_2$ | —(CH$_2$)$_5$— | |
| 2-63 | Cl | CF$_2$Cl | —(CH$_2$)$_5$— | |
| 2-64 | Cl | OMe | —(CH$_2$)$_5$— | |
| 2-65 | Cl | NO$_2$ | —(CH$_2$)$_5$— | |
| 2-66 | Cl | SO$_2$Me | —(CH$_2$)$_5$— | |
| 2-67 | OMe | Me | —(CH$_2$)$_5$— | |
| 2-68 | OMe | F | —(CH$_2$)$_5$— | |
| 2-69 | OMe | Cl | —(CH$_2$)$_5$— | |
| 2-70 | OMe | Br | —(CH$_2$)$_5$— | |
| 2-71 | OMe | I | —(CH$_2$)$_5$— | |
| 2-72 | OMe | CF$_3$ | —(CH$_2$)$_5$— | |
| 2-73 | OMe | CHF$_2$ | —(CH$_2$)$_5$— | |
| 2-74 | OMe | CF$_2$Cl | —(CH$_2$)$_5$— | |
| 2-75 | OMe | OMe | —(CH$_2$)$_5$— | |
| 2-76 | OMe | NO$_2$ | —(CH$_2$)$_5$— | |
| 2-77 | OMe | SO$_2$Me | —(CH$_2$)$_5$— | |
| 2-78 | SO$_2$Me | Me | —(CH$_2$)$_5$— | |
| 2-79 | SO$_2$Me | F | —(CH$_2$)$_5$— | |
| 2-80 | SO$_2$Me | Cl | —(CH$_2$)$_5$— | |
| 2-81 | SO$_2$Me | Br | —(CH$_2$)$_5$— | |
| 2-82 | SO$_2$Me | I | —(CH$_2$)$_5$— | |
| 2-83 | SO$_2$Me | CF$_3$ | —(CH$_2$)$_5$— | |
| 2-84 | SO$_2$Me | CHF$_2$ | —(CH$_2$)$_5$— | |
| 2-85 | SO$_2$Me | CF$_2$Cl | —(CH$_2$)$_5$— | |
| 2-86 | SO$_2$Me | OMe | —(CH$_2$)$_5$— | |
| 2-87 | SO$_2$Me | NO$_2$ | —(CH$_2$)$_5$— | |
| 2-88 | SO$_2$Me | SO$_2$Me | —(CH$_2$)$_5$— | |
| 2-89 | Me | Me | —(CH$_2$)$_2$O(CH$_2$)$_2$— | |
| 2-90 | Me | F | —(CH$_2$)$_2$O(CH$_2$)$_2$— | |
| 2-91 | Me | Cl | —(CH$_2$)$_2$O(CH$_2$)$_2$— | |
| 2-92 | Me | Br | —(CH$_2$)$_2$O(CH$_2$)$_2$— | |
| 2-93 | Me | I | —(CH$_2$)$_2$O(CH$_2$)$_2$— | |
| 2-94 | Me | CF$_3$ | —(CH$_2$)$_2$O(CH$_2$)$_2$— | |
| 2-95 | Me | CHF$_2$ | —(CH$_2$)$_2$O(CH$_2$)$_2$— | |
| 2-96 | Me | CF$_2$Cl | —(CH$_2$)$_2$O(CH$_2$)$_2$— | |
| 2-97 | Me | OMe | —(CH$_2$)$_2$O(CH$_2$)$_2$— | |
| 2-98 | Me | NO$_2$ | —(CH$_2$)$_2$O(CH$_2$)$_2$— | |
| 2-99 | Me | SO$_2$Me | —(CH$_2$)$_2$O(CH$_2$)$_2$— | |
| 2-100 | Cl | Me | —(CH$_2$)$_2$O(CH$_2$)$_2$— | |
| 2-101 | Cl | F | —(CH$_2$)$_2$O(CH$_2$)$_2$— | |
| 2-102 | Cl | Cl | —(CH$_2$)$_2$O(CH$_2$)$_2$— | (400 MHz, DMSO-d$_6$ δ, ppm) 7.58 (d, 1H), 7.34 (d, 1H), 4.35 (q, 2H), 4.20 (m, 2H), 4.04 (m, 2H), 3.56-3.48 (m, 2H), 3.48-3.41 (m, 2H), 1.46 (t, 3H) |
| 2-103 | Cl | Br | —(CH$_2$)$_2$O(CH$_2$)$_2$— | |
| 2-104 | Cl | I | —(CH$_2$)$_2$O(CH$_2$)$_2$— | |
| 2-105 | Cl | CF$_3$ | —(CH$_2$)$_2$O(CH$_2$)$_2$— | |
| 2-106 | Cl | CHF$_2$ | —(CH$_2$)$_2$O(CH$_2$)$_2$— | |
| 2-107 | Cl | CF$_2$Cl | —(CH$_2$)$_2$O(CH$_2$)$_2$— | |
| 2-108 | Cl | OMe | —(CH$_2$)$_2$O(CH$_2$)$_2$— | |
| 2-109 | Cl | NO$_2$ | —(CH$_2$)$_2$O(CH$_2$)$_2$— | |
| 2-110 | Cl | SO$_2$Me | —(CH$_2$)$_2$O(CH$_2$)$_2$— | |
| 2-111 | OMe | Me | —(CH$_2$)$_2$O(CH$_2$)$_2$— | |
| 2-112 | OMe | F | —(CH$_2$)$_2$O(CH$_2$)$_2$— | |
| 2-113 | OMe | Cl | —(CH$_2$)$_2$O(CH$_2$)$_2$— | |
| 2-114 | OMe | Br | —(CH$_2$)$_2$O(CH$_2$)$_2$— | |
| 2-115 | OMe | I | —(CH$_2$)$_2$O(CH$_2$)$_2$— | |
| 2-116 | OMe | CF$_3$ | —(CH$_2$)$_2$O(CH$_2$)$_2$— | |
| 2-117 | OMe | CHF$_2$ | —(CH$_2$)$_2$O(CH$_2$)$_2$— | |
| 2-118 | OMe | CF$_2$Cl | —(CH$_2$)$_2$O(CH$_2$)$_2$— | |
| 2-119 | OMe | OMe | —(CH$_2$)$_2$O(CH$_2$)$_2$— | |
| 2-120 | OMe | NO$_2$ | —(CH$_2$)$_2$O(CH$_2$)$_2$— | |
| 2-121 | OMe | SO$_2$Me | —(CH$_2$)$_2$O(CH$_2$)$_2$— | |
| 2-122 | SO$_2$Me | Me | —(CH$_2$)$_2$O(CH$_2$)$_2$— | |
| 2-123 | SO$_2$Me | F | —(CH$_2$)$_2$O(CH$_2$)$_2$— | |
| 2-124 | SO$_2$Me | Cl | —(CH$_2$)$_2$O(CH$_2$)$_2$— | |

TABLE 2-continued

Inventive compounds of the general formula (I) in which Q is Q1 and $R^x$ is an ethyl group and R" and W are each hydrogen

| No. | X | Z | R | R' | Physical data ($^1$H-NMR) |
|---|---|---|---|---|---|
| 2-125 | SO$_2$Me | Br | —(CH$_2$)$_2$O(CH$_2$)$_2$— | | |
| 2-126 | SO$_2$Me | I | —(CH$_2$)$_2$O(CH$_2$)$_2$— | | |
| 2-127 | SO$_2$Me | CF$_3$ | —(CH$_2$)$_2$O(CH$_2$)$_2$— | | |
| 2-128 | SO$_2$Me | CHF$_2$ | —(CH$_2$)$_2$O(CH$_2$)$_2$— | | |
| 2-129 | SO$_2$Me | CF$_2$Cl | —(CH$_2$)$_2$O(CH$_2$)$_2$— | | |
| 2-130 | SO$_2$Me | OMe | —(CH$_2$)$_2$O(CH$_2$)$_2$— | | |
| 2-131 | SO$_2$Me | NO$_2$ | —(CH$_2$)$_2$O(CH$_2$)$_2$— | | |
| 2-132 | SO$_2$Me | SO$_2$Me | —(CH$_2$)$_2$O(CH$_2$)$_2$— | | |
| 2-133 | Cl | COOMe | Et | Et | |
| 2-134 | Cl | COOMe | —(CH$_2$)$_5$— | | |
| 2-135 | Cl | COOMe | —(CH$_2$)$_2$O(CH$_2$)$_2$— | | |

TABLE 3

Inventive compounds of the general formula (I) in which Q is Q1 and $R^x$ is an n-propyl group and R" and W are each hydrogen

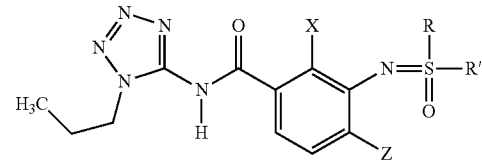

| No. | X | Z | R | R' | Physical data ($^1$H-NMR) |
|---|---|---|---|---|---|
| 3-1 | Me | Me | Et | Et | |
| 3-2 | Me | F | Et | Et | |
| 3-3 | Me | Cl | Et | Et | |
| 3-4 | Me | Br | Et | Et | |
| 3-5 | Me | I | Et | Et | |
| 3-6 | Me | CF$_3$ | Et | Et | |
| 3-7 | Me | CHF$_2$ | Et | Et | |
| 3-8 | Me | CF$_2$Cl | Et | Et | |
| 3-9 | Me | OMe | Et | Et | |
| 3-10 | Me | NO$_2$ | Et | Et | |
| 3-11 | Me | SO$_2$Me | Et | Et | |
| 3-12 | Cl | Me | Et | Et | |
| 3-13 | Cl | F | Et | Et | |
| 3-14 | Cl | Cl | Et | Et | (400 MHz, DMSO-d$_6$ δ, ppm) 7.52 (d, 1H), 7.25 (d, 1H), 4.28 (t, 2H), 1.87 (q, 2H), 1.33 (t, 6H), 0.87 (t, 3H) |
| 3-15 | Cl | Br | Et | Et | |
| 3-16 | Cl | I | Et | Et | |
| 3-17 | Cl | CF$_3$ | Et | Et | |
| 3-18 | Cl | CHF$_2$ | Et | Et | |
| 3-19 | Cl | CF$_2$Cl | Et | Et | |
| 3-20 | Cl | OMe | Et | Et | |
| 3-21 | Cl | NO$_2$ | Et | Et | |
| 3-22 | Cl | SO$_2$Me | Et | Et | |
| 3-23 | OMe | Me | Et | Et | |
| 3-24 | OMe | F | Et | Et | |
| 3-25 | OMe | Cl | Et | Et | |
| 3-26 | OMe | Br | Et | Et | |
| 3-27 | OMe | I | Et | Et | |
| 3-28 | OMe | CF$_3$ | Et | Et | |
| 3-29 | OMe | CHF$_2$ | Et | Et | |
| 3-30 | OMe | CF$_2$Cl | Et | Et | |
| 3-31 | OMe | OMe | Et | Et | |
| 3-32 | OMe | NO$_2$ | Et | Et | |
| 3-33 | OMe | SO$_2$Me | Et | Et | |
| 3-34 | SO$_2$Me | Me | Et | Et | |

TABLE 3-continued

Inventive compounds of the general formula (I) in which Q is Q1 and $R^x$ is an n-propyl group and R" and W are each hydrogen

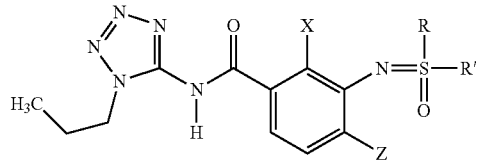

| No. | X | Z | R | R' | Physical data ($^1$H-NMR) |
|---|---|---|---|---|---|
| 3-35 | SO$_2$Me | F | Et | Et | |
| 3-36 | SO$_2$Me | Cl | Et | Et | |
| 3-37 | SO$_2$Me | Br | Et | Et | |
| 3-38 | SO$_2$Me | I | Et | Et | |
| 3-39 | SO$_2$Me | CF$_3$ | Et | Et | |
| 3-40 | SO$_2$Me | CHF$_2$ | Et | Et | |
| 3-41 | SO$_2$Me | CF$_2$Cl | Et | Et | |
| 3-42 | SO$_2$Me | OMe | Et | Et | |
| 3-43 | SO$_2$Me | NO$_2$ | Et | Et | |
| 3-44 | SO$_2$Me | SO$_2$Me | Et | Et | |
| 3-45 | Me | Me | —(CH$_2$)$_5$— | | |
| 3-46 | Me | F | —(CH$_2$)$_5$— | | |
| 3-47 | Me | Cl | —(CH$_2$)$_5$— | | |
| 3-48 | Me | Br | —(CH$_2$)$_5$— | | |
| 3-49 | Me | I | —(CH$_2$)$_5$— | | |
| 3-50 | Me | CF$_3$ | —(CH$_2$)$_5$— | | |
| 3-51 | Me | CHF$_2$ | —(CH$_2$)$_5$— | | |
| 3-52 | Me | CF$_2$Cl | —(CH$_2$)$_5$— | | |
| 3-53 | Me | OMe | —(CH$_2$)$_5$— | | |
| 3-54 | Me | NO$_2$ | —(CH$_2$)$_5$— | | |
| 3-55 | Me | SO$_2$Me | —(CH$_2$)$_5$— | | |
| 3-56 | Cl | Me | —(CH$_2$)$_5$— | | |
| 3-57 | Cl | F | —(CH$_2$)$_5$— | | |
| 3-58 | Cl | Cl | —(CH$_2$)$_5$— | | (400 MHz, DMSO-d$_6$ δ, ppm) 7.54 (d, 1H), 7.27 (d, 1H), 4.29 (t, 2H), 3.42-3.25 (m, 4H), 2.13-2.05 (m, 2H), 2.00-1.82 (m, 4H), 1.70-1.51 (m, 2H), 0.87 (t, 3H) |
| 3-59 | Cl | Br | —(CH$_2$)$_5$— | | |
| 3-60 | Cl | I | —(CH$_2$)$_5$— | | |
| 3-61 | Cl | CF$_3$ | —(CH$_2$)$_5$— | | |
| 3-62 | Cl | CHF$_2$ | —(CH$_2$)$_5$— | | |
| 3-63 | Cl | CF$_2$Cl | —(CH$_2$)$_5$— | | |
| 3-64 | Cl | OMe | —(CH$_2$)$_5$— | | |
| 3-65 | Cl | NO$_2$ | —(CH$_2$)$_5$— | | |
| 3-66 | Cl | SO$_2$Me | —(CH$_2$)$_5$— | | |
| 3-67 | OMe | Me | —(CH$_2$)$_5$— | | |
| 3-68 | OMe | F | —(CH$_2$)$_5$— | | |
| 3-69 | OMe | Cl | —(CH$_2$)$_5$— | | |
| 3-70 | OMe | Br | —(CH$_2$)$_5$— | | |
| 3-71 | OMe | I | —(CH$_2$)$_5$— | | |
| 3-72 | OMe | CF$_3$ | —(CH$_2$)$_5$— | | |
| 3-73 | OMe | CHF$_2$ | —(CH$_2$)$_5$— | | |
| 3-74 | OMe | CF$_2$Cl | —(CH$_2$)$_5$— | | |
| 3-75 | OMe | OMe | —(CH$_2$)$_5$— | | |
| 3-76 | OMe | NO$_2$ | —(CH$_2$)$_5$— | | |
| 3-77 | OMe | SO$_2$Me | —(CH$_2$)$_5$— | | |
| 3-78 | SO$_2$Me | Me | —(CH$_2$)$_5$— | | |
| 3-79 | SO$_2$Me | F | —(CH$_2$)$_5$— | | |
| 3-80 | SO$_2$Me | Cl | —(CH$_2$)$_5$— | | |
| 3-81 | SO$_2$Me | Br | —(CH$_2$)$_5$— | | |
| 3-82 | SO$_2$Me | I | —(CH$_2$)$_5$— | | |
| 3-83 | SO$_2$Me | CF$_3$ | —(CH$_2$)$_5$— | | |
| 3-84 | SO$_2$Me | CHF$_2$ | —(CH$_2$)$_5$— | | |
| 3-85 | SO$_2$Me | CF$_2$Cl | —(CH$_2$)$_5$— | | |
| 3-86 | SO$_2$Me | OMe | —(CH$_2$)$_5$— | | |
| 3-87 | SO$_2$Me | NO$_2$ | —(CH$_2$)$_5$— | | |
| 3-88 | SO$_2$Me | SO$_2$Me | —(CH$_2$)$_5$— | | |
| 3-89 | Me | Me | —(CH$_2$)$_2$O(CH$_2$)$_2$— | | |
| 3-90 | Me | F | —(CH$_2$)$_2$O(CH$_2$)$_2$— | | |
| 3-91 | Me | Cl | —(CH$_2$)$_2$O(CH$_2$)$_2$— | | |
| 3-92 | Me | Br | —(CH$_2$)$_2$O(CH$_2$)$_2$— | | |
| 3-93 | Me | I | —(CH$_2$)$_2$O(CH$_2$)$_2$— | | |
| 3-94 | Me | CF$_3$ | —(CH$_2$)$_2$O(CH$_2$)$_2$— | | |
| 3-95 | Me | CHF$_2$ | —(CH$_2$)$_2$O(CH$_2$)$_2$— | | |
| 3-96 | Me | CF$_2$Cl | —(CH$_2$)$_2$O(CH$_2$)$_2$— | | |
| 3-97 | Me | OMe | —(CH$_2$)$_2$O(CH$_2$)$_2$— | | |

TABLE 3-continued

Inventive compounds of the general formula (I) in which Q is Q1 and $R^x$ is an n-propyl group and R" and W are each hydrogen

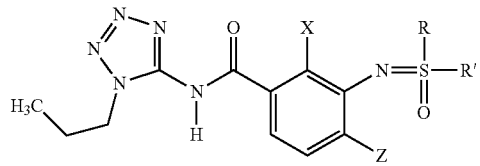

| No. | X | Z | R | R' | Physical data ($^1$H-NMR) |
|---|---|---|---|---|---|
| 3-98 | Me | $NO_2$ | —$(CH_2)_2O(CH_2)_2$— | | |
| 3-99 | Me | $SO_2Me$ | —$(CH_2)_2O(CH_2)_2$— | | |
| 3-100 | Cl | Me | —$(CH_2)_2O(CH_2)_2$— | | |
| 3-101 | Cl | F | —$(CH_2)_2O(CH_2)_2$— | | |
| 3-102 | Cl | Cl | —$(CH_2)_2O(CH_2)_2$— | | (400 MHz, DMSO-$d_6$ δ, ppm) 7.57 (d, 1H), 7.31 (d, 1H), 4.29 (t, 2H), 4.22-4.15 (m, 2H), 4.02 (m, 2H), 3.55-3.40 (m, 4H), 1.87 (m, 2H), 0.87 (t, 3H) |
| 3-103 | Cl | Br | —$(CH_2)_2O(CH_2)_2$— | | |
| 3-104 | Cl | I | —$(CH_2)_2O(CH_2)_2$— | | |
| 3-105 | Cl | $CF_3$ | —$(CH_2)_2O(CH_2)_2$— | | |
| 3-106 | Cl | $CHF_2$ | —$(CH_2)_2O(CH_2)_2$— | | |
| 3-107 | Cl | $CF_2Cl$ | —$(CH_2)_2O(CH_2)_2$— | | |
| 3-108 | Cl | OMe | —$(CH_2)_2O(CH_2)_2$— | | |
| 3-109 | Cl | $NO_2$ | —$(CH_2)_2O(CH_2)_2$— | | |
| 3-110 | Cl | $SO_2Me$ | —$(CH_2)_2O(CH_2)_2$— | | |
| 3-111 | OMe | Me | —$(CH_2)_2O(CH_2)_2$— | | |
| 3-112 | OMe | F | —$(CH_2)_2O(CH_2)_2$— | | |
| 3-113 | OMe | Cl | —$(CH_2)_2O(CH_2)_2$— | | |
| 3-114 | OMe | Br | —$(CH_2)_2O(CH_2)_2$— | | |
| 3-115 | OMe | I | —$(CH_2)_2O(CH_2)_2$— | | |
| 3-116 | OMe | $CF_3$ | —$(CH_2)_2O(CH_2)_2$— | | |
| 3-117 | OMe | $CHF_2$ | —$(CH_2)_2O(CH_2)_2$— | | |
| 3-118 | OMe | $CF_2Cl$ | —$(CH_2)_2O(CH_2)_2$— | | |
| 3-119 | OMe | OMe | —$(CH_2)_2O(CH_2)_2$— | | |
| 3-120 | OMe | $NO_2$ | —$(CH_2)_2O(CH_2)_2$— | | |
| 3-121 | OMe | $SO_2Me$ | —$(CH_2)_2O(CH_2)_2$— | | |
| 3-122 | $SO_2Me$ | Me | —$(CH_2)_2O(CH_2)_2$— | | |
| 3-123 | $SO_2Me$ | F | —$(CH_2)_2O(CH_2)_2$— | | |
| 3-124 | $SO_2Me$ | Cl | —$(CH_2)_2O(CH_2)_2$— | | |
| 3-125 | $SO_2Me$ | Br | —$(CH_2)_2O(CH_2)_2$— | | |
| 3-126 | $SO_2Me$ | I | —$(CH_2)_2O(CH_2)_2$— | | |
| 3-127 | $SO_2Me$ | $CF_3$ | —$(CH_2)_2O(CH_2)_2$— | | |
| 3-128 | $SO_2Me$ | $CHF_2$ | —$(CH_2)_2O(CH_2)_2$— | | |
| 3-129 | $SO_2Me$ | $CF_2Cl$ | —$(CH_2)_2O(CH_2)_2$— | | |
| 3-130 | $SO_2Me$ | OMe | —$(CH_2)_2O(CH_2)_2$— | | |
| 3-131 | $SO_2Me$ | $NO_2$ | —$(CH_2)_2O(CH_2)_2$— | | |
| 3-132 | $SO_2Me$ | $SO_2Me$ | —$(CH_2)_2O(CH_2)_2$— | | |
| 3-133 | Cl | COOMe | Et | Et | |
| 3-134 | Cl | COOMe | —$(CH_2)_5$— | | |
| 3-135 | Cl | COOMe | —$(CH_2)_2O(CH_2)_2$— | | |

TABLE 4

Inventive compounds of the general formula (I) in which Q is Q1 and $R^x$ is a 2-methoxyethyl group and R" and W are each hydrogen

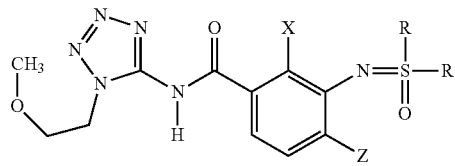

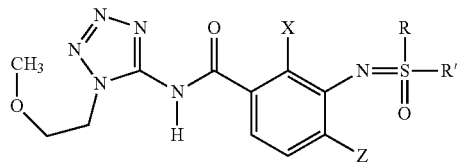

| No. | X | Z | R | R' | Physical data ($^1$H-NMR) |
|---|---|---|---|---|---|
| 4-1 | Me | Me | Et | Et | |
| 4-2 | Me | F | Et | Et | |
| 4-3 | Me | Cl | Et | Et | |
| 4-4 | Me | Br | Et | Et | |
| 4-5 | Me | I | Et | Et | |
| 4-6 | Me | $CF_3$ | Et | Et | |
| 4-7 | Me | $CHF_2$ | Et | Et | |
| 4-8 | Me | $CF_2Cl$ | Et | Et | |

TABLE 4-continued

Inventive compounds of the general formula (I) in which Q is Q1 and R$^x$ is a 2-methoxyethyl group and R" and W are each hydrogen

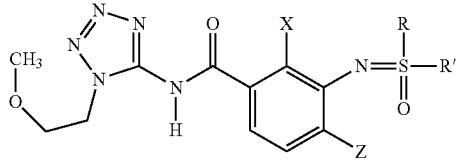
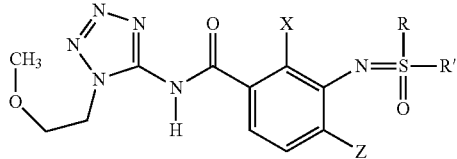

| No. | X | Z | R | R' | Physical data ($^1$H-NMR) |
|---|---|---|---|---|---|
| 4-9 | Me | OMe | Et | Et | |
| 4-10 | Me | NO$_2$ | Et | Et | |
| 4-11 | Me | SO$_2$Me | Et | Et | |
| 4-12 | Cl | Me | Et | Et | |
| 4-13 | Cl | F | Et | Et | |
| 4-14 | Cl | Cl | Et | Et | |
| 4-15 | Cl | Br | Et | Et | |
| 4-16 | Cl | I | Et | Et | |
| 4-17 | Cl | CF$_3$ | Et | Et | |
| 4-18 | Cl | CHF$_2$ | Et | Et | |
| 4-19 | Cl | CF$_2$Cl | Et | Et | |
| 4-20 | Cl | OMe | Et | Et | |
| 4-21 | Cl | NO$_2$ | Et | Et | |
| 4-22 | Cl | SO$_2$Me | Et | Et | |
| 4-23 | OMe | Me | Et | Et | |
| 4-24 | OMe | F | Et | Et | |
| 4-25 | OMe | Cl | Et | Et | |
| 4-26 | OMe | Br | Et | Et | |
| 4-27 | OMe | I | Et | Et | |
| 4-28 | OMe | CF$_3$ | Et | Et | |
| 4-29 | OMe | CHF$_2$ | Et | Et | |
| 4-30 | OMe | CF$_2$Cl | Et | Et | |
| 4-31 | OMe | OMe | Et | Et | |
| 4-32 | OMe | NO$_2$ | Et | Et | |
| 4-33 | OMe | SO$_2$Me | Et | Et | |
| 4-34 | SO$_2$Me | Me | Et | Et | |
| 4-35 | SO$_2$Me | F | Et | Et | |
| 4-36 | SO$_2$Me | Cl | Et | Et | |
| 4-37 | SO$_2$Me | Br | Et | Et | |
| 4-38 | SO$_2$Me | I | Et | Et | |
| 4-39 | SO$_2$Me | CF$_3$ | Et | Et | |
| 4-40 | SO$_2$Me | CHF$_2$ | Et | Et | |
| 4-41 | SO$_2$Me | CF$_2$Cl | Et | Et | |
| 4-42 | SO$_2$Me | OMe | Et | Et | |
| 4-43 | SO$_2$Me | NO$_2$ | Et | Et | |
| 4-44 | SO$_2$Me | SO$_2$Me | Et | Et | |
| 4-45 | Me | Me | —(CH$_2$)$_5$— | | |
| 4-46 | Me | F | —(CH$_2$)$_5$— | | |
| 4-47 | Me | Cl | —(CH$_2$)$_5$— | | |
| 4-48 | Me | Br | —(CH$_2$)$_5$— | | |
| 4-49 | Me | I | —(CH$_2$)$_5$— | | |
| 4-50 | Me | CF$_3$ | —(CH$_2$)$_5$— | | |
| 4-51 | Me | CHF$_2$ | —(CH$_2$)$_5$— | | |
| 4-52 | Me | CF$_2$Cl | —(CH$_2$)$_5$— | | |
| 4-53 | Me | OMe | —(CH$_2$)$_5$— | | |
| 4-54 | Me | NO$_2$ | —(CH$_2$)$_5$— | | |
| 4-55 | Me | SO$_2$Me | —(CH$_2$)$_5$— | | |
| 4-56 | Cl | Me | —(CH$_2$)$_5$— | | |
| 4-57 | Cl | F | —(CH$_2$)$_5$— | | |
| 4-58 | Cl | Cl | —(CH$_2$)$_5$— | | |
| 4-59 | Cl | Br | —(CH$_2$)$_5$— | | |
| 4-60 | Cl | I | —(CH$_2$)$_5$— | | |
| 4-61 | Cl | CF$_3$ | —(CH$_2$)$_5$— | | |
| 4-62 | Cl | CHF$_2$ | —(CH$_2$)$_5$— | | |
| 4-63 | Cl | CF$_2$Cl | —(CH$_2$)$_5$— | | |
| 4-64 | Cl | OMe | —(CH$_2$)$_5$— | | |
| 4-65 | Cl | NO$_2$ | —(CH$_2$)$_5$— | | |
| 4-66 | Cl | SO$_2$Me | —(CH$_2$)$_5$— | | |
| 4-67 | OMe | Me | —(CH$_2$)$_5$— | | |
| 4-68 | OMe | F | —(CH$_2$)$_5$— | | |
| 4-69 | OMe | Cl | —(CH$_2$)$_5$— | | |
| 4-70 | OMe | Br | —(CH$_2$)$_5$— | | |
| 4-71 | OMe | I | —(CH$_2$)$_5$— | | |
| 4-72 | OMe | CF$_3$ | —(CH$_2$)$_5$— | | |
| 4-73 | OMe | CHF$_2$ | —(CH$_2$)$_5$— | | |
| 4-74 | OMe | CF$_2$Cl | —(CH$_2$)$_5$— | | |
| 4-75 | OMe | OMe | —(CH$_2$)$_5$— | | |
| 4-76 | OMe | NO$_2$ | —(CH$_2$)$_5$— | | |
| 4-77 | OMe | SO$_2$Me | —(CH$_2$)$_5$— | | |
| 4-78 | SO$_2$Me | Me | —(CH$_2$)$_5$— | | |
| 4-79 | SO$_2$Me | F | —(CH$_2$)$_5$— | | |
| 4-80 | SO$_2$Me | Cl | —(CH$_2$)$_5$— | | |
| 4-81 | SO$_2$Me | Br | —(CH$_2$)$_5$— | | |
| 4-82 | SO$_2$Me | I | —(CH$_2$)$_5$— | | |
| 4-83 | SO$_2$Me | CF$_3$ | —(CH$_2$)$_5$— | | |
| 4-84 | SO$_2$Me | CHF$_2$ | —(CH$_2$)$_5$— | | |
| 4-85 | SO$_2$Me | CF$_2$Cl | —(CH$_2$)$_5$— | | |
| 4-86 | SO$_2$Me | OMe | —(CH$_2$)$_5$— | | |
| 4-87 | SO$_2$Me | NO$_2$ | —(CH$_2$)$_5$— | | |
| 4-88 | SO$_2$Me | SO$_2$Me | —(CH$_2$)$_5$— | | |
| 4-89 | Me | Me | —(CH$_2$)$_2$O(CH$_2$)$_2$— | | |
| 4-90 | Me | F | —(CH$_2$)$_2$O(CH$_2$)$_2$— | | |
| 4-91 | Me | Cl | —(CH$_2$)$_2$O(CH$_2$)$_2$— | | |
| 4-92 | Me | Br | —(CH$_2$)$_2$O(CH$_2$)$_2$— | | |
| 4-93 | Me | I | —(CH$_2$)$_2$O(CH$_2$)$_2$— | | |
| 4-94 | Me | CF$_3$ | —(CH$_2$)$_2$O(CH$_2$)$_2$— | | |
| 4-95 | Me | CHF$_2$ | —(CH$_2$)$_2$O(CH$_2$)$_2$— | | |
| 4-96 | Me | CF$_2$Cl | —(CH$_2$)$_2$O(CH$_2$)$_2$— | | |
| 4-97 | Me | OMe | —(CH$_2$)$_2$O(CH$_2$)$_2$— | | |
| 4-98 | Me | NO$_2$ | —(CH$_2$)$_2$O(CH$_2$)$_2$— | | |
| 4-99 | Me | SO$_2$Me | —(CH$_2$)$_2$O(CH$_2$)$_2$— | | |
| 4-100 | Cl | Me | —(CH$_2$)$_2$O(CH$_2$)$_2$— | | |
| 4-101 | Cl | F | —(CH$_2$)$_2$O(CH$_2$)$_2$— | | |
| 4-102 | Cl | Cl | —(CH$_2$)$_2$O(CH$_2$)$_2$— | | |
| 4-103 | Cl | Br | —(CH$_2$)$_2$O(CH$_2$)$_2$— | | |
| 4-104 | Cl | I | —(CH$_2$)$_2$O(CH$_2$)$_2$— | | |
| 4-105 | Cl | CF$_3$ | —(CH$_2$)$_2$O(CH$_2$)$_2$— | | |
| 4-106 | Cl | CHF$_2$ | —(CH$_2$)$_2$O(CH$_2$)$_2$— | | |
| 4-107 | Cl | CF$_2$Cl | —(CH$_2$)$_2$O(CH$_2$)$_2$— | | |
| 4-108 | Cl | OMe | —(CH$_2$)$_2$O(CH$_2$)$_2$— | | |
| 4-109 | Cl | NO$_2$ | —(CH$_2$)$_2$O(CH$_2$)$_2$— | | |
| 4-110 | Cl | SO$_2$Me | —(CH$_2$)$_2$O(CH$_2$)$_2$— | | |
| 4-111 | OMe | Me | —(CH$_2$)$_2$O(CH$_2$)$_2$— | | |
| 4-112 | OMe | F | —(CH$_2$)$_2$O(CH$_2$)$_2$— | | |
| 4-113 | OMe | Cl | —(CH$_2$)$_2$O(CH$_2$)$_2$— | | |
| 4-114 | OMe | Br | —(CH$_2$)$_2$O(CH$_2$)$_2$— | | |
| 4-115 | OMe | I | —(CH$_2$)$_2$O(CH$_2$)$_2$— | | |
| 4-116 | OMe | CF$_3$ | —(CH$_2$)$_2$O(CH$_2$)$_2$— | | |
| 4-117 | OMe | CHF$_2$ | —(CH$_2$)$_2$O(CH$_2$)$_2$— | | |
| 4-118 | OMe | CF$_2$Cl | —(CH$_2$)$_2$O(CH$_2$)$_2$— | | |
| 4-119 | OMe | OMe | —(CH$_2$)$_2$O(CH$_2$)$_2$— | | |
| 4-120 | OMe | NO$_2$ | —(CH$_2$)$_2$O(CH$_2$)$_2$— | | |
| 4-121 | OMe | SO$_2$Me | —(CH$_2$)$_2$O(CH$_2$)$_2$— | | |
| 4-122 | SO$_2$Me | Me | —(CH$_2$)$_2$O(CH$_2$)$_2$— | | |
| 4-123 | SO$_2$Me | F | —(CH$_2$)$_2$O(CH$_2$)$_2$— | | |
| 4-124 | SO$_2$Me | Cl | —(CH$_2$)$_2$O(CH$_2$)$_2$— | | |
| 4-125 | SO$_2$Me | Br | —(CH$_2$)$_2$O(CH$_2$)$_2$— | | |
| 4-126 | SO$_2$Me | I | —(CH$_2$)$_2$O(CH$_2$)$_2$— | | |
| 4-127 | SO$_2$Me | CF$_3$ | —(CH$_2$)$_2$O(CH$_2$)$_2$— | | |
| 4-128 | SO$_2$Me | CHF$_2$ | —(CH$_2$)$_2$O(CH$_2$)$_2$— | | |
| 4-129 | SO$_2$Me | CF$_2$Cl | —(CH$_2$)$_2$O(CH$_2$)$_2$— | | |
| 4-130 | SO$_2$Me | OMe | —(CH$_2$)$_2$O(CH$_2$)$_2$— | | |
| 4-131 | SO$_2$Me | NO$_2$ | —(CH$_2$)$_2$O(CH$_2$)$_2$— | | |
| 4-132 | SO$_2$Me | SO$_2$Me | —(CH$_2$)$_2$O(CH$_2$)$_2$— | | |
| 4-133 | Cl | COOMe | Et | Et | |
| 4-134 | Cl | COOMe | —(CH$_2$)$_5$— | | |
| 4-135 | Cl | COOMe | —(CH$_2$)$_2$O(CH$_2$)$_2$— | | |

TABLE 5

Inventive compounds of the general formula (I) in which Q is Q2 and R$^x$ is a methyl group and R'' and W are each hydrogen

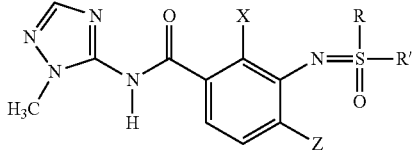
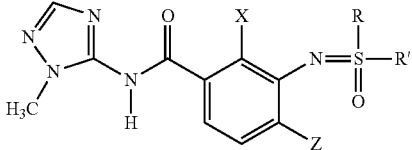

| No. | X | Z | R | R' | Physical data ($^1$H-NMR) |
|---|---|---|---|---|---|
| 5-1 | Me | Me | Et | Et | |
| 5-2 | Me | F | Et | Et | |
| 5-3 | Me | Cl | Et | Et | |
| 5-4 | Me | Br | Et | Et | |
| 5-5 | Me | I | Et | Et | |
| 5-6 | Me | CF$_3$ | Et | Et | |
| 5-7 | Me | CHF$_2$ | Et | Et | |
| 5-8 | Me | CF$_2$Cl | Et | Et | |
| 5-9 | Me | OMe | Et | Et | |
| 5-10 | Me | NO$_2$ | Et | Et | |
| 5-11 | Me | SO$_2$Me | Et | Et | |
| 5-12 | Cl | Me | Et | Et | |
| 5-13 | Cl | F | Et | Et | |
| 5-14 | Cl | Cl | Et | Et | |
| 5-15 | Cl | Br | Et | Et | |
| 5-16 | Cl | I | Et | Et | |
| 5-17 | Cl | CF$_3$ | Et | Et | |
| 5-18 | Cl | CHF$_2$ | Et | Et | |
| 5-19 | Cl | CF$_2$Cl | Et | Et | |
| 5-20 | Cl | OMe | Et | Et | |
| 5-21 | Cl | NO$_2$ | Et | Et | |
| 5-22 | Cl | SO$_2$Me | Et | Et | |
| 5-23 | OMe | Me | Et | Et | |
| 5-24 | OMe | F | Et | Et | |
| 5-25 | OMe | Cl | Et | Et | |
| 5-26 | OMe | Br | Et | Et | |
| 5-27 | OMe | I | Et | Et | |
| 5-28 | OMe | CF$_3$ | Et | Et | |
| 5-29 | OMe | CHF$_2$ | Et | Et | |
| 5-30 | OMe | CF$_2$Cl | Et | Et | |
| 5-31 | OMe | OMe | Et | Et | |
| 5-32 | OMe | NO$_2$ | Et | Et | |
| 5-33 | OMe | SO$_2$Me | Et | Et | |
| 5-34 | SO$_2$Me | Me | Et | Et | |
| 5-35 | SO$_2$Me | F | Et | Et | |
| 5-36 | SO$_2$Me | Cl | Et | Et | |
| 5-37 | SO$_2$Me | Br | Et | Et | |
| 5-38 | SO$_2$Me | I | Et | Et | |
| 5-39 | SO$_2$Me | CF$_3$ | Et | Et | |
| 5-40 | SO$_2$Me | CHF$_2$ | Et | Et | |
| 5-41 | SO$_2$Me | CF$_2$Cl | Et | Et | |
| 5-42 | SO$_2$Me | OMe | Et | Et | |
| 5-43 | SO$_2$Me | NO$_2$ | Et | Et | |
| 5-44 | SO$_2$Me | SO$_2$Me | Et | Et | |
| 5-45 | Me | Me | —(CH$_2$)$_5$— | | |
| 5-46 | Me | F | —(CH$_2$)$_5$— | | |
| 5-47 | Me | Cl | —(CH$_2$)$_5$— | | |
| 5-48 | Me | Br | —(CH$_2$)$_5$— | | |
| 5-49 | Me | I | —(CH$_2$)$_5$— | | |
| 5-50 | Me | CF$_3$ | —(CH$_2$)$_5$— | | |
| 5-51 | Me | CHF$_2$ | —(CH$_2$)$_5$— | | |
| 5-52 | Me | CF$_2$Cl | —(CH$_2$)$_5$— | | |
| 5-53 | Me | OMe | —(CH$_2$)$_5$— | | |
| 5-54 | Me | NO$_2$ | —(CH$_2$)$_5$— | | |
| 5-55 | Me | SO$_2$Me | —(CH$_2$)$_5$— | | |
| 5-56 | Cl | Me | —(CH$_2$)$_5$— | | |
| 5-57 | Cl | F | —(CH$_2$)$_5$— | | |
| 5-58 | Cl | Cl | —(CH$_2$)$_5$— | | |
| 5-59 | Cl | Br | —(CH$_2$)$_5$— | | |
| 5-60 | Cl | I | —(CH$_2$)$_5$— | | |
| 5-61 | Cl | CF$_3$ | —(CH$_2$)$_5$— | | |
| 5-62 | Cl | CHF$_2$ | —(CH$_2$)$_5$— | | |
| 5-63 | Cl | CF$_2$Cl | —(CH$_2$)$_5$— | | |
| 5-64 | Cl | OMe | —(CH$_2$)$_5$— | | |
| 5-65 | Cl | NO$_2$ | —(CH$_2$)$_5$— | | |
| 5-66 | Cl | SO$_2$Me | —(CH$_2$)$_5$— | | |
| 5-67 | OMe | Me | —(CH$_2$)$_5$— | | |
| 5-68 | OMe | F | —(CH$_2$)$_5$— | | |
| 5-69 | OMe | Cl | —(CH$_2$)$_5$— | | |
| 5-70 | OMe | Br | —(CH$_2$)$_5$— | | |
| 5-71 | OMe | I | —(CH$_2$)$_5$— | | |
| 5-72 | OMe | CF$_3$ | —(CH$_2$)$_5$— | | |
| 5-73 | OMe | CHF$_2$ | —(CH$_2$)$_5$— | | |
| 5-74 | OMe | CF$_2$Cl | —(CH$_2$)$_5$— | | |
| 5-75 | OMe | OMe | —(CH$_2$)$_5$— | | |
| 5-76 | OMe | NO$_2$ | —(CH$_2$)$_5$— | | |
| 5-77 | OMe | SO$_2$Me | —(CH$_2$)$_5$— | | |
| 5-78 | SO$_2$Me | Me | —(CH$_2$)$_5$— | | |
| 5-79 | SO$_2$Me | F | —(CH$_2$)$_5$— | | |
| 5-80 | SO$_2$Me | Cl | —(CH$_2$)$_5$— | | |
| 5-81 | SO$_2$Me | Br | —(CH$_2$)$_5$— | | |
| 5-82 | SO$_2$Me | I | —(CH$_2$)$_5$— | | |
| 5-83 | SO$_2$Me | CF$_3$ | —(CH$_2$)$_5$— | | |
| 5-84 | SO$_2$Me | CHF$_2$ | —(CH$_2$)$_5$— | | |
| 5-85 | SO$_2$Me | CF$_2$Cl | —(CH$_2$)$_5$— | | |
| 5-86 | SO$_2$Me | OMe | —(CH$_2$)$_5$— | | |
| 5-87 | SO$_2$Me | NO$_2$ | —(CH$_2$)$_5$— | | |
| 5-88 | SO$_2$Me | SO$_2$Me | —(CH$_2$)$_5$— | | |
| 5-89 | Me | Me | —(CH$_2$)$_2$O(CH$_2$)$_2$— | | |
| 5-90 | Me | F | —(CH$_2$)$_2$O(CH$_2$)$_2$— | | |
| 5-91 | Me | Cl | —(CH$_2$)$_2$O(CH$_2$)$_2$— | | |
| 5-92 | Me | Br | —(CH$_2$)$_2$O(CH$_2$)$_2$— | | |
| 5-93 | Me | I | —(CH$_2$)$_2$O(CH$_2$)$_2$— | | |
| 5-94 | Me | CF$_3$ | —(CH$_2$)$_2$O(CH$_2$)$_2$— | | |
| 5-95 | Me | CHF$_2$ | —(CH$_2$)$_2$O(CH$_2$)$_2$— | | |
| 5-96 | Me | CF$_2$Cl | —(CH$_2$)$_2$O(CH$_2$)$_2$— | | |
| 5-97 | Me | OMe | —(CH$_2$)$_2$O(CH$_2$)$_2$— | | |
| 5-98 | Me | NO$_2$ | —(CH$_2$)$_2$O(CH$_2$)$_2$— | | |
| 5-99 | Me | SO$_2$Me | —(CH$_2$)$_2$O(CH$_2$)$_2$— | | |
| 5-100 | Cl | Me | —(CH$_2$)$_2$O(CH$_2$)$_2$— | | |
| 5-101 | Cl | F | —(CH$_2$)$_2$O(CH$_2$)$_2$— | | |
| 5-102 | Cl | Cl | —(CH$_2$)$_2$O(CH$_2$)$_2$— | | |
| 5-103 | Cl | Br | —(CH$_2$)$_2$O(CH$_2$)$_2$— | | |
| 5-104 | Cl | I | —(CH$_2$)$_2$O(CH$_2$)$_2$— | | |
| 5-105 | Cl | CF$_3$ | —(CH$_2$)$_2$O(CH$_2$)$_2$— | | |
| 5-106 | Cl | CHF$_2$ | —(CH$_2$)$_2$O(CH$_2$)$_2$— | | |
| 5-107 | Cl | CF$_2$Cl | —(CH$_2$)$_2$O(CH$_2$)$_2$— | | |
| 5-108 | Cl | OMe | —(CH$_2$)$_2$O(CH$_2$)$_2$— | | |
| 5-109 | Cl | NO$_2$ | —(CH$_2$)$_2$O(CH$_2$)$_2$— | | |
| 5-110 | Cl | SO$_2$Me | —(CH$_2$)$_2$O(CH$_2$)$_2$— | | |
| 5-111 | OMe | Me | —(CH$_2$)$_2$O(CH$_2$)$_2$— | | |
| 5-112 | OMe | F | —(CH$_2$)$_2$O(CH$_2$)$_2$— | | |
| 5-113 | OMe | Cl | —(CH$_2$)$_2$O(CH$_2$)$_2$— | | |
| 5-114 | OMe | Br | —(CH$_2$)$_2$O(CH$_2$)$_2$— | | |
| 5-115 | OMe | I | —(CH$_2$)$_2$O(CH$_2$)$_2$— | | |
| 5-116 | OMe | CF$_3$ | —(CH$_2$)$_2$O(CH$_2$)$_2$— | | |
| 5-117 | OMe | CHF$_2$ | —(CH$_2$)$_2$O(CH$_2$)$_2$— | | |
| 5-118 | OMe | CF$_2$Cl | —(CH$_2$)$_2$O(CH$_2$)$_2$— | | |
| 5-119 | OMe | OMe | —(CH$_2$)$_2$O(CH$_2$)$_2$— | | |
| 5-120 | OMe | NO$_2$ | —(CH$_2$)$_2$O(CH$_2$)$_2$— | | |
| 5-121 | OMe | SO$_2$Me | —(CH$_2$)$_2$O(CH$_2$)$_2$— | | |
| 5-122 | SO$_2$Me | Me | —(CH$_2$)$_2$O(CH$_2$)$_2$— | | |
| 5-123 | SO$_2$Me | F | —(CH$_2$)$_2$O(CH$_2$)$_2$— | | |
| 5-124 | SO$_2$Me | Cl | —(CH$_2$)$_2$O(CH$_2$)$_2$— | | |
| 5-125 | SO$_2$Me | Br | —(CH$_2$)$_2$O(CH$_2$)$_2$— | | |
| 5-126 | SO$_2$Me | I | —(CH$_2$)$_2$O(CH$_2$)$_2$— | | |
| 5-127 | SO$_2$Me | CF$_3$ | —(CH$_2$)$_2$O(CH$_2$)$_2$— | | |
| 5-128 | SO$_2$Me | CHF$_2$ | —(CH$_2$)$_2$O(CH$_2$)$_2$— | | |

TABLE 5-continued

Inventive compounds of the general formula (I) in which Q is Q2 and $R^x$ is a methyl group and R" and W are each hydrogen

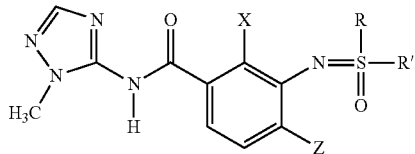

| No. | X | Z | R | R' | Physical data ($^1$H-NMR) |
|---|---|---|---|---|---|
| 5-129 | SO$_2$Me | CF$_2$Cl | —(CH$_2$)$_2$O(CH$_2$)$_2$— | | |
| 5-130 | SO$_2$Me | OMe | —(CH$_2$)$_2$O(CH$_2$)$_2$— | | |
| 5-131 | SO$_2$Me | NO$_2$ | —(CH$_2$)$_2$O(CH$_2$)$_2$— | | |
| 5-132 | SO$_2$Me | SO$_2$Me | —(CH$_2$)$_2$O(CH$_2$)$_2$— | | |

TABLE 5-continued

Inventive compounds of the general formula (I) in which Q is Q2 and $R^x$ is a methyl group and R" and W are each hydrogen

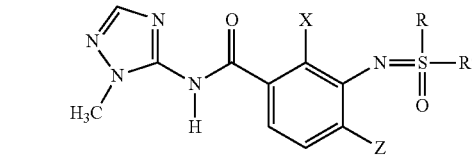

| No. | X | Z | R | R' | Physical data ($^1$H-NMR) |
|---|---|---|---|---|---|
| 5-133 | Cl | COOMe | Et | Et | |
| 5-134 | Cl | COOMe | —(CH$_2$)$_5$— | | |
| 5-135 | Cl | COOMe | —(CH$_2$)$_2$O(CH$_2$)$_2$— | | |

TABLE 6

Inventive compounds of the general formula (I) in which Q is Q3 and $R^y$ is a methyl group and R" and W are each hydrogen

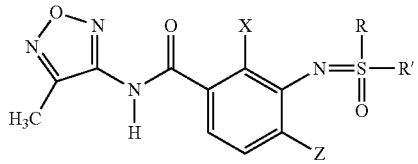

| No. | X | Z | R | R' | Physical data ($^1$H-NMR) |
|---|---|---|---|---|---|
| 6-1 | Me | Me | Et | Et | |
| 6-2 | Me | F | Et | Et | |
| 6-3 | Me | Cl | Et | Et | |
| 6-4 | Me | Br | Et | Et | |
| 6-5 | Me | I | Et | Et | |
| 6-6 | Me | CF$_3$ | Et | Et | |
| 6-7 | Me | CHF$_2$ | Et | Et | |
| 6-8 | Me | CF$_2$Cl | Et | Et | |
| 6-9 | Me | OMe | Et | Et | |
| 6-10 | Me | NO$_2$ | Et | Et | |
| 6-11 | Me | SO$_2$Me | Et | Et | |
| 6-12 | Cl | Me | Et | Et | |
| 6-13 | Cl | F | Et | Et | |
| 6-14 | Cl | Cl | Et | Et | (400 MHz, CDCl$_3$ δ, ppm) 7.37 (d, 1H), 7.25 (d, 1H), 3.30 (q, 4H), 2.48 (s, 3H), 1.47 (t, 6H) |
| 6-15 | Cl | Br | Et | Et | |
| 6-16 | Cl | I | Et | Et | |
| 6-17 | Cl | CF$_3$ | Et | Et | |
| 6-18 | Cl | CHF$_2$ | Et | Et | |
| 6-19 | Cl | CF$_2$Cl | Et | Et | |
| 6-20 | Cl | OMe | Et | Et | |
| 6-21 | Cl | NO$_2$ | Et | Et | |
| 6-22 | Cl | SO$_2$Me | Et | Et | |
| 6-23 | OMe | Me | Et | Et | |
| 6-24 | OMe | F | Et | Et | |
| 6-25 | OMe | Cl | Et | Et | |
| 6-26 | OMe | Br | Et | Et | |
| 6-27 | OMe | I | Et | Et | |
| 6-28 | OMe | CF$_3$ | Et | Et | |
| 6-29 | OMe | CHF$_2$ | Et | Et | |
| 6-30 | OMe | CF$_2$Cl | Et | Et | |
| 6-31 | OMe | OMe | Et | Et | |
| 6-32 | OMe | NO$_2$ | Et | Et | |
| 6-33 | OMe | SO$_2$Me | Et | Et | |
| 6-34 | SO$_2$Me | Me | Et | Et | |
| 6-35 | SO$_2$Me | F | Et | Et | |
| 6-36 | SO$_2$Me | Cl | Et | Et | |
| 6-37 | SO$_2$Me | Br | Et | Et | |
| 6-38 | SO$_2$Me | I | Et | Et | |
| 6-39 | SO$_2$Me | CF$_3$ | Et | Et | |
| 6-40 | SO$_2$Me | CHF$_2$ | Et | Et | |

TABLE 6-continued

Inventive compounds of the general formula (I) in which Q is Q3 and R<sup>y</sup> is a methyl group and R'' and W are each hydrogen

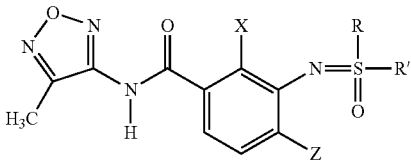

| No. | X | Z | R | R' | Physical data ($^1$H-NMR) |
|---|---|---|---|---|---|
| 6-41 | SO$_2$Me | CF$_2$Cl | Et | Et | |
| 6-42 | SO$_2$Me | OMe | Et | Et | |
| 6-43 | SO$_2$Me | NO$_2$ | Et | Et | |
| 6-44 | SO$_2$Me | SO$_2$Me | Et | Et | |
| 6-45 | Me | Me | —(CH$_2$)$_5$— | | |
| 6-46 | Me | F | —(CH$_2$)$_5$— | | |
| 6-47 | Me | Cl | —(CH$_2$)$_5$— | | |
| 6-48 | Me | Br | —(CH$_2$)$_5$— | | |
| 6-49 | Me | I | —(CH$_2$)$_5$— | | |
| 6-50 | Me | CF$_3$ | —(CH$_2$)$_5$— | | |
| 6-51 | Me | CHF$_2$ | —(CH$_2$)$_5$— | | |
| 6-52 | Me | CF$_2$Cl | —(CH$_2$)$_5$— | | |
| 6-53 | Me | OMe | —(CH$_2$)$_5$— | | |
| 6-54 | Me | NO$_2$ | —(CH$_2$)$_5$— | | |
| 6-55 | Me | SO$_2$Me | —(CH$_2$)$_5$— | | |
| 6-56 | Cl | Me | —(CH$_2$)$_5$— | | |
| 6-57 | Cl | F | —(CH$_2$)$_5$— | | |
| 6-58 | Cl | Cl | —(CH$_2$)$_5$— | | (400 MHz, DMSO-d$_6$ δ, ppm) 7.54 (d, 1H), 7.26 (d, 1H), 3.43-3.26 (m, 4H), 2.38 (s, 3H), 2.13-2.05 (m, 2H), 1.94 (m, 2H), 1.62 (m, 2H) |
| 6-59 | Cl | Br | —(CH$_2$)$_5$— | | |
| 6-60 | Cl | I | —(CH$_2$)$_5$— | | |
| 6-61 | Cl | CF$_3$ | —(CH$_2$)$_5$— | | |
| 6-62 | Cl | CHF$_2$ | —(CH$_2$)$_5$— | | |
| 6-63 | Cl | CF$_2$Cl | —(CH$_2$)$_5$— | | |
| 6-64 | Cl | OMe | —(CH$_2$)$_5$— | | |
| 6-65 | Cl | NO$_2$ | —(CH$_2$)$_5$— | | |
| 6-66 | Cl | SO$_2$Me | —(CH$_2$)$_5$— | | |
| 6-67 | OMe | Me | —(CH$_2$)$_5$— | | |
| 6-68 | OMe | F | —(CH$_2$)$_5$— | | |
| 6-69 | OMe | Cl | —(CH$_2$)$_5$— | | |
| 6-70 | OMe | Br | —(CH$_2$)$_5$— | | |
| 6-71 | OMe | I | —(CH$_2$)$_5$— | | |
| 6-72 | OMe | CF$_3$ | —(CH$_2$)$_5$— | | |
| 6-73 | OMe | CHF$_2$ | —(CH$_2$)$_5$— | | |
| 6-74 | OMe | CF$_2$Cl | —(CH$_2$)$_5$— | | |
| 6-75 | OMe | OMe | —(CH$_2$)$_5$— | | |
| 6-76 | OMe | NO$_2$ | —(CH$_2$)$_5$— | | |
| 6-77 | OMe | SO$_2$Me | —(CH$_2$)$_5$— | | |
| 6-78 | SO$_2$Me | Me | —(CH$_2$)$_5$— | | |
| 6-79 | SO$_2$Me | F | —(CH$_2$)$_5$— | | |
| 6-80 | SO$_2$Me | Cl | —(CH$_2$)$_5$— | | |
| 6-81 | SO$_2$Me | Br | —(CH$_2$)$_5$— | | |
| 6-82 | SO$_2$Me | I | —(CH$_2$)$_5$— | | |
| 6-83 | SO$_2$Me | CF$_3$ | —(CH$_2$)$_5$— | | |
| 6-84 | SO$_2$Me | CHF$_2$ | —(CH$_2$)$_5$— | | |
| 6-85 | SO$_2$Me | CF$_2$Cl | —(CH$_2$)$_5$— | | |
| 6-86 | SO$_2$Me | OMe | —(CH$_2$)$_5$— | | |
| 6-87 | SO$_2$Me | NO$_2$ | —(CH$_2$)$_5$— | | |
| 6-88 | SO$_2$Me | SO$_2$Me | —(CH$_2$)$_5$— | | |
| 6-89 | Me | Me | —(CH$_2$)$_2$O(CH$_2$)$_2$— | | |
| 6-90 | Me | F | —(CH$_2$)$_2$O(CH$_2$)$_2$— | | |
| 6-91 | Me | Cl | —(CH$_2$)$_2$O(CH$_2$)$_2$— | | |
| 6-92 | Me | Br | —(CH$_2$)$_2$O(CH$_2$)$_2$— | | |
| 6-93 | Me | I | —(CH$_2$)$_2$O(CH$_2$)$_2$— | | |
| 6-94 | Me | CF$_3$ | —(CH$_2$)$_2$O(CH$_2$)$_2$— | | |
| 6-95 | Me | CHF$_2$ | —(CH$_2$)$_2$O(CH$_2$)$_2$— | | |
| 6-96 | Me | CF$_2$Cl | —(CH$_2$)$_2$O(CH$_2$)$_2$— | | |
| 6-97 | Me | OMe | —(CH$_2$)$_2$O(CH$_2$)$_2$— | | |
| 6-98 | Me | NO$_2$ | —(CH$_2$)$_2$O(CH$_2$)$_2$— | | |
| 6-99 | Me | SO$_2$Me | —(CH$_2$)$_2$O(CH$_2$)$_2$— | | |
| 6-100 | Cl | Me | —(CH$_2$)$_2$O(CH$_2$)$_2$— | | |

TABLE 6-continued

Inventive compounds of the general formula (I) in which Q is Q3 and $R^y$ is a methyl group and R" and W are each hydrogen

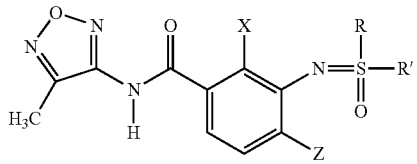

| No. | X | Z | R | R' | Physical data ($^1$H-NMR) |
|---|---|---|---|---|---|
| 6-101 | Cl | F | —(CH$_2$)$_2$O(CH$_2$)$_2$— | | |
| 6-102 | Cl | Cl | —(CH$_2$)$_2$O(CH$_2$)$_2$— | | (400 MHz, CDCl$_3$ δ, ppm) 7.44 (d, 1H), 7.37 (d, 1H), 4.35-4.31 (m, 2H), 4.21-4.15 (m, 2H), 3.55 (m, 2H), 3.31 (m, 2H), 2.49 (s, 3H) |
| 6-103 | Cl | Br | —(CH$_2$)$_2$O(CH$_2$)$_2$— | | |
| 6-104 | Cl | I | —(CH$_2$)$_2$O(CH$_2$)$_2$— | | |
| 6-105 | Cl | CF$_3$ | —(CH$_2$)$_2$O(CH$_2$)$_2$— | | |
| 6-106 | Cl | CHF$_2$ | —(CH$_2$)$_2$O(CH$_2$)$_2$— | | |
| 6-107 | Cl | CF$_2$Cl | —(CH$_2$)$_2$O(CH$_2$)$_2$— | | |
| 6-108 | Cl | OMe | —(CH$_2$)$_2$O(CH$_2$)$_2$— | | |
| 6-109 | Cl | NO$_2$ | —(CH$_2$)$_2$O(CH$_2$)$_2$— | | |
| 6-110 | Cl | SO$_2$Me | —(CH$_2$)$_2$O(CH$_2$)$_2$— | | |
| 6-111 | OMe | Me | —(CH$_2$)$_2$O(CH$_2$)$_2$— | | |
| 6-112 | OMe | F | —(CH$_2$)$_2$O(CH$_2$)$_2$— | | |
| 6-113 | OMe | Cl | —(CH$_2$)$_2$O(CH$_2$)$_2$— | | |
| 6-114 | OMe | Br | —(CH$_2$)$_2$O(CH$_2$)$_2$— | | |
| 6-115 | OMe | I | —(CH$_2$)$_2$O(CH$_2$)$_2$— | | |
| 6-116 | OMe | CF$_3$ | —(CH$_2$)$_2$O(CH$_2$)$_2$— | | |
| 6-117 | OMe | CHF$_2$ | —(CH$_2$)$_2$O(CH$_2$)$_2$— | | |
| 6-118 | OMe | CF$_2$Cl | —(CH$_2$)$_2$O(CH$_2$)$_2$— | | |
| 6-119 | OMe | OMe | —(CH$_2$)$_2$O(CH$_2$)$_2$— | | |
| 6-120 | OMe | NO$_2$ | —(CH$_2$)$_2$O(CH$_2$)$_2$— | | |
| 6-121 | OMe | SO$_2$Me | —(CH$_2$)$_2$O(CH$_2$)$_2$— | | |
| 6-122 | SO$_2$Me | Me | —(CH$_2$)$_2$O(CH$_2$)$_2$— | | |
| 6-123 | SO$_2$Me | F | —(CH$_2$)$_2$O(CH$_2$)$_2$— | | |
| 6-124 | SO$_2$Me | Cl | —(CH$_2$)$_2$O(CH$_2$)$_2$— | | |
| 6-125 | SO$_2$Me | Br | —(CH$_2$)$_2$O(CH$_2$)$_2$— | | |
| 6-126 | SO$_2$Me | I | —(CH$_2$)$_2$O(CH$_2$)$_2$— | | |
| 6-127 | SO$_2$Me | CF$_3$ | —(CH$_2$)$_2$O(CH$_2$)$_2$— | | |
| 6-128 | SO$_2$Me | CHF$_2$ | —(CH$_2$)$_2$O(CH$_2$)$_2$— | | |
| 6-129 | SO$_2$Me | CF$_2$Cl | —(CH$_2$)$_2$O(CH$_2$)$_2$— | | |
| 6-130 | SO$_2$Me | OMe | —(CH$_2$)$_2$O(CH$_2$)$_2$— | | |
| 6-131 | SO$_2$Me | NO$_2$ | —(CH$_2$)$_2$O(CH$_2$)$_2$— | | |
| 6-132 | SO$_2$Me | SO$_2$Me | —(CH$_2$)$_2$O(CH$_2$)$_2$— | | |
| 6-133 | Cl | COOMe | Et | Et | |
| 6-134 | Cl | COOMe | —(CH$_2$)$_5$— | | |
| 6-135 | Cl | COOMe | —(CH$_2$)$_2$O(CH$_2$)$_2$— | | |

TABLE 7

Inventive compounds of the general formula (I) in which Q is Q4 and $R^z$ is a methyl group and R" and W are each hydrogen

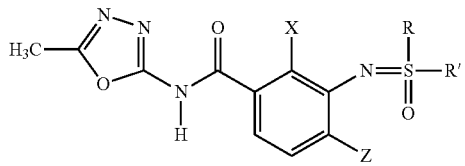

| No. | X | Z | R | R' | Physical data ($^1$H-NMR) |
|---|---|---|---|---|---|
| 7-1 | Me | Me | Et | Et | |
| 7-2 | Me | F | Et | Et | |
| 7-3 | Me | Cl | Et | Et | |
| 7-4 | Me | Br | Et | Et | |
| 7-5 | Me | I | Et | Et | |
| 7-6 | Me | CF$_3$ | Et | Et | |
| 7-7 | Me | CHF$_2$ | Et | Et | |
| 7-8 | Me | CF$_2$Cl | Et | Et | |
| 7-9 | Me | OMe | Et | Et | |

TABLE 7-continued

Inventive compounds of the general formula (I) in which Q is Q4 and $R^z$ is a methyl group and R" and W are each hydrogen

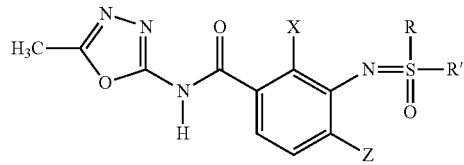

| No. | X | Z | R | R' | Physical data ($^1$H-NMR) |
|---|---|---|---|---|---|
| 7-10 | Me | $NO_2$ | Et | Et | |
| 7-11 | Me | $SO_2Me$ | Et | Et | |
| 7-12 | Cl | Me | Et | Et | |
| 7-13 | Cl | F | Et | Et | |
| 7-14 | Cl | Cl | Et | Et | (400 MHz, $CDCl_3$ δ, ppm) 7.39 (d, 1H), 7.31 (d, 1H), 3.31 (q, 4H), 2.55 (s, 3H), 1.49 (t, 6H) |
| 7-15 | Cl | Br | Et | Et | |
| 7-16 | Cl | I | Et | Et | |
| 7-17 | Cl | $CF_3$ | Et | Et | |
| 7-18 | Cl | $CHF_2$ | Et | Et | |
| 7-19 | Cl | $CF_2Cl$ | Et | Et | |
| 7-20 | Cl | OMe | Et | Et | |
| 7-21 | Cl | $NO_2$ | Et | Et | |
| 7-22 | Cl | $SO_2Me$ | Et | Et | |
| 7-23 | OMe | Me | Et | Et | |
| 7-24 | OMe | F | Et | Et | |
| 7-25 | OMe | Cl | Et | Et | |
| 7-26 | OMe | Br | Et | Et | |
| 7-27 | OMe | I | Et | Et | |
| 7-28 | OMe | $CF_3$ | Et | Et | |
| 7-29 | OMe | $CHF_2$ | Et | Et | |
| 7-30 | OMe | $CF_2Cl$ | Et | Et | |
| 7-31 | OMe | OMe | Et | Et | |
| 7-32 | OMe | $NO_2$ | Et | Et | |
| 7-33 | OMe | $SO_2Me$ | Et | Et | |
| 7-34 | $SO_2Me$ | Me | Et | Et | |
| 7-35 | $SO_2Me$ | F | Et | Et | |
| 7-36 | $SO_2Me$ | Cl | Et | Et | |
| 7-37 | $SO_2Me$ | Br | Et | Et | |
| 7-38 | $SO_2Me$ | I | Et | Et | |
| 7-39 | $SO_2Me$ | $CF_3$ | Et | Et | |
| 7-40 | $SO_2Me$ | $CHF_2$ | Et | Et | |
| 7-41 | $SO_2Me$ | $CF_2Cl$ | Et | Et | |
| 7-42 | $SO_2Me$ | OMe | Et | Et | |
| 7-43 | $SO_2Me$ | $NO_2$ | Et | Et | |
| 7-44 | $SO_2Me$ | $SO_2Me$ | Et | Et | |
| 7-45 | Me | Me | —$(CH_2)_5$— | | |
| 7-46 | Me | F | —$(CH_2)_5$— | | |
| 7-47 | Me | Cl | —$(CH_2)_5$— | | |
| 7-48 | Me | Br | —$(CH_2)_5$— | | |
| 7-49 | Me | I | —$(CH_2)_5$— | | |
| 7-50 | Me | $CF_3$ | —$(CH_2)_5$— | | |
| 7-51 | Me | $CHF_2$ | —$(CH_2)_5$— | | |
| 7-52 | Me | $CF_2Cl$ | —$(CH_2)_5$— | | |
| 7-53 | Me | OMe | —$(CH_2)_5$— | | |
| 7-54 | Me | $NO_2$ | —$(CH_2)_5$— | | |
| 7-55 | Me | $SO_2Me$ | —$(CH_2)_5$— | | |
| 7-56 | Cl | Me | —$(CH_2)_5$— | | |
| 7-57 | Cl | F | —$(CH_2)_5$— | | |
| 7-58 | Cl | Cl | —$(CH_2)_5$— | | (400 MHz, $CDCl_3$ δ, ppm) 7.35 (d, 1H), 3.49 (m, 2H), 3.33-3.23 (m, 2H), 2.57 (s, 3H) |
| 7-59 | Cl | Br | —$(CH_2)_5$— | | |
| 7-60 | Cl | I | —$(CH_2)_5$— | | |
| 7-61 | Cl | $CF_3$ | —$(CH_2)_5$— | | |
| 7-62 | Cl | $CHF_2$ | —$(CH_2)_5$— | | |
| 7-63 | Cl | $CF_2Cl$ | —$(CH_2)_5$— | | |
| 7-64 | Cl | OMe | —$(CH_2)_5$— | | |
| 7-65 | Cl | $NO_2$ | —$(CH_2)_5$— | | |
| 7-66 | Cl | $SO_2Me$ | —$(CH_2)_5$— | | |
| 7-67 | OMe | Me | —$(CH_2)_5$— | | |
| 7-68 | OMe | F | —$(CH_2)_5$— | | |
| 7-69 | OMe | Cl | —$(CH_2)_5$— | | |
| 7-70 | OMe | Br | —$(CH_2)_5$— | | |
| 7-71 | OMe | I | —$(CH_2)_5$— | | |
| 7-72 | OMe | $CF_3$ | —$(CH_2)_5$— | | |
| 7-73 | OMe | $CHF_2$ | —$(CH_2)_5$— | | |

TABLE 7-continued

Inventive compounds of the general formula (I) in which Q is Q4 and $R^z$ is a methyl group and R" and W are each hydrogen

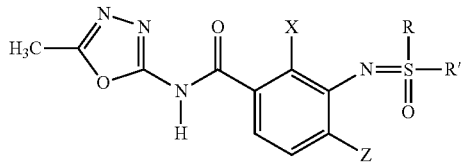

| No. | X | Z | R | R' | Physical data ($^1$H-NMR) |
|---|---|---|---|---|---|
| 7-74 | OMe | CF$_2$Cl | —(CH$_2$)$_5$— | | |
| 7-75 | OMe | OMe | —(CH$_2$)$_5$— | | |
| 7-76 | OMe | NO$_2$ | —(CH$_2$)$_5$— | | |
| 7-77 | OMe | SO$_2$Me | —(CH$_2$)$_5$— | | |
| 7-78 | SO$_2$Me | Me | —(CH$_2$)$_5$— | | |
| 7-79 | SO$_2$Me | F | —(CH$_2$)$_5$— | | |
| 7-80 | SO$_2$Me | Cl | —(CH$_2$)$_5$— | | |
| 7-81 | SO$_2$Me | Br | —(CH$_2$)$_5$— | | |
| 7-82 | SO$_2$Me | I | —(CH$_2$)$_5$— | | |
| 7-83 | SO$_2$Me | CF$_3$ | —(CH$_2$)$_5$— | | |
| 7-84 | SO$_2$Me | CHF$_2$ | —(CH$_2$)$_5$— | | |
| 7-85 | SO$_2$Me | CF$_2$Cl | —(CH$_2$)$_5$— | | |
| 7-86 | SO$_2$Me | OMe | —(CH$_2$)$_5$— | | |
| 7-87 | SO$_2$Me | NO$_2$ | —(CH$_2$)$_5$— | | |
| 7-88 | SO$_2$Me | SO$_2$Me | —(CH$_2$)$_5$— | | |
| 7-89 | Me | Me | —(CH$_2$)$_2$O(CH$_2$)$_2$— | | |
| 7-90 | Me | F | —(CH$_2$)$_2$O(CH$_2$)$_2$— | | |
| 7-91 | Me | Cl | —(CH$_2$)$_2$O(CH$_2$)$_2$— | | |
| 7-92 | Me | Br | —(CH$_2$)$_2$O(CH$_2$)$_2$— | | |
| 7-93 | Me | I | —(CH$_2$)$_2$O(CH$_2$)$_2$— | | |
| 7-94 | Me | CF$_3$ | —(CH$_2$)$_2$O(CH$_2$)$_2$— | | |
| 7-95 | Me | CHF$_2$ | —(CH$_2$)$_2$O(CH$_2$)$_2$— | | |
| 7-96 | Me | CF$_2$Cl | —(CH$_2$)$_2$O(CH$_2$)$_2$— | | |
| 7-97 | Me | OMe | —(CH$_2$)$_2$O(CH$_2$)$_2$— | | |
| 7-98 | Me | NO$_2$ | —(CH$_2$)$_2$O(CH$_2$)$_2$— | | |
| 7-99 | Me | SO$_2$Me | —(CH$_2$)$_2$O(CH$_2$)$_2$— | | |
| 7-100 | Cl | Me | —(CH$_2$)$_2$O(CH$_2$)$_2$— | | |
| 7-101 | Cl | F | —(CH$_2$)$_2$O(CH$_2$)$_2$— | | |
| 7-102 | Cl | Cl | —(CH$_2$)$_2$O(CH$_2$)$_2$— | | (400 MHz, CDCl$_3$ δ, ppm) 7.41 (d, 1H), 7.36 (d, 1H), 4.32 (m, 2H), 4.19 (m, 2H), 3.57 (m, 2H), 3.31 (m, 2H), 2.55 (s, 3H) |
| 7-103 | Cl | Br | —(CH$_2$)$_2$O(CH$_2$)$_2$— | | |
| 7-104 | Cl | I | —(CH$_2$)$_2$O(CH$_2$)$_2$— | | |
| 7-105 | Cl | CF$_3$ | —(CH$_2$)$_2$O(CH$_2$)$_2$— | | |
| 7-106 | Cl | CHF$_2$ | —(CH$_2$)$_2$O(CH$_2$)$_2$— | | |
| 7-107 | Cl | CF$_2$Cl | —(CH$_2$)$_2$O(CH$_2$)$_2$— | | |
| 7-108 | Cl | OMe | —(CH$_2$)$_2$O(CH$_2$)$_2$— | | |
| 7-109 | Cl | NO$_2$ | —(CH$_2$)$_2$O(CH$_2$)$_2$— | | |
| 7-110 | Cl | SO$_2$Me | —(CH$_2$)$_2$O(CH$_2$)$_2$— | | |
| 7-111 | OMe | Me | —(CH$_2$)$_2$O(CH$_2$)$_2$— | | |
| 7-112 | OMe | F | —(CH$_2$)$_2$O(CH$_2$)$_2$— | | |
| 7-113 | OMe | Cl | —(CH$_2$)$_2$O(CH$_2$)$_2$— | | |
| 7-114 | OMe | Br | —(CH$_2$)$_2$O(CH$_2$)$_2$— | | |
| 7-115 | OMe | I | —(CH$_2$)$_2$O(CH$_2$)$_2$— | | |
| 7-116 | OMe | CF$_3$ | —(CH$_2$)$_2$O(CH$_2$)$_2$— | | |
| 7-117 | OMe | CHF$_2$ | —(CH$_2$)$_2$O(CH$_2$)$_2$— | | |
| 7-118 | OMe | CF$_2$Cl | —(CH$_2$)$_2$O(CH$_2$)$_2$— | | |
| 7-119 | OMe | OMe | —(CH$_2$)$_2$O(CH$_2$)$_2$— | | |
| 7-120 | OMe | NO$_2$ | —(CH$_2$)$_2$O(CH$_2$)$_2$— | | |
| 7-121 | OMe | SO$_2$Me | —(CH$_2$)$_2$O(CH$_2$)$_2$— | | |
| 7-122 | SO$_2$Me | Me | —(CH$_2$)$_2$O(CH$_2$)$_2$— | | |
| 7-123 | SO$_2$Me | F | —(CH$_2$)$_2$O(CH$_2$)$_2$— | | |
| 7-124 | SO$_2$Me | Cl | —(CH$_2$)$_2$O(CH$_2$)$_2$— | | |
| 7-125 | SO$_2$Me | Br | —(CH$_2$)$_2$O(CH$_2$)$_2$— | | |
| 7-126 | SO$_2$Me | I | —(CH$_2$)$_2$O(CH$_2$)$_2$— | | |
| 7-127 | SO$_2$Me | CF$_3$ | —(CH$_2$)$_2$O(CH$_2$)$_2$— | | |
| 7-128 | SO$_2$Me | CHF$_2$ | —(CH$_2$)$_2$O(CH$_2$)$_2$— | | |
| 7-129 | SO$_2$Me | CF$_2$Cl | —(CH$_2$)$_2$O(CH$_2$)$_2$— | | |
| 7-130 | SO$_2$Me | OMe | —(CH$_2$)$_2$O(CH$_2$)$_2$— | | |
| 7-131 | SO$_2$Me | NO$_2$ | —(CH$_2$)$_2$O(CH$_2$)$_2$— | | |
| 7-132 | SO$_2$Me | SO$_2$Me | —(CH$_2$)$_2$O(CH$_2$)$_2$— | | |
| 7-133 | Cl | COOMe | Et | Et | |
| 7-134 | Cl | COOMe | —(CH$_2$)$_5$— | | |
| 7-135 | Cl | COOMe | —(CH$_2$)$_2$O(CH$_2$)$_2$— | | |

TABLE 8

Inventive compounds of the general formula (I) in the form of the sodium salts, in which Q is Q1 and R$^x$ is a methyl group and W is hydrogen

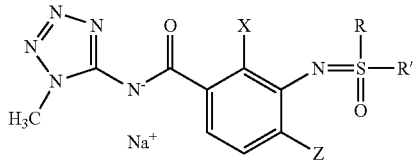

| No. | X | Z | R | R' | Physical data ($^1$H-NMR) |
|---|---|---|---|---|---|
| 8-1 | Me | Me | Et | Et | |
| 8-2 | Me | Cl | Et | Et | |
| 8-3 | Me | CF$_3$ | Et | Et | |
| 8-4 | Me | CHF$_2$ | Et | Et | |
| 8-5 | Cl | Me | Et | Et | |
| 8-6 | Cl | Cl | Et | Et | |
| 8-7 | Cl | CF$_3$ | Et | Et | |
| 8-8 | Cl | CHF$_2$ | Et | Et | |
| 8-9 | OMe | Me | Et | Et | |
| 8-10 | OMe | Cl | Et | Et | |
| 8-11 | OMe | CF$_3$ | Et | Et | |
| 8-12 | OMe | CHF$_2$ | Et | Et | |
| 8-13 | SO$_2$Me | Me | Et | Et | |
| 8-14 | SO$_2$Me | Cl | Et | Et | |
| 8-15 | SO$_2$Me | CF$_3$ | Et | Et | |
| 8-16 | SO$_2$Me | CHF$_2$ | Et | Et | |
| 8-17 | Me | Me | —(CH$_2$)$_5$— | | |
| 8-18 | Me | Cl | —(CH$_2$)$_5$— | | |
| 8-19 | Me | CF$_3$ | —(CH$_2$)$_5$— | | |
| 8-20 | Me | CHF$_2$ | —(CH$_2$)$_5$— | | |
| 8-21 | Cl | Me | —(CH$_2$)$_5$— | | |
| 8-22 | Cl | Cl | —(CH$_2$)$_5$— | | |
| 8-23 | Cl | CF$_3$ | —(CH$_2$)$_5$— | | |
| 8-24 | Cl | CHF$_2$ | —(CH$_2$)$_5$— | | |
| 8-25 | OMe | Me | —(CH$_2$)$_5$— | | |
| 8-26 | OMe | Cl | —(CH$_2$)$_5$— | | |

TABLE 8-continued

Inventive compounds of the general formula (I) in the form of the sodium salts, in which Q is Q1 and R$^x$ is a methyl group and W is hydrogen

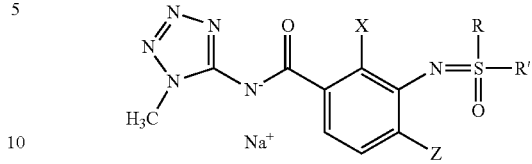

| No. | X | Z | R | R' | Physical data ($^1$H-NMR) |
|---|---|---|---|---|---|
| 8-27 | OMe | CF$_3$ | —(CH$_2$)$_5$— | | |
| 8-28 | OMe | CHF$_2$ | —(CH$_2$)$_5$— | | |
| 8-29 | SO$_2$Me | Me | —(CH$_2$)$_5$— | | |
| 8-30 | SO$_2$Me | Cl | —(CH$_2$)$_5$— | | |
| 8-31 | SO$_2$Me | CF$_3$ | —(CH$_2$)$_5$— | | |
| 8-32 | SO$_2$Me | CHF$_2$ | —(CH$_2$)$_5$— | | |
| 8-33 | Me | Me | —(CH$_2$)$_2$O(CH$_2$)$_2$— | | |
| 8-34 | Me | Cl | —(CH$_2$)$_2$O(CH$_2$)$_2$— | | |
| 8-35 | Me | CF$_3$ | —(CH$_2$)$_2$O(CH$_2$)$_2$— | | |
| 8-36 | Me | CHF$_2$ | —(CH$_2$)$_2$O(CH$_2$)$_2$— | | |
| 8-37 | Cl | Me | —(CH$_2$)$_2$O(CH$_2$)$_2$— | | |
| 8-38 | Cl | Cl | —(CH$_2$)$_2$O(CH$_2$)$_2$— | | |
| 8-39 | Cl | CF$_3$ | —(CH$_2$)$_2$O(CH$_2$)$_2$— | | |
| 8-40 | Cl | CHF$_2$ | —(CH$_2$)$_2$O(CH$_2$)$_2$— | | |
| 8-41 | OMe | Me | —(CH$_2$)$_2$O(CH$_2$)$_2$— | | |
| 8-42 | OMe | Cl | —(CH$_2$)$_2$O(CH$_2$)$_2$— | | |
| 8-43 | OMe | CF$_3$ | —(CH$_2$)$_2$O(CH$_2$)$_2$— | | |
| 8-44 | OMe | CHF$_2$ | —(CH$_2$)$_2$O(CH$_2$)$_2$— | | |
| 8-45 | SO$_2$Me | Me | —(CH$_2$)$_2$O(CH$_2$)$_2$— | | |
| 8-46 | SO$_2$Me | Cl | —(CH$_2$)$_2$O(CH$_2$)$_2$— | | |
| 8-47 | SO$_2$Me | CF$_3$ | —(CH$_2$)$_2$O(CH$_2$)$_2$— | | |
| 8-48 | SO$_2$Me | CHF$_2$ | —(CH$_2$)$_2$O(CH$_2$)$_2$— | | |
| 8-49 | Cl | COOMe | Et | Et | |
| 8-50 | Cl | COOMe | —(CH$_2$)$_5$— | | |
| 8-51 | Cl | COOMe | —(CH$_2$)$_2$O(CH$_2$)$_2$— | | |

TABLE 9

Inventive compounds of the general formula (I) in which Q is Q3 and R$^y$ is chlorine and R'' and W are each hydrogen

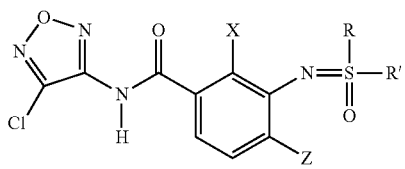

| No. | X | Z | R | R' | Physical data ($^1$H-NMR) |
|---|---|---|---|---|---|
| 9-1 | Me | Me | Et | Et | |
| 9-2 | Me | F | Et | Et | |
| 9-3 | Me | Cl | Et | Et | |
| 9-4 | Me | Br | Et | Et | |
| 9-5 | Me | I | Et | Et | |
| 9-6 | Me | CF$_3$ | Et | Et | |
| 9-7 | Me | CHF$_2$ | Et | Et | |
| 9-8 | Me | CF$_2$Cl | Et | Et | |
| 9-9 | Me | OMe | Et | Et | |
| 9-10 | Me | NO$_2$ | Et | Et | |
| 9-11 | Me | SO$_2$Me | Et | Et | |
| 9-12 | Cl | Me | Et | Et | |
| 9-13 | Cl | F | Et | Et | |
| 9-14 | Cl | Cl | Et | Et | (400 MHz, CDCl$_3$ δ, ppm) 7.49 (d, 1H), 7.46 (d, 1H), 3.29 (q, 4H), 1.51 (t, 6H) |
| 9-15 | Cl | Br | Et | Et | |
| 9-16 | Cl | I | Et | Et | |
| 9-17 | Cl | CF$_3$ | Et | Et | |
| 9-18 | Cl | CHF$_2$ | Et | Et | |
| 9-19 | Cl | CF$_2$Cl | Et | Et | |
| 9-20 | Cl | OMe | Et | Et | |

TABLE 9-continued

Inventive compounds of the general formula (I) in which Q is Q3 and R$^y$ is chlorine and R" and W are each hydrogen

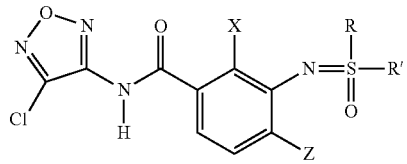

| No. | X | Z | R | R' | Physical data ($^1$H-NMR) |
|---|---|---|---|---|---|
| 9-21 | Cl | NO$_2$ | Et | Et | |
| 9-22 | Cl | SO$_2$Me | Et | Et | |
| 9-23 | OMe | Me | Et | Et | |
| 9-24 | OMe | F | Et | Et | |
| 9-25 | OMe | Cl | Et | Et | |
| 9-26 | OMe | Br | Et | Et | |
| 9-27 | OMe | I | Et | Et | |
| 9-28 | OMe | CF$_3$ | Et | Et | |
| 9-29 | OMe | CHF$_2$ | Et | Et | |
| 9-30 | OMe | CF$_2$Cl | Et | Et | |
| 9-31 | OMe | OMe | Et | Et | |
| 9-32 | OMe | NO$_2$ | Et | Et | |
| 9-33 | OMe | SO$_2$Me | Et | Et | |
| 9-34 | SO$_2$Me | Me | Et | Et | |
| 9-35 | SO$_2$Me | F | Et | Et | |
| 9-36 | SO$_2$Me | Cl | Et | Et | |
| 9-37 | SO$_2$Me | Br | Et | Et | |
| 9-38 | SO$_2$Me | I | Et | Et | |
| 9-39 | SO$_2$Me | CF$_3$ | Et | Et | |
| 9-40 | SO$_2$Me | CHF$_2$ | Et | Et | |
| 9-41 | SO$_2$Me | CF$_2$Cl | Et | Et | |
| 9-42 | SO$_2$Me | OMe | Et | Et | |
| 9-43 | SO$_2$Me | NO$_2$ | Et | Et | |
| 9-44 | SO$_2$Me | SO$_2$Me | Et | Et | |
| 9-45 | Me | Me | —(CH$_2$)$_5$— | | |
| 9-46 | Me | F | —(CH$_2$)$_5$— | | |
| 9-47 | Me | Cl | —(CH$_2$)$_5$— | | |
| 9-48 | Me | Br | —(CH$_2$)$_5$— | | |
| 9-49 | Me | I | —(CH$_2$)$_5$— | | |
| 9-50 | Me | CF$_3$ | —(CH$_2$)$_5$— | | |
| 9-51 | Me | CHF$_2$ | —(CH$_2$)$_5$— | | |
| 9-52 | Me | CF$_2$Cl | —(CH$_2$)$_5$— | | |
| 9-53 | Me | OMe | —(CH$_2$)$_5$— | | |
| 9-54 | Me | NO$_2$ | —(CH$_2$)$_5$— | | |
| 9-55 | Me | SO$_2$Me | —(CH$_2$)$_5$— | | |
| 9-56 | Cl | Me | —(CH$_2$)$_5$— | | |
| 9-57 | Cl | F | —(CH$_2$)$_5$— | | |
| 9-58 | Cl | Cl | —(CH$_2$)$_5$— | | (400 MHz, CDCl$_3$ δ, ppm) 7.48 (d, 1H), 7.45 (d, 1H), 3.40-3.25 (m, 4H), 2.30-2.11 (m, 4H), 1.88-1.80 (m, 1H), 1.70-1.53 (m, 1H) |
| 9-59 | Cl | Br | —(CH$_2$)$_5$— | | |
| 9-60 | Cl | I | —(CH$_2$)$_5$— | | |
| 9-61 | Cl | CF$_3$ | —(CH$_2$)$_5$— | | |
| 9-62 | Cl | CHF$_2$ | —(CH$_2$)$_5$— | | |
| 9-63 | Cl | CF$_2$Cl | —(CH$_2$)$_5$— | | |
| 9-64 | Cl | OMe | —(CH$_2$)$_5$— | | |
| 9-65 | Cl | NO$_2$ | —(CH$_2$)$_5$— | | |
| 9-66 | Cl | SO$_2$Me | —(CH$_2$)$_5$— | | |
| 9-67 | OMe | Me | —(CH$_2$)$_5$— | | |
| 9-68 | OMe | F | —(CH$_2$)$_5$— | | |
| 9-69 | OMe | Cl | —(CH$_2$)$_5$— | | |
| 9-70 | OMe | Br | —(CH$_2$)$_5$— | | |
| 9-71 | OMe | I | —(CH$_2$)$_5$— | | |
| 9-72 | OMe | CF$_3$ | —(CH$_2$)$_5$— | | |
| 9-73 | OMe | CHF$_2$ | —(CH$_2$)$_5$— | | |
| 9-74 | OMe | CF$_2$Cl | —(CH$_2$)$_5$— | | |
| 9-75 | OMe | OMe | —(CH$_2$)$_5$— | | |
| 9-76 | OMe | NO$_2$ | —(CH$_2$)$_5$— | | |
| 9-77 | OMe | SO$_2$Me | —(CH$_2$)$_5$— | | |
| 9-78 | SO$_2$Me | Me | —(CH$_2$)$_5$— | | |
| 9-79 | SO$_2$Me | F | —(CH$_2$)$_5$— | | |
| 9-80 | SO$_2$Me | Cl | —(CH$_2$)$_5$— | | |
| 9-81 | SO$_2$Me | Br | —(CH$_2$)$_5$— | | |
| 9-82 | SO$_2$Me | I | —(CH$_2$)$_5$— | | |
| 9-83 | SO$_2$Me | CF$_3$ | —(CH$_2$)$_5$— | | |

TABLE 9-continued

Inventive compounds of the general formula (I) in which Q is Q3 and $R^y$ is chlorine and R" and W are each hydrogen

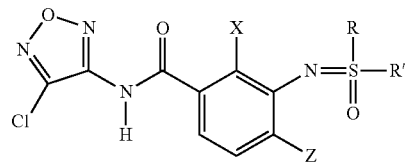

| No. | X | Z | R | R' | Physical data ($^1$H-NMR) |
|---|---|---|---|---|---|
| 9-84 | SO$_2$Me | CHF$_2$ | —(CH$_2$)$_5$— | | |
| 9-85 | SO$_2$Me | CF$_2$Cl | —(CH$_2$)$_5$— | | |
| 9-86 | SO$_2$Me | OMe | —(CH$_2$)$_5$— | | |
| 9-87 | SO$_2$Me | NO$_2$ | —(CH$_2$)$_5$— | | |
| 9-88 | SO$_2$Me | SO$_2$Me | —(CH$_2$)$_5$— | | |
| 9-89 | Me | Me | —(CH$_2$)$_2$O(CH$_2$)$_2$— | | |
| 9-90 | Me | F | —(CH$_2$)$_2$O(CH$_2$)$_2$— | | |
| 9-91 | Me | Cl | —(CH$_2$)$_2$O(CH$_2$)$_2$— | | |
| 9-92 | Me | Br | —(CH$_2$)$_2$O(CH$_2$)$_2$— | | |
| 9-93 | Me | I | —(CH$_2$)$_2$O(CH$_2$)$_2$— | | |
| 9-94 | Me | CF$_3$ | —(CH$_2$)$_2$O(CH$_2$)$_2$— | | |
| 9-95 | Me | CHF$_2$ | —(CH$_2$)$_2$O(CH$_2$)$_2$— | | |
| 9-96 | Me | CF$_2$Cl | —(CH$_2$)$_2$O(CH$_2$)$_2$— | | |
| 9-97 | Me | OMe | —(CH$_2$)$_2$O(CH$_2$)$_2$— | | |
| 9-98 | Me | NO$_2$ | —(CH$_2$)$_2$O(CH$_2$)$_2$— | | |
| 9-99 | Me | SO$_2$Me | —(CH$_2$)$_2$O(CH$_2$)$_2$— | | |
| 9-100 | Cl | Me | —(CH$_2$)$_2$O(CH$_2$)$_2$— | | |
| 9-101 | Cl | F | —(CH$_2$)$_2$O(CH$_2$)$_2$— | | |
| 9-102 | Cl | Cl | —(CH$_2$)$_2$O(CH$_2$)$_2$— | | (400 MHz, DMSO-d$_6$ δ, ppm) 7.57 (d, 1H), 7.27 (d, 1H), 4.23-4.12 (m, 2H), 4.06-3.97 (m, 2H), 3.55-3.40 (m, 4H) |
| 9-103 | Cl | Br | —(CH$_2$)$_2$O(CH$_2$)$_2$— | | |
| 9-104 | Cl | I | —(CH$_2$)$_2$O(CH$_2$)$_2$— | | |
| 9-105 | Cl | CF$_3$ | —(CH$_2$)$_2$O(CH$_2$)$_2$— | | |
| 9-106 | Cl | CHF$_2$ | —(CH$_2$)$_2$O(CH$_2$)$_2$— | | |
| 9-107 | Cl | CF$_2$Cl | —(CH$_2$)$_2$O(CH$_2$)$_2$— | | |
| 9-108 | Cl | OMe | —(CH$_2$)$_2$O(CH$_2$)$_2$— | | |
| 9-109 | Cl | NO$_2$ | —(CH$_2$)$_2$O(CH$_2$)$_2$— | | |
| 9-110 | Cl | SO$_2$Me | —(CH$_2$)$_2$O(CH$_2$)$_2$— | | |
| 9-111 | OMe | Me | —(CH$_2$)$_2$O(CH$_2$)$_2$— | | |
| 9-112 | OMe | F | —(CH$_2$)$_2$O(CH$_2$)$_2$— | | |
| 9-113 | OMe | Cl | —(CH$_2$)$_2$O(CH$_2$)$_2$— | | |
| 9-114 | OMe | Br | —(CH$_2$)$_2$O(CH$_2$)$_2$— | | |
| 9-115 | OMe | I | —(CH$_2$)$_2$O(CH$_2$)$_2$— | | |
| 9-116 | OMe | CF$_3$ | —(CH$_2$)$_2$O(CH$_2$)$_2$— | | |
| 9-117 | OMe | CHF$_2$ | —(CH$_2$)$_2$O(CH$_2$)$_2$— | | |
| 9-118 | OMe | CF$_2$Cl | —(CH$_2$)$_2$O(CH$_2$)$_2$— | | |
| 9-119 | OMe | OMe | —(CH$_2$)$_2$O(CH$_2$)$_2$— | | |
| 9-120 | OMe | NO$_2$ | —(CH$_2$)$_2$O(CH$_2$)$_2$— | | |
| 9-121 | OMe | SO$_2$Me | —(CH$_2$)$_2$O(CH$_2$)$_2$— | | |
| 9-122 | SO$_2$Me | Me | —(CH$_2$)$_2$O(CH$_2$)$_2$— | | |
| 9-123 | SO$_2$Me | F | —(CH$_2$)$_2$O(CH$_2$)$_2$— | | |
| 9-124 | SO$_2$Me | Cl | —(CH$_2$)$_2$O(CH$_2$)$_2$— | | |
| 9-125 | SO$_2$Me | Br | —(CH$_2$)$_2$O(CH$_2$)$_2$— | | |
| 9-126 | SO$_2$Me | I | —(CH$_2$)$_2$O(CH$_2$)$_2$— | | |
| 9-127 | SO$_2$Me | CF$_3$ | —(CH$_2$)$_2$O(CH$_2$)$_2$— | | |
| 9-128 | SO$_2$Me | CHF$_2$ | —(CH$_2$)$_2$O(CH$_2$)$_2$— | | |
| 9-129 | SO$_2$Me | CF$_2$Cl | —(CH$_2$)$_2$O(CH$_2$)$_2$— | | |
| 9-130 | SO$_2$Me | OMe | —(CH$_2$)$_2$O(CH$_2$)$_2$— | | |
| 9-131 | SO$_2$Me | NO$_2$ | —(CH$_2$)$_2$O(CH$_2$)$_2$— | | |
| 9-132 | SO$_2$Me | SO$_2$Me | —(CH$_2$)$_2$O(CH$_2$)$_2$— | | |
| 9-133 | Cl | COOMe | Et | Et | |
| 9-134 | Cl | COOMe | —(CH$_2$)$_5$— | | |
| 9-135 | Cl | COOMe | —(CH$_2$)$_2$O(CH$_2$)$_2$— | | |

B. Formulation Examples a) A dusting product is obtained by mixing 10 parts by weight of a compound of the formula (I) and/or salts thereof and 90 parts by weight of talc as inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.
d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.
e) Water-dispersible granules are obtained by mixing
   75 parts by weight of a compound of the formula (I) and/or salts thereof,
   10 parts by weight of calcium lignosulfonate,
   5 parts by weight of sodium laurylsulfate,
   3 parts by weight of polyvinyl alcohol and
   7 parts by weight of kaolin,
   grinding the mixture in a pinned-disk mill and granulating the powder in a fluidized bed by spraying on water as a granulating liquid.
f) Water-dispersible granules are also obtained by homogenizing and precomminuting
   25 parts by weight of a compound of the formula (I) and/or salts thereof,
   5 parts by weight of sodium 2,2'-dinaphthylmethane-6,6'-disulfonate,
   2 parts by weight of sodium oleoylmethyltaurate,
   1 part by weight of polyvinyl alcohol,
   17 parts by weight of calcium carbonate and
   50 parts by weight of water
   in a colloid mill, then grinding the mixture in a bead mill and atomizing and drying the resulting suspension in a spray tower by means of a one-phase nozzle.

C. Biological Examples

1. Pre-Emergence Herbicidal Action Against Weed Plants

Seeds of monocotyledonous and dicotyledonous weed plants and crop plants are placed in wood-fiber pots in sandy loam and covered with soil. The inventive compounds formulated in the form of wettable powders (WP) or as emulsion concentrates (EC) are then applied to the surface of the covering soil as an aqueous suspension or emulsion at a water application rate of 600 to 800 l/ha (converted) with addition of 0.2% wetting agent. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). For example, compounds No. 6-102, 6-014 and 6-058 at an application rate of 320 g/ha each show at least 80% efficacy against *Abutilon theophrasti, Amaranthus retroflexus* and *Matricaria inodora*.

2. Post-emergence Herbicidal Action Against Weed Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The inventive compounds formulated in the form of wettable powders (WP) or as emulsion concentrates (EC) are then sprayed onto the green parts of the plants as an aqueous suspension or emulsion at a water application rate of 600 to 800 l/ha (converted) with addition of 0.2% wetting agent. After the test plants have been left to stand in the greenhouse under optimal growth conditions for about 3 weeks, the action of the formulations is assessed visually in comparison to untreated controls (herbicidal action in percent (%): 100% activity=the plants have died, 0% activity=like control plants). Numerous inventive compounds, each at an application rate of 80 g/ha, exhibit excellent efficacy against a multitude of unwanted plants.

3. Comparative Tests

In accordance with the conditions specified for pre-emergence testing of herbicidal efficacy against harmful plants, comparative tests were conducted between inventive compounds and compounds known from WO 2011035874 A1. The test results show that the inventive compounds exhibit superior efficacy against numerous harmful plants.

The abbreviations used here mean:

| ABUTH | *Abutilon theophrasti* | AMARE | *Amaranthus retroflexus* |
| AVEFA | *Avena fatua* | MATIN | *Matricaria inodora* |
| PHBPU | *Pharbitis purpureum* | STEME | *Stellaria media* |
| VERPE | *Veronica persica* | | |

TABLE A

Pre-emergence herbicidal efficacy

| Compound | Dosage [g/ha] | Herbicidal efficacy against | | | | |
| --- | --- | --- | --- | --- | --- | --- |
| | | ABUTH | AMARE | MATIN | PHBPU | VERPE |
| Inventive example no. 6-014 | 320 | 80% | 90% | 90% | 80% | 90% |

TABLE A-continued

Pre-emergence herbicidal efficacy

| Compound | Dosage [g/ha] | Herbicidal efficacy against | | | | |
|---|---|---|---|---|---|---|
| | | ABUTH | AMARE | MATIN | PHBPU | VERPE |
| Example no. 1-308 from WO 2011/035874 A1 | 320 | 0% | 30% | 0% | 10% | 40% |

TABLE B

Pre-emergence herbicidal efficacy

| Compound | Dosage [g/ha] | Herbicidal efficacy against | | | |
|---|---|---|---|---|---|
| | | ABUTH | AMARE | MATIN | STEME |
| Inventive example no. 6-058 | 320 | 90% | 60% | 90% | 70% |
| Example no. 1-308 from WO 2011/035874 A1 | 320 | 0% | 30% | 0% | 0% |

TABLE C

Pre-emergence herbicidal efficacy

| Compound | Dosage [g/ha] | Herbicidal efficacy against | | | |
|---|---|---|---|---|---|
| | | AVEFA | MATIN | PHBPU | STEME |
| Inventive example no. 6-102 | 320 | 70% | 100% | 100% | 90% |

TABLE C-continued

Pre-emergence herbicidal efficacy

| Compound | Dosage [g/ha] | Herbicidal efficacy against | | | |
|---|---|---|---|---|---|
| | | AVEFA | MATIN | PHBPU | STEME |
|  Example no. 1-308 from WO 2011/035874 A1 | 320 | 0% | 0% | 10% | 0% |

The invention claimed is:

1. A sulfinylaminobenzamide of the formula (I) and/or a salt thereof

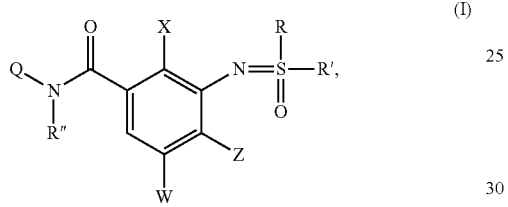

in which
Q is a Q3 radical,

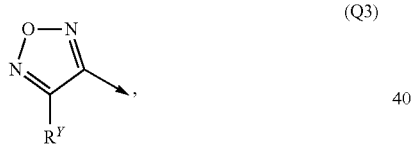

X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON\!\!=\!\!)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $(R^1O)(R^1)N(O)C$—$(C_1-C_6)$-alkyl, $(R^1)_2N(R^1)N(O)C$—$(C_1-C_6)$-alkyl, $R^1(O)C(R^1)N(O)C$—$(C_1-C_6)$-alkyl, $R^2O(O)C(R^1)N(O)C$—$(C_1-C_6)$-alkyl, $(R^1)_2N(O)C(R^1)N(O)C$—$(C_1-C_6)$-alkyl, $R^2(O)_2S(R^1)N(O)C$—$(C_1-C_6)$-alkyl, $R^1O(O)_2S(R^1)N(O)C$—$(C_1-C_6)$-alkyl, $(R^1)_2N(O)_2S(R^1)N(O)C$—$(C_1-C_6)$-alkyl, NC—$(C_1-C_6)$-alkyl, $R^1O$—$(C_1-C_6)$-alkyl, $R^1(O)CO$—$(C_1-C_6)$-alkyl, $R^2(O)_2SO$—$(C_1-C_6)$-alkyl, $R^2O$(O)CO—$(C_1-C_6)$-alkyl, $(R^1)_2N(O)CO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^1O(O)_2S(R^1)N$—$(C_1-C_6)$-alkyl, $(R^1)_2N(O)_2S(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, Z is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON\!\!=\!\!)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $(R^1O)(R^1)N(O)C$—$(C_1-C_6)$-alkyl, $(R^1)_2N(R^1)N(O)C$—$(C_1-C_6)$-alkyl, $R^1(O)C(R^1)N(O)C$—$(C_1-C_6)$-alkyl, $R^2O(O)C(R^1)N(O)C$—$(C_1-C_6)$-alkyl, $(R^1)_2N(O)C(R^1)N(O)C$—$(C_1-C_6)$-alkyl, $R^2(O)_2S(R^1)N(O)C$—$(C_1-C_6)$-alkyl, $R^1O(O)_2S(R^1)N(O)C$—$(C_1-C_6)$-alkyl, $(R^1)_2N(O)_2S(R^1)N(O)C$—$(C_1-C_6)$-alkyl, NC—$(C_1-C_6)$-alkyl, $R^1O$—$(C_1-C_6)$-alkyl, $R^1(O)CO$—$(C_1-C_6)$-alkyl, $R^2(O)_2SO$—$(C_1-C_6)$-alkyl, $R^2O(O)CO$—$(C_1-C_6)$-alkyl, $(R^1)_2N(O)CO$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^1O(O)_2S(R^1)N$—$(C_1-C_6)$-alkyl, $(R^1)_2N(O)_2S(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, R¹(O)C(R¹)N(O)₂S—(C₁-C₆)-alkyl, R²O(O)C(R¹)N(O)₂S—(C₁-C₆)-alkyl, (R¹)₂N(O)C(R¹)N(O)₂S—(C₁-C₆)-alkyl, (R⁵O)₂(O)P—(C₁-C₆)-alkyl, phenyl, heteroaryl, heterocyclyl, phenyl-(C₁-C₆)-alkyl, heteroaryl-(C₁-C₆)-alkyl, heterocyclyl-(C₁-C₆)-alkyl, where the six latter radicals are each substituted by s radicals from the group consisting of nitro, halogen, cyano, thiocyanato, (C₁-C₆)-alkyl, halo-(C₁-C₆)-alkyl, (C₃-C₆)-cycloalkyl, R¹O(O)C, (R¹)₂N(O)C, R¹O, (R¹)₂N, R²(O)ₙS, R¹O(O)₂S, (R¹)₂N(O)₂S and R¹O—(C₁-C₆)-alkyl, and where heterocyclyl bears n oxo groups, W is hydrogen, halogen, nitro, cyano, thiocyanato, (C₁-C₆)-alkyl, halo-(C₁-C₆)-alkyl, (C₂-C₆)-alkenyl, halo-(C₂-C₆)-alkenyl, (C₂-C₆)-alkynyl, halo-(C₃-C₆)-alkynyl, (C₃-C₇)-cycloalkyl, halo-(C₃-C₇)-cycloalkyl, (C₁-C₆)-alkoxy, halo-(C₁-C₆)-alkoxy, (C₁-C₆)-alkyl-(O)ₙS—, (C₁-C₆)-haloalkyl-(O)ₙS—, (C₁-C₆)-alkoxy-(C₁-C₄)-alkyl, (C₁-C₆)-alkoxy-(C₁-C₄)-haloalkyl, R¹(O)C, R¹(R¹ON=)C, R¹O(O)C, (R¹)₂N, R¹(O)C(R¹)N or R²(O)₂S(R¹)N, R and R' are each independently (C₁-C₆)-alkyl, halo-(C₁-C₆)-alkyl, (C₂-C₆)-alkenyl, halo-(C₂-C₆)-alkenyl, (C₂-C₆)-alkynyl, halo-(C₃-C₆)-alkynyl, (C₃-C₆)-cycloalkyl, halo-(C₃-C₆)-cycloalkyl, (C₃-C₆)-cycloalkyl-(C₁-C₆)-alkyl, halo-(C₃-C₆)-cycloalkyl-(C₁-C₆)-alkyl, (C₁-C₆)-alkoxy-(C₁-C₆)-alkyl, halo-(C₁-C₆)-alkoxy-(C₁-C₆)-alkyl, phenyl, heteroaryl or heterocyclyl, where the three latter radicals are each substituted by s radicals selected from the group consisting of nitro, halogen, cyano, thiocyanato, (C₁-C₆)-alkyl, halo-(C₁-C₆)-alkyl, (C₃-C₆)-cycloalkyl, R¹O(O)C, (R¹)₂N(O)C, R¹O, (R¹)₂N, R²(O)ₙS, R¹O(O)₂S, (R¹)₂N(O)₂S and R¹O—(C₁-C₆)-alkyl, and where heterocyclyl bears n oxo groups, or R and R' together with the sulfur atom to which they are bonded form a 3- to 8-membered unsaturated, semisaturated or saturated ring which contains, apart from the carbon atoms and apart from the sulfur atom of the sulfoximino group, in each case m ring members selected from the group consisting of N(R¹), O and S(O)ₙ, and where this ring in each case is substituted by s radicals from the group consisting of nitro, halogen, cyano, thiocyanato, (C₁-C₆)-alkyl, halo-(C₁-C₆)-alkyl, (C₃-C₆)-cycloalkyl, R¹O(O)C, (R¹)₂N(O)C, R¹O, (R¹)₂N, R²(O)ₙS, R¹O(O)₂S, (R¹)₂N(O)₂S and R¹O—(C₁-C₆)-alkyl, and where this ring bears n oxo groups, R" is hydrogen, (C₁-C₆)-alkyl, halo-(C₁-C₆)-alkyl, (C₂-C₆)-alkenyl, halo-(C₂-C₆)-alkenyl, (C₂-C₆)-alkynyl, halo-(C₃-C₆)-alkynyl, (C₃-C₆)-cycloalkyl, halo-(C₃-C₆)-cycloalkyl, (C₃-C₆)-cycloalkyl-(C₁-C₆)-alkyl, halo-(C₃-C₆)-cycloalkyl-(C₁-C₆)-alkyl, R¹(O)C—(C₁-C₆)-alkyl, R¹O(O)C—(C₁-C₆)-alkyl, (R¹)₂N(O)C—(C₁-C₆)-alkyl, NC—(C₁-C₆)-alkyl, R¹O—(C₁-C₆)-alkyl, R¹(O)CO—(C₁-C₆)-alkyl, R²(O)₂SO—(C₁-C₆)-alkyl, (R¹)₂N—(C₁-C₆)-alkyl, R¹(O)C(R¹)N—(C₁-C₆)-alkyl, R²(O)₂S(R¹)N—(C₁-C₆)-alkyl, R²(O)ₙS—(C₁-C₆)-alkyl, R¹O(O)₂S—(C₁-C₆)-alkyl, (R¹)₂N(O)₂S—(C₁-C₆)-alkyl, R¹(O)C, R¹O(O)C, (R¹)₂N(O)C, R¹O, (R¹)₂N, R²O(O)C(R¹)N, (R¹)₂N(O)C(R¹)N, R²(O)₂S, or benzyl substituted in each case by s radicals selected from the group consisting of methyl, ethyl, methoxy, nitro, trifluoromethyl and halogen, Rʸ is hydrogen, (C₁-C₆)-alkyl, halo-(C₁-C₆)-alkyl, (C₂-C₆)-alkenyl, halo-(C₂-C₆)-alkenyl, (C₂-C₆)-alkynyl, halo-(C₃-C₆)-alkynyl, (C₃-C₇)-cycloalkyl, (C₁-C₆)-alkoxy, halo-(C₁-C₆)-alkoxy, (C₂-C₆)-alkenyloxy, (C₂-C₆)-alkynyloxy, cyano, nitro, methylsulfanyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl each substituted by s radicals selected from the group consisting of (C₁-C₆)-alkyl, halo-(C₁-C₆)-alkyl, (C₁-C₆)-alkoxy, halo-(C₁-C₆)-alkoxy and halogen, and where heterocyclyl bears n oxo groups, R¹ is hydrogen, (C₁-C₆)-alkyl, halo-(C₁-C₆)-alkyl, (C₂-C₆)-alkenyl, halo-(C₂-C₆)-alkenyl, (C₂-C₆)-alkynyl, halo-(C₂-C₆)-alkynyl, (C₃-C₆)-cycloalkyl, (C₃-C₆)-cycloalkenyl, halo-(C₃-C₆)-cycloalkyl, (C₃-C₆)-cycloalkyl-(C₁-C₆)-alkyl, (C₁-C₆)-alkyl-O—(C₁-C₆)-alkyl, cycloalkyl-(C₁-C₆)-alkyl-O—(C₁-C₆)-alkyl, phenyl, phenyl-(C₁-C₆)-alkyl, heteroaryl, heteroaryl-(C₁-C₆)-alkyl, heterocyclyl, heterocyclyl-(C₁-C₆)-alkyl, phenyl-O—(C₁-C₆)-alkyl, heteroaryl-O—(C₁-C₆)-alkyl, heterocyclyl-O—(C₁-C₆)-alkyl, phenyl-N(R³)—(C₁-C₆)-alkyl, heteroaryl-N(R³)—(C₁-C₆)-alkyl, heterocyclyl-N(R³)—(C₁-C₆)-alkyl, phenyl-S(O)ₙ—(C₁-C₆)-alkyl, heteroaryl-S(O)ₙ—(C₁-C₆)-alkyl, heterocyclyl-S(O)ₙ—(C₁-C₆)-alkyl, where the fifteen latter radicals are each substituted by s radicals selected from the group consisting of nitro, halogen, cyano, thiocyanato, (C₁-C₆)-alkyl, halo-(C₁-C₆)-alkyl, (C₃-C₆)-cycloalkyl, R³O(O)C, (R³)₂N(O)C, R³O, (R³)₂N, R⁴(O)ₙS, R³O(O)₂S, (R³)₂N(O)₂S and R³O—(C₁-C₆)-alkyl, and where heterocyclyl bears n oxo groups, R² is (C₁-C₆)-alkyl, halo-(C₁-C₆)-alkyl, (C₂-C₆)-alkenyl, halo-(C₂-C₆)-alkenyl, (C₂-C₆)-alkynyl, halo-(C₃-C₆)-alkynyl, (C₃-C₆)-cycloalkyl, (C₃-C₆)-cycloalkenyl, halo-(C₃-C₆)-cycloalkyl, (C₃-C₆)-cycloalkyl-(C₁-C₆)-alkyl, (C₁-C₆)-alkyl-O—(C₁-C₆)-alkyl, cycloalkyl-(C₁-C₆)-alkyl-O—(C₁-C₆)-alkyl, phenyl, phenyl-(C₁-C₆)-alkyl, heteroaryl, heteroaryl-(C₁-C₆)-alkyl, heterocyclyl, heterocyclyl-(C₁-C₆)-alkyl, phenyl-O—(C₁-C₆)-alkyl, heteroaryl-O—(C₁-C₆)-alkyl, heterocyclyl-O—(C₁-C₆)-alkyl, phenyl-N(R³)—(C₁-C₆)-alkyl, heteroaryl-N(R³)—(C₁-C₆)-alkyl, heterocyclyl-N(R³)—(C₁-C₆)-alkyl, phenyl-S(O)ₙ—(C₁-C₆)-alkyl, heteroaryl-S(O)ₙ—(C₁-C₆)-alkyl, heterocyclyl-S(O)ₙ—(C₁-C₆)-alkyl, where the fifteen latter radicals are each substituted by s radicals selected from the group consisting of nitro, halogen, cyano, thiocyanato, (C₁-C₆)-alkyl, halo-(C₁-C₆)-alkyl, (C₃-C₆)-cycloalkyl, R³O(O)C, (R³)₂N(O)C, R³O, (R³)₂N, R⁴(O)ₙS, R³O(O)₂S, (R³)₂N(O)₂S and R³O—(C₁-C₆)-alkyl, and where heterocyclyl bears n oxo groups, R³ is hydrogen, (C₁-C₆)-alkyl, halo-(C₁-C₆)-alkyl, (C₂-C₆)-alkenyl, (C₂-C₆)-alkynyl, (C₃-C₆)-cycloalkyl, (C₃-C₆)-cycloalkyl-(C₁-C₆)-alkyl or phenyl, R⁴ is (C₁-C₆)-alkyl, halo-(C₁-C₆)-alkyl, (C₂-C₆)-alkenyl, (C₂-C₆)-alkynyl, (C₃-C₆)-cycloalkyl, (C₃-C₆)-cycloalkyl-(C₁-C₆)-alkyl or phenyl, R⁵ is hydrogen or (C₁-C₄)-alkyl, R⁷ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, or (C₃-C₆)-cycloalkyl, or is heteroaryl or heterocyclyl each of which is substituted by s radicals selected from the group consisting of methyl, ethyl, methoxy, trifluoromethyl and halogen, n is 0, 1 or 2,
m is 0, 1, 2, 3 or 4,
s is 0, 1, 2 or 3.

2. A sulfinylaminobenzamide and/or salt thereof as claimed in claim 1, in which
Q is a Q3 radical,

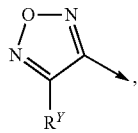

X is nitro, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by s radicals selected from the group consisting of nitro, halogen, cyano, thiocyanato, $(C_1-C_6)$-alkyl, halo-$(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, Z is hydrogen, nitro, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)O(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1-C_6)$-alkyl, $R^1O(O)C$—$(C_1-C_6)$-alkyl, $(R^1)_2N(O)C$—$(C_1-C_6)$-alkyl, NC—$(C_1-C_6)$-alkyl, $R^1O$—$(C_1-C_6)$-alkyl, $(R^1)_2N$—$(C_1-C_6)$-alkyl, $R^1(O)C(R^1)N$—$(C_1-C_6)$-alkyl, $R^2(O)_2S(R^1)N$—$(C_1-C_6)$-alkyl, $R^2O(O)C(R^1)N$—$(C_1-C_6)$-alkyl, $(R^1)_2N(O)C(R^1)N$—$(C_1-C_6)$-alkyl, $R^2(O)_nS$—$(C_1-C_6)$-alkyl, $R^1O(O)_2S$—$(C_1-C_6)$-alkyl, $(R^1)_2N(O)_2S$—$(C_1-C_6)$-alkyl, $(R^5O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by s radicals selected from the group consisting of nitro, halogen, cyano, thiocyanato, $(C_1-C_6)$-alkyl, halo-$(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl, and where heterocyclyl bears n oxo groups, W is hydrogen, halogen, nitro, cyano, $(C_1-C_6)$-alkyl, halo-$(C_1-C_6)$-alkyl, $(C_3-C_7)$-cycloalkyl, $(C_1-C_6)$-alkoxy, $(C_1-C_6)$-alkyl-$(O)_nS$—, $R^1O(O)C$, $(R^1)_2N$, $R^1(O)C(R^1)N$ or $R^2(O)_2S(R^1)N$, R and R' are each independently $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $(C_1-C_6)$-alkoxy-$(C_1-C_6)$-alkyl, halo-$(C_1-C_6)$-alkoxy-$(C_1-C_6)$-alkyl, phenyl, heteroaryl or heterocyclyl, where the three latter radicals are each substituted by s radicals selected from the group consisting of nitro, halogen, $(C_1-C_6)$-alkyl, halo-$(C_1-C_6)$-alkyl, $R^1O(O)C$, $(R^1)_2N(O)C$, $R^1O$, $(R^1)_2N$, $R^2(O)_nS$ and $R^1O$—$(C_1-C_6)$-alkyl, and where heterocyclyl bears n oxo groups, or R and R' together with the sulfur atom to which they are bonded form a 3- to 8-membered unsaturated, semisaturated or saturated ring which contains, apart from the carbon atoms and apart from the sulfur atom of the sulfoximino group, in each case m ring members from the group consisting of $N(R^1)$, O and $S(O)_n$, and where this ring in each case is substituted by s radicals from the group consisting of halogen, $(C_1-C_6)$-alkyl, halo-$(C_1-C_6)$-alkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1-C_6)$-alkyl, and where this ring bears n oxo groups, R" is hydrogen, $R^Y$ is hydrogen, $(C_1-C_6)$-alkyl, halo-$(C_1-C_6)$-alkyl, $(C_3-C_7)$-cycloalkyl, $(C_1-C_6)$-alkoxy, methoxycarbonyl, methoxycarbonylmethyl, halogen, amino, aminocarbonyl or methoxymethyl, $R^1$ is hydrogen, $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, where the nine latter radicals are each substituted by s radicals selected from the group consisting of nitro, halogen, $(C_1-C_6)$-alkyl, halo-$(C_1-C_6)$-alkyl, $R^3O(O)C$, $(R^3)_2N(O)C$, $R^3O$, $(R^3)_2N$, $R^4(O)_nS$ and $R^3O$—$(C_1-C_6)$-alkyl, and where heterocyclyl bears n oxo groups, $R^2$ is $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, where the nine latter radicals are each substituted by s radicals selected from the group consisting of nitro, halogen, $(C_1-C_6)$-alkyl, halo-$(C_1-C_6)$-alkyl, $R^3O(O)C$, $(R^3)_2N(O)C$, $R^3O$, $(R^3)_2N$, $R^4(O)_nS$ and $R^3O$—$(C_1-C_6)$-alkyl, and where heterocyclyl bears n oxo groups, $R^3$ is hydrogen or $(C_1-C_6)$-alkyl, $R^4$ is $(C_1-C_6)$-alkyl, $R^5$ is hydrogen or $(C_1-C_4)$-alkyl, $R^7$ is acetoxy, acetamido, methoxycarbonyl or $(C_3-C_6)$-cycloalkyl, n is 0, 1 or 2, m is 0, 1 or 2, s is 0, 1, 2 or 3.

3. A sulfinylaminobenzamide and/or salt as claimed in claim 1, in which
Q is a Q3 radical,

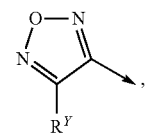

X is nitro, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, hydroxycarbonyl, methoxycarbonyl, ethoxycarbonyl, methoxy, ethoxy, methylsulfanyl, methylsulfinyl, methylsulfonyl, methoxymethyl, ethoxymethyl, methoxyethyl, methoxyethoxymethyl, methylthiomethyl, methylsulfinylmethyl or methylsulfonylmethyl, Z is hydrogen, nitro, cyano, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, hydroxycarbonyl, methoxycarbonyl, ethoxycarbonyl, methoxy, ethoxy, methylsulfanyl, methylsulfinyl or methylsulfonyl, W is hydrogen, chlorine or methyl, R and R' are each independently methyl, ethyl or n-propyl, or R and R' together with the sulfur atom to which they are bonded form a 5- or 6-membered ring which, apart from the carbon atoms and apart from the sulfur atom of the sulfoximino group, contains m oxygen atoms, R" is hydrogen, $R^Y$ is methyl, ethyl, n-propyl, chlorine or amino, and m is 0 or 1.

4. A herbicidal composition, comprising a herbicidally active content of at least one compound of the formula (I) and/or salt as claimed in claim 1.

5. The herbicidal composition as claimed in claim 4 in a mixture with one or more formulation auxiliaries.

6. The herbicidal composition as claimed in claim 4, comprising at least one further pesticidally active substance selected from the group consisting of insecticides, acaricides, herbicides, fungicides, safeners and growth regulators.

7. The herbicidal composition as claimed in claim 6, comprising a safener.

8. The herbicidal composition as claimed in claim 7, comprising cyprosulfamide, cloquintocet-mexyl, mefenpyr-diethyl or isoxadifen-ethyl.

9. The herbicidal composition as claimed in claim 6, comprising a further herbicide.

10. A method of controlling one or more unwanted plants, comprising applying an effective amount of at least one compound of the formula (I) and/or salt as claimed in any of claim 1 to the plants and/or to a site of unwanted vegetation.

11. A method of controlling unwanted plants comprising applying a compound of formula (I) and/or salt as claimed in claim 1 to one or more unwanted plants.

12. A method of controlling unwanted plants as claimed in claim 11 comprising applying a compound of formula (I) and/or salt as claimed in claim 1 to one or more unwanted plants in the presence of one or more crops of useful plants.

13. A method of controlling unwanted plants as claimed in claim 12 wherein the useful plants are transgenic useful plants.

14. A sulfinylaminobenzamide and/or salt as claimed in claim 1, in which
Q is a Q3 radical,

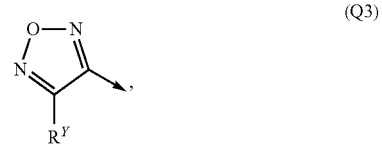

X is halogen,
Z is halogen,
W is hydrogen,
R and R' are each independently $(C_1-C_6)$-alkyl, or R and R' together with the sulfur atom to which they are bonded form a 6-membered ring which, apart from the carbon atoms and apart from the sulfur atom of the sulfoximino group, contains m oxygen atoms,
R" is hydrogen,
$R^Y$ is $(C_1-C_6)$-alkyl, and
m is 0 or 1.

15. A sulfinylaminobenzamide as claimed in claim 1 of the formula

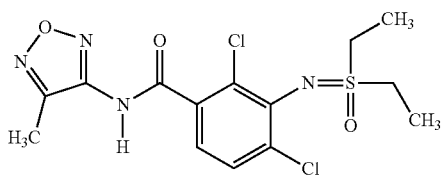 [SMILES: CCS(=O)(CC)=Nc1c(Cl)ccc(C(=O)Nc2nonc2C)c1Cl]

and/or a salt thereof.

16. A sulfinylaminobenzamide as claimed in claim 1 of the formula

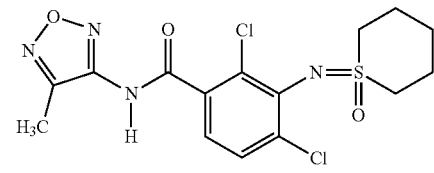 [SMILES: Cc1nonc1NC(=O)c1ccc(Cl)c(N=S2(=O)CCCCC2)c1Cl]

and/or a salt thereof.

17. A sulfinylaminobenzamide as claimed in claim 1 of the formula

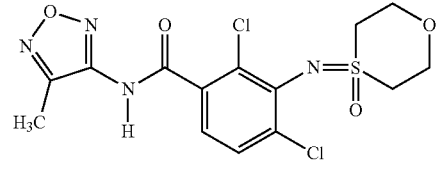 [SMILES: Cc1nonc1NC(=O)c1ccc(Cl)c(N=S2(=O)CCOCC2)c1Cl]

and/or a salt thereof.

* * * * *